United States Patent
Rito et al.

(10) Patent No.: US 7,041,684 B2
(45) Date of Patent: *May 9, 2006

(54) SELECTIVE β₃ ADRENERGIC AGONISTS

(75) Inventors: Christopher J. Rito, Mooresville, IN (US); Anthony J. Shuker, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 263 days.

This patent is subject to a terminal disclaimer.

(21) Appl. No.: 10/694,467

(22) Filed: Oct. 27, 2003

(65) Prior Publication Data

US 2005/0043337 A1    Feb. 24, 2005

Related U.S. Application Data

(60) Continuation of application No. 10/120,302, filed on Apr. 10, 2002, now Pat. No. 6,686,372, which is a continuation of application No. 09/610,096, filed on Jun. 30, 2000, now Pat. No. 6,413,991, which is a division of application No. 09/068,192, filed as application No. PCT/US97/15230 on Aug. 28, 1997, now Pat. No. 6,140,352.

(60) Provisional application No. 60/029,228, filed on Oct. 30, 1996, provisional application No. 60/025,818, filed on Sep. 5, 1996.

(51) Int. Cl.
A61K 31/4439 (2006.01)
C07D 401/12 (2006.01)

(52) U.S. Cl. .................... 514/339; 546/276.7
(58) Field of Classification Search ............. 546/276.7; 514/339
See application file for complete search history.

(56) References Cited

U.S. PATENT DOCUMENTS

| | | | |
|---|---|---|---|
| 4,032,575 A | 6/1977 | Ikezaki et al. |
| 4,140,789 A | 2/1979 | Jaeggi et al. |
| 4,235,919 A | 11/1980 | Berthold |
| 4,288,452 A | 9/1981 | Sombroek et al. |
| 4,309,443 A | 1/1982 | Smith et al. |
| 4,310,527 A | 1/1982 | Jaeggi |
| 4,338,333 A | 7/1982 | Ainsworth et al. |
| 4,346,093 A | 8/1982 | Friebe et al. |
| 4,367,235 A | 1/1983 | Ross et al. |
| 4,385,066 A | 5/1983 | Ainsworth et al. |
| 4,391,826 A | 7/1983 | Mills et al. |
| 4,396,627 A | 8/1983 | Ainsworth et al. |
| 4,432,993 A | 2/1984 | Ferris |
| 4,478,849 A | 10/1984 | Ainsworth et al. |
| 4,497,813 A | 2/1985 | Ostermayer et al. |
| 4,503,067 A | 3/1985 | Wiedemann et al. |
| 4,513,001 A | 4/1985 | Joannic et al. |
| 4,636,511 A | 1/1987 | Ostermayer et al. |
| 4,652,679 A | 3/1987 | Alig et al. |
| 4,697,022 A | 9/1987 | Leinert |
| 4,727,067 A | 2/1988 | Ostermayer et al. |
| 4,751,246 A | 6/1988 | Philion |
| 4,772,631 A | 9/1988 | Holloway et al. |
| 4,892,886 A | 1/1990 | Alig et al. |
| 4,940,800 A | 7/1990 | Bertolini et al. |
| 4,960,783 A | 10/1990 | Bonse et al. |
| 4,977,148 A | 12/1990 | Holloway et al. |
| 5,013,761 A | 5/1991 | Beedle et al. |
| 5,064,863 A | 11/1991 | Alig et al. |
| 5,166,218 A | 11/1992 | Alig et al. |
| 5,254,595 A | 10/1993 | Guzzi et al. |
| 5,321,036 A | 6/1994 | Sher |
| 5,393,772 A | 2/1995 | Yue et al. |
| 5,420,294 A | 5/1995 | Beedle et al. |
| 5,453,436 A | 9/1995 | Ohlstein |
| 5,488,151 A | 1/1996 | Baroni et al. |
| 5,534,640 A | 7/1996 | Tegeler et al. |
| 5,541,197 A | 7/1996 | Fisher et al. |
| 5,541,204 A | 7/1996 | Sher et al. |
| 5,561,142 A | 10/1996 | Fisher et al. |
| 5,574,164 A | 11/1996 | Tegeler et al. |
| 5,776,983 A | 7/1998 | Washburn et al. |
| 6,140,352 A * | 10/2000 | Crowell et al. ............. 514/339 |

FOREIGN PATENT DOCUMENTS

CH    636856 A5    6/1983

(Continued)

OTHER PUBLICATIONS

Tejani-Butt and Brunswick. "Synthesis an β-Adrenergic Receptor Blocking Potency of 1-(Substituted amino)-3-(4-indolyloxy) propan-2-ols" J. Med. Chem 29:1524-1527 (1986).

(Continued)

*Primary Examiner*—Patricia L. Morris
(74) *Attorney, Agent, or Firm*—Gilbert T. Voy

(57) ABSTRACT

The present invention is in the field of medicine, particularly in the treatment of Type II diabetes and obesity. More specifically, the present invention relates to selective β₃ receptor agonists useful in the treatment of Type II diabetes and obesity. The invention provides compounds and methods of treating Type II diabetes and obesity, comprising administering to a mammal in need thereof compounds of formula (I).

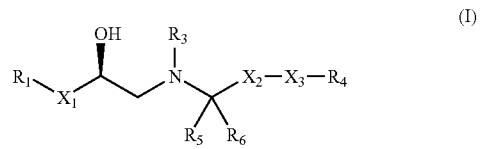

9 Claims, No Drawings

FOREIGN PATENT DOCUMENTS

| | | |
|---|---|---|
| DE | 4040186 A1 | 6/1991 |
| EP | 0040000 | 11/1981 |
| EP | 0052963 | 6/1982 |
| EP | 0061907 | 10/1982 |
| EP | 0063004 | 10/1982 |
| EP | 0066351 | 12/1982 |
| EP | 0068669 | 1/1983 |
| EP | 0070134 | 1/1983 |
| EP | 0082665 | 6/1983 |
| EP | 0089154 | 9/1983 |
| EP | 0091749 | 10/1983 |
| EP | 0095827 | 12/1983 |
| EP | 0099707 | 2/1984 |
| EP | 00102213 | 3/1984 |
| EP | 0171702 | 2/1986 |
| EP | 0196849 | 10/1986 |
| EP | 0211721 | 2/1987 |
| EP | 0236624 | 9/1987 |
| EP | 0328251 | 1/1989 |
| EP | 0345056 A2 | 6/1989 |
| EP | 0386920 | 9/1990 |
| EP | 0500443 A1 | 8/1992 |
| EP | 0611003 A1 | 2/1994 |
| EP | 0659737 A2 | 12/1994 |
| EP | 0642787 A2 | 3/1995 |
| EP | 0687472 A2 | 12/1995 |
| EP | 0714663 A2 | 6/1996 |
| GB | 1391828 | 4/1975 |
| GB | 1532380 | 11/1978 |
| GB | 1549945 | 8/1979 |
| GB | 1571231 | 7/1980 |
| WO | 0436435 A1 | 7/1991 |
| WO | 0455006 A2 | 11/1991 |
| WO | WO92/18461 | 10/1992 |
| WO | 0565317 A1 | 10/1993 |
| WO | WO93/22277 | 11/1993 |
| WO | WO94/02493 | 2/1994 |
| WO | WO94/03425 | 2/1994 |
| WO | WO94/29290 | 12/1994 |
| WO | WO9429290 | 12/1994 |
| WO | WO95/01170 | 1/1995 |
| WO | WO95/04047 | 2/1995 |
| WO | WO96/04234 A1 | 2/1996 |
| WO | WO96/04234 | 2/1998 |

OTHER PUBLICATIONS

Bürgisser, et al. "Alternative Explanation for the Apparent Two Step Binding Kinetics of High-Affinity Racemic Antagonist Radioligands" Molecular Pharmacology 19:509-512 (1981).

Marinetti, et al. "Beta-Adrenergic Receptors of Human Leukocytes" Biochemical Pharmacology 32(13):2033-2043 (1983).

Howe, et al. "Selective β3-adrenergic agonists of brown adipose tissue and thermogenesis" Chemical Abstracts 117: 40209r (1992).

Jimenez, et al. "1-Thymoxy-2-propanolamines" Chemical Abstracts 86:29468v (1977).

Izquierdo Sanjose, et al., "Morpholine derivative and its salts" Chemical Abstracts 90:186971d (1979).

G. Neugebauer and P. Neubert, Metabolism and Pharmacokinetcs 16(4):257-260 (1991).

S.L. Heald, et al. "Synthesis of Iodine-125 labeled 14-(4-Azidobenzyl) Carazolol: A Potent Beta Adrenergic Photoaffinity Probe" J. Med. Chem. 26(6):832-838 (1983).

R.G.L. Shorr, et al. "The Beta-Adrenergic Receptor: Rapid Purification and Covalent Labeling by Photoaffinity Crosslinking" Proc. Natl. Acad. Sci. USA 79:2778-2782 (1982).

B. Ehmer, et al. "Influence of Carvedilol on Blood Glucose and Glycohaemoglobin A1 in Non-Insulin Dependent Diabetes" Drugs 36(6): 136-140 (1988).

* cited by examiner

SELECTIVE β₃ ADRENERGIC AGONISTS

This application is a continuation claiming the benefit under 35 U.S.C. §120 of U.S. Pat. No. 6,686,372, application Ser. No. 10/120,302, filed Apr. 10, 2002 which is a continuation claiming the benefit under 35 U.S.C. §120 of U.S. Pat. No. 6,413,991, application Ser. No. 09/610,096, filed Jun. 30, 2000, which is a division claiming the benefit under 35 U.S.C. §121 of U.S. Pat. No. 6,140,352, application Ser. No. 09/068,192, filed May 4, 1998, which claims the benefit under 35 U.S.C. §365(c) of PCT application No. US97/15230, filed Aug. 28, 1997, which claims the benefit under 35 U.S.C. §119(c) of U.S. Provisional Application No. 60/025,818, filed Sep. 5, 1996 and U.S. Provisional Application No. 60/029,228, filed Oct. 30, 1996.

FIELD OF INVENTION

The present invention is in the field of medicine, particularly in the treatment of Type II diabetes and obesity. More specifically, the present invention relates to selective β₃ adrenergic receptor agonists useful in the treatment of Type II diabetes and obesity.

BACKGROUND OF THE INVENTION

The current preferred treatment for Type II, non-insulin dependent diabetes as well as obesity is diet and exercise, with a view toward weight reduction and improved insulin sensitivity. Patient compliance, however, is usually poor. There are no currently approved medications that adequately treat either Type II diabetes or obesity. The invention described herein is directed toward an effective and timely treatment for these serious diseases.

One therapeutic opportunity that has been recently recognized involves the relationship between adrenergic receptor stimulation, anti-hyperglycemic effects, and metabolic events such as increased basil metabolic rate. Compounds that act as β₃ adrenergic receptor agonists have been shown to exhibit a marked effect on lipolysis, thermogenesis, and serum glucose levels in animal models of Type II (non-insulin dependent) diabetes.

The β₃ receptor, which is found in several types of human tissue including human fat tissue, has roughly 50% homology to the β₁ and β₂ receptor subtypes yet is considerably less abundant. The importance of the β₃ receptor is a relatively recent discovery since the amino-acid sequence of the human receptor was only elucidated in the late 1980's. A large number of publications have appeared in recent years reporting success in discovery of agents that stimulate the β₃ receptor. Despite these recent developments there remains a need to develop a selective β₃ receptor agonist which has minimal agonist activity against the β₁ and β₂ receptors.

The present invention provides methods of treating Type II diabetes, treating obesity, and stimulating the β₃ receptor. In addition, the present invention also provides novel compounds that are selective β₃ receptor agonists and as such are useful for treating Type II diabetes, obesity, and stimulating the β₃ receptor. U.S. Pat. No. 4,503,067 discloses carbazolyl-(4)-oxypropanolamine compounds, some of which are within the scope of formula I, as β-adrenoceptor antagonists and vasodilators.

SUMMARY OF THE INVENTION

The present invention provides methods of treating Type II diabetes, treating obesity, and stimulating the β₃ receptor which comprise administering to a patient in need thereof a compound described in Formula I below.

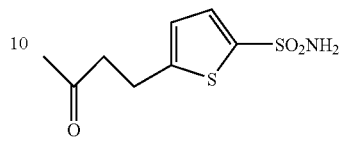

wherein:
$X_1$ is —OCH₂—, —SCH₂—, or a bond;
$X_2$ is a bond, or a 1 to 5 carbon straight or branched alkylene;
$X_3$ is O, S, or a bond;
$R_1$ is a fused heterocycle of the formula:

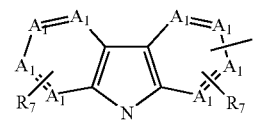

the $A_1$ groups are independently carbon or nitrogen, provided that no more than 2 nitrogens may be contained in either fused 6 membered ring and those 2 nitrogens may not be adjacent;
$R_2$ is independently hydrogen, $C_1$–$C_4$ alkyl, or aryl;
$R_3$ is hydrogen or $C_1$–$C_4$ alkyl;
$R_4$ is an optionally substituted heterocycle or a moiety selected from the group consisting of:

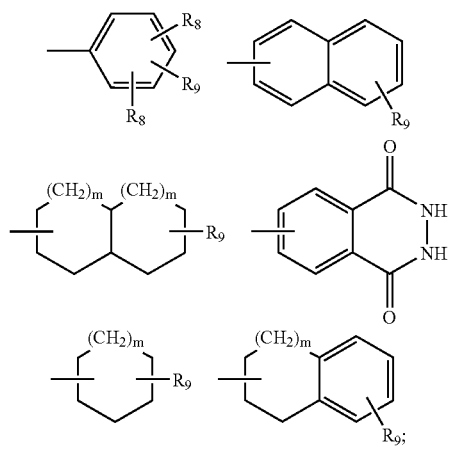

$R_5$ is hydrogen or $C_1$–$C_4$ alkyl;
$R_6$ is hydrogen, $C_1$–$C_4$ alkyl, or $CO_2(C_1$–$C_4$ alkyl);
or $R_5$ and $R_6$ combine with the carbon to which each is attached to form a $C_3$–$C_6$ cycloalkyl;
or $R_6$ combines with $X_2$ and the carbon to which each is attached to form a $C_3$–$C_8$ cycloalkyl;
or $R_6$ combines with $X_2$, $R_4$, and the carbon to which each is attached to form:

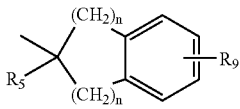

provided that $R_5$ is hydrogen;

$R_7$ is independently hydrogen, halo, hydroxy, $OR_2$, $C_1$–$C_4$ alkyl, $C_1$–$C_4$ haloalkyl, aryl, $COOR_2$, $CONR_2R_2$, $NHCOR_2$, $C_1$–$C_4$ alkoxy, $NHR_2$, $SR_2$, CN, $SO_2R_2$, $SO_2NHR_2$, or $SOR_2$;

$R_8$ is independently hydrogen, halo, or $C_1$–$C_4$ alkyl;

$R_9$ is hydrogen, halo, hydroxy, CN, $OR_{10}$, $C_1$–$C_4$ alkyl, $C_1$–$C_4$ haloalkyl, $CO_2R_2$, $CONR_{11}R_{12}$, $CONH(C_1$–$C_4$ alkyl or $C_1$–$C_4$ alkoxy), $SR_2$, $CSNR_2$, $CSNR_{11}R_{12}$, $NR_2SO_2R_2$, $SO_2R_2$, $SO_2NR_{11}R_{12}$, $SOR_2$, $NR_{11}R_{12}$, optionally substituted aryl, optionally substituted heterocycle, or $C_2$–$C_4$ alkenyl substituted with CN, $CO_2R_2$ or $CONR_{11}R_{12}$;

$R_{10}$ is $C_1$–$C_4$ alkyl, $C_1$–$C_4$ haloalkyl, $(CH_2)_nC_3$–$C_8$ cycloalkyl, $(CH_2)_n$aryl, $(CH_2)_n$heterocycle, $(CH_2)_nC_3$–$C_8$ optionally substituted cycloalkyl, $(CH_2)_n$ optionally substituted aryl, $(CH_2)_n$ optionally substituted heterocycle, or $(CH_2)_nCO_2R_2$;

$R_{11}$ and $R_{12}$ are independently hydrogen, $C_1$–$C_4$ alkyl, aryl, $(CH_2)_n$aryl, or combine with the nitrogen to which each is bound to form morpholinyl, piperidinyl, pyrrolidinyl, or piperazinyl;

m is 0 or 1; and n is independently 0, 1, 2, or 3;

or a pharmaceutically acceptable salt thereof.

Another embodiment of the present invention is the genus of novel compounds defined by Formula II below.

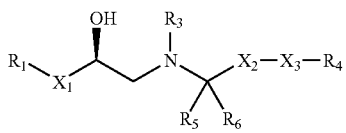
(II)

wherein:

$X_1$ is —$OCH_2$—, —$SCH_2$—, or a bond;

$X_3$ is O, S, or a bond;

$R_1$ is a fused heterocycle of the formula:

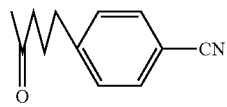

the $A_1$ groups of said heterocycle are independently carbon or nitrogen, provided that no more than 2 nitrogens may be contained in either fused 6 membered ring and those 2 nitrogens may not be adjacent;

$R_2$ is independently hydrogen, $C_1$–$C_4$ alkyl, or aryl;

$R_3$ is hydrogen or $C_1$–$C_4$ alkyl;

$R_4$ is an optionally substituted heterocycle or a moiety selected from the group consisting of:

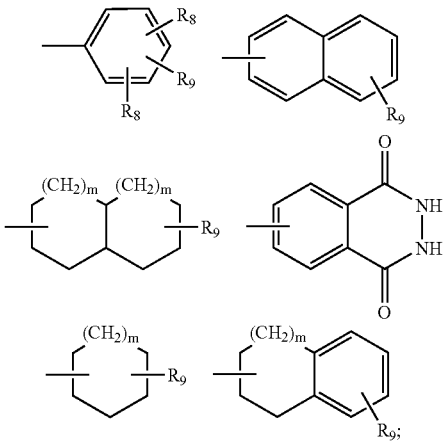

$X_2$ is a bond, or a 1 to 5 carbon straight or branched alkylene;

$R_5$ is hydrogen or $C_1$–$C_4$ alkyl;

$R_6$ is hydrogen, $C_1$–$C_4$ alkyl, or $CO_2(C_1$–$C_4$ alkyl);

or $R_5$ and $R_6$ combine with the carbon to which each is attached to form a $C_3$–$C_6$ cycloalkyl;

or $R_6$ combines with $X_2$ and the carbon to which each is attached to form a $C_3$–$C_8$ cycloalkyl;

or $R_6$ combines with $X_2$, $R_4$, and the carbon to which each is attached to form:

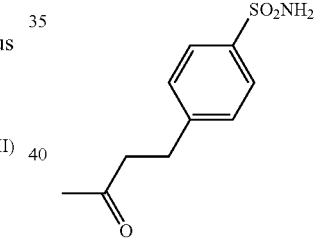

provided that $R_5$ is hydrogen;

$R_7$ is independently hydrogen, halo, hydroxy, $OR_2$, $C_1$–$C_4$ alkyl, $C_1$–$C_4$ haloalkyl, aryl, $COOR_2$, $CONHR_2$, $NHCOR_2$, $C_1$–$C_4$ alkoxy, $NHR_2$, $SR_2$, CN, $SO_2R_2$, $SO_2NHR_2$, or $SOR_2$;

$R_8$ is independently hydrogen, halo or $C_1$–$C_4$ alkyl;

$R_9$ is halo, CN, $OR_{10}$, $C_1$–$C_4$ alkyl, $C_1$–$C_4$ haloalkyl, $CO_2R_2$, $CONR_{11}R_{12}$, $CONH(C_1$–$C_4$ alkyl or $C_1$–$C_4$ alkoxy), $SR_2$, $CSNR_2$, $CSNR_{11}R_{12}$, $NR_2SO_2R_2$, $SO_2R_2$, $SO_2NR_{11}R_{12}$, $SOR_2$, $NR_{11}R_{12}$, optionally substituted aryl, optionally substituted heterocycle, or $C_2$–$C_4$ alkenyl substituted with CN, $CO_2R_2$ or $CONR_{11}R_{12}$;

$R_{10}$ is $C_1$–$C_4$ alkyl, $C_1$–$C_4$ haloalkyl, $(CH_2)_nC_3$–$C_8$ cycloalkyl, $(CH_2)_n$aryl, $(CH_2)_n$heterocycle, $(CH_2)_nC_3$–$C_8$ optionally substituted cycloalkyl, $(CH_2)_n$ optionally substituted aryl, $(CH_2)_n$ optionally substituted heterocycle, or $(CH_2)_nCO_2R_2$;

$R_{11}$ and $R_{12}$ are independently hydrogen, $C_1$–$C_4$ alkyl, aryl, $(CH_2)_n$aryl, or combine with the nitrogen to which each is bound to form morpholinyl, piperidinyl, pyrrolidinyl, or piperazinyl;

m is 0 or 1;

n is independently 0, 1, 2, or 3;

provided:
  when $R_5$ or $R_6$ is hydrogen; either
  1) one or more $A_1$ must be nitrogen, or
  2) $R_9$ is CN, $OR_{10}$, $CO_2R_2$, $CSNR_2$, $CSNR_{11}R_{12}$, $NR_2SO_2R_2$, $SO_2NR_{11}R_{12}$, optionally substituted aryl, optionally substituted heterocycle, or $C_2$–$C_4$ alkenyl substituted with CN, $CO_2R_2$ or $CONR_{11}R_{12}$; and
  $R_{10}$ is $C_1$–$C_4$ haloalkyl, $(CH_2)_nC_3$–$C_8$ cycloalkyl, $(CH_2)_n$heterocycle, $(CH_2)_nC_3$–$C_8$ optionally substituted cycloalkyl, $(CH_2)_n$ optionally substituted aryl, or $(CH_2)_n$ optionally substituted heterocycle;

or a pharmaceutically acceptable salt thereof.

The present invention also provides novel processes for making, as well as novel pharmaceutical formulations of the compounds of Formula II.

The compounds of Formula I are selective $\beta_3$ receptor agonists and as such are useful for treating Type II diabetes and obesity, as well as useful for stimulating or activating the $\beta_3$ receptor. Therefore, the present invention also provides for methods of treating Type II diabetes and obesity, as well as a method of stimulating or activating the $\beta_3$ receptor.

In addition, the present invention provides the use of compounds of Formulas I for treating Type II diabetes and obesity as well the use of compounds of Formulas I for stimulating or activating the $\beta_3$ receptor.

In addition, compounds of Formula I can be used to prepare a medicament useful for the treatment of Type II diabetes, the treatment of obesity, and the stimulation or activation of the $\beta_3$ receptor.

DETAILED DESCRIPTION

For the purposes of the present invention, as disclosed and claimed herein, the following terms are defined below. As they relate to the present invention, the terms below may not be interpreted, individually or collectively, to describe chemical structures that are unstable or impossible to construct.

The term "halo" represents fluorine, chlorine, bromine, or iodine.

The term "$C_1$–$C_4$ alkyl" represents a cyclo, straight or branched chain alkyl group having from one to four carbon atoms such as methyl, ethyl, n-propyl, isopropyl, cyclopropyl, n-butyl, isobutyl, sec-butyl, t-butyl and the like. A "haloalkyl" is one such alkyl substituted with one or more halo atoms, preferably one to three halo atoms. An example of a haloalkyl is trifluoromethyl. An "alkoxy" is a alkyl group covalently bonded by an —O— linkage.

The term "1 to 5 carbon straight or branched alkylene" represents a one to five carbon, straight or branched, alkylene moiety. A branched alkylene may have one or more points of branching. A 1 to 5 carbon straight or branched alkylene may optionally be unsaturated at one or more carbons. Thus, a 1 to 5 carbon straight or branched alkylene includes 1 to 5 carbon alkylene, alkenylene and alkylidene moieties. Examples include methylene, ethylene, propylene, butylene, —CH(CH$_3$)CH$_2$—CH(C$_2$H$_5$)CH$_2$—, —CH(CH$_3$) CH(CH$_3$)—, —CH$_2$C(CH$_3$)$_2$—, —CH$_2$CH(CH$_3$)CH$_2$—, —C(CH$_3$)$_2$CH=, —CH=CHCH$_2$—, —CH=CH—, and the like.

The "acyl" moiety, alone or in combination, is derived from an alkanoic acid containing from one to seven carbon atoms. The term "acyl" also includes moieties derived from an aryl carboxylic acid.

The term "aryl" represents an optionally substituted or unsubstituted phenyl or naphthyl. The term $(CH_2)_n$aryl is preferably benzyl or phenyl.

The term "optionally substituted" or "substituted" as used herein means an optional substitution of one to three, preferably one or two groups independently selected from halo, $C_1$–$C_4$ haloalkyl, hydroxy, carboxy, tetrazolyl, acyl, $COOR_2$, $CONR_{11}R_{12}$, $CONH(C_1$–$C_4$ alkoxy), cyano, $C_1$–$C_4$ alkoxy, $C_1$–$C_4$ alkyl, phenyl, benzyl, nitro, $NR_{11}R_{12}$, NHCO ($C_1$–$C_4$ alkyl), NHCO(benzyl), NHCO(phenyl), $SR_2$, $S(C_1$–$C_4$ alkyl), $OCO(C_1$–$C_4$ alkyl), $SO_2(NR_{11}R_{12})$, $SO_2$ ($C_1$–$C_4$ alkyl), or $SO_2$(phenyl).

$R_2$ is independently hydrogen, $C_1$–$C_4$ alkyl, or aryl.

$R_{11}$ and $R_{12}$ are independently H, $C_1$–$C_4$ alkyl, or combine with the nitrogen to which each is bound to form morpholinyl, piperidinyl, pyrrolidinyl, or piperazinyl.

The term "heterocycle" represents a stable, optionally substituted or unsubstituted, saturated or unsaturated 5 or 6 membered ring, said ring having from one to four heteroatoms that are the same or different and that are selected from the group consisting of sulfur, oxygen, and nitrogen; and when heterocycle contains two adjacent carbon atoms, the adjacent carbon atoms may be structured to form a group of the formula —CH=CH—; provided that (1) when the heterocyclic ring contains 5 members, the heteroatoms comprise not more than two sulfur or two oxygen atoms but not both; and (2) when the heterocyclic ring contains 6 members and is aromatic, sulfur and oxygen are not present. The heterocycle may be attached at any carbon or nitrogen which affords a stable structure. The heterocycle may be optionally substituted. Examples of a heterocycle include but are not limited to pyrazole, pyrazoline, imidazole, isoxazole, triazole, tetrazole, oxazole, 1,3-dioxolone, thiazole, oxadiazole, thiadiazole, pyridine, pyrimidine, piperazine, morpholine, pyrazine, pyrrolidine, piperidine, oxazolidone, oxazolidinedione, imidazolidinone, and the like.

The term "leaving group" as used in the specification is understood by those skilled in the art. Generally, a leaving group is any group or atom that enhances the electrophilicity of the atom to which it is attached for displacement. Preferred leaving groups are p-nitrobenzene sulfonate, triflate, mesylate, tosylate, imidate, chloride, bromide, and iodide.

The term "pharmaceutically effective amount", as used herein, represents an amount of a compound of the invention that is capable of stimulating the $\beta_3$ receptor in mammals. The particular dose of the compound administered according to this invention will, of course, be determined by the particular circumstances surrounding the patient, including the compound administered, the route of administration, the particular condition being treated, and similar considerations.

The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The term "treating," as used herein, describes the management and care of a patient for the purpose of combating the disease, condition, or disorder and includes the administration of a compound of present invention to prevent the onset of the symptoms or complications, to alleviate the symptoms or complications, or to eliminate the disease, condition, or disorder.

The term "selective" means preferential agonism or stimulation of the $\beta_3$ receptor over agonism of the $\beta_1$ or $\beta_2$ receptor. In general, the compounds demonstrate a minimum of a twenty fold differential (preferably over a 50× differential) in the dosage required to behave as an agonist to the $\beta_3$ receptor and the dosage required for equal agonism of the $\beta_1$ and $\beta_2$ receptors as measured in the Functional Agonist Assay. The compounds demonstrate this differential across the range of doses. Thus, $\beta_3$ selective compounds behave as agonists for the $\beta_3$ receptor at much lower concentrations with lower toxicity by virtue of their minimal agonism of the other receptors.

The term "stimulating", as used herein, means affecting, activating, or agonizing the $\beta_3$ receptor to elicit a pharmacological response. The stimulation or activation of the receptor may be either complete or partial relative to a known stimulating agent such as isoproterenol.

As previously noted, the present invention provides a method of treating type II diabetes and obesity, comprising administering to a mammal in need thereof compounds of the Formula I.

Preferred embodiments of the present invention are set out in paragraphs below.

(a) $R_1$ is

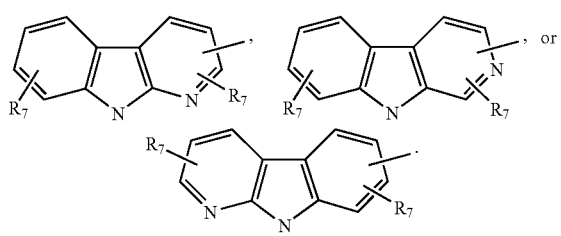

(b) $R_1$ is

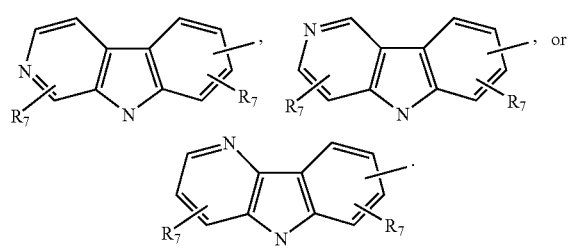

(c) $R_1$ is

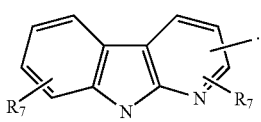

(d) $R_1$ is

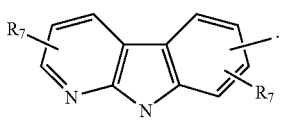

(e) $R_1$ is

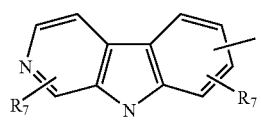

(f) $R_1$ is

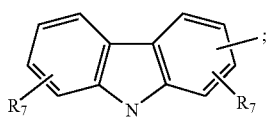

(g) $R_1$ is

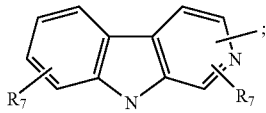

(h) $R_1$ is attached to $X_1$ in the 4 position.

(i) $R_1$ is

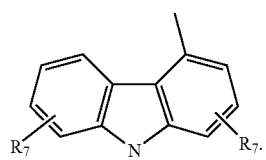

(j) $R_1$ is

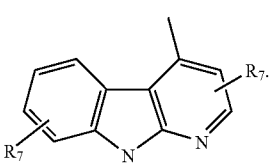

(k) $R_1$ is

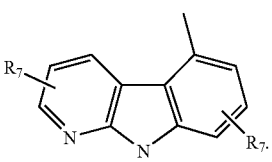

(l) $R_1$ is

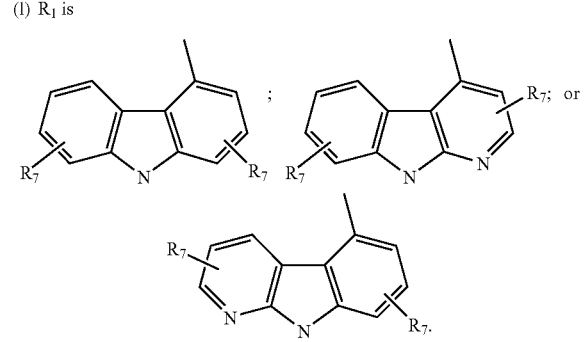

(m) $X_1$ is —OCH$_2$—, the oxygen of which is attached to $R_1$.
(n) $X_1$ is a bond.
(o) $R_3$ is methyl.
(p) $R_3$ is hydrogen.
(q) $R_5$ is methyl or ethyl.
(r) $R_6$ is methyl or ethyl.
(s) $R_5$ and $R_6$ are both methyl.
(t) $R_5$ and $R_6$ are both hydrogen.
(u) $X_2$ is isopropylene, methylene, or ethylene.
(v) $X_2$ is isopropylene
(w) $X_2$ is methylene.
(x) $X_2$ is ethylene.
(y) $R_4$ is

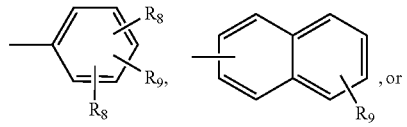

(z) R$_4$ is

[structure: (CH$_2$)$_m$-phenyl with R$_9$]

[structures: phenyl with R$_8$, R$_9$; naphthyl with R$_9$, or]

[structure: phthalazine-1,4-dione]

(ab) R$_4$ is

[structure: phenyl with R$_8$, R$_9$, R$_8$]

(ac) R$_4$ is

[structure: naphthyl with R$_9$]

(ad) R$_8$ is halo.
(ae) R$_8$ is hydrogen.
(af) R$_9$ is halo, CN, OR$_{10}$, C$_1$–C$_4$ alkyl, CO$_2$R$_2$, CONR$_{11}$R$_{12}$, CONH(C$_1$–C$_4$ alkyl or C$_1$–C$_4$ alkoxy), NR$_2$SO$_2$R$_2$, SO$_2$R$_2$, SO$_2$NR$_{11}$R$_{12}$, SOR$_2$, optionally substituted aryl, optionally substituted heterocycle.
(ag) R$_9$ is CO$_2$R$_2$, CONR$_{11}$R$_{12}$, CONH(C$_1$–C$_4$ alkyl or C$_1$–C$_4$ alkoxy), NR$_2$SO$_2$R$_2$, SO$_2$R$_2$, SO$_2$NR$_{11}$R$_{12}$, optionally substituted aryl, optionally substituted heterocycle, or C$_2$–C$_4$ alkenyl substituted with CN, CO$_2$R$_2$ or CONR$_{11}$R$_{12}$.
(ah) R$_9$ is halo, CN, C$_1$–C$_4$ haloalkyl, SR$_2$, CSNR$_2$, CSNR$_{11}$R$_{12}$, SO$_2$R$_2$, SO$_2$NR$_{11}$R$_{12}$, SOR$_2$, optionally substituted aryl, optionally substituted heterocycle, or C$_2$–C$_4$ alkenyl substituted with CN, CO$_2$R$_2$ or CONR$_{11}$R$_{12}$.
(ai) R$_9$ is OR$_{10}$, optionally substituted aryl, optionally substituted heterocycle, or C$_2$–C$_4$ alkenyl substituted with CN, CO$_2$R$_2$ or CONR$_{11}$R$_{12}$.
(aj) R$_9$ is NR$_2$SO$_2$R$_2$.
(ak) R$_9$ is CN.
(al) R$_9$ is CONR$_{11}$R$_{12}$.
(am) R$_9$ is OR$_{10}$.
(an) R$_{10}$ is (CH$_2$)$_n$C$_3$–C$_8$ cycloalkyl, (CH$_2$)$_n$aryl, (CH$_2$)$_n$heterocycle, said aryl, C$_3$–C$_8$ cycloalkyl, or heterocycle being optionally substituted.
(ao) R$_{10}$ is (CH$_2$)$_n$C$_3$–C$_8$ cycloalkyl, (CH$_2$)$_n$heterocycle, said C$_3$–C$_8$ cycloalkyl, or heterocycle being optionally substituted.
(ap) R$_{10}$ is (CH$_2$)$_n$heterocycle said heterocycle being unsubstituted or optionally substituted.
(aq) R$_{10}$ is aryl.
(ar) R$_{10}$ is pyridyl.
(as) R$_{10}$ is aryl substituted with CONR$_{11}$R$_{12}$, CN, CO$_2$R$_2$, or NR$_2$SO$_2$R$_2$.
(at) R$_{10}$ is pyridyl substituted with CONR$_{11}$R$_{12}$, CN, CO$_2$R$_2$, or NR$_2$SO$_2$R$_2$.
(au) R$_{10}$ is aryl substituted with CONR$_{11}$R$_{12}$.
(av) R$_{10}$ is aryl substituted with CN.
(ax) R$_{10}$ is aryl substituted with CO$_2$R$_2$. (ay) R$_{10}$ is aryl substituted with NR$_2$SO$_2$R$_2$.
(az) R$_{10}$ is pyridyl substituted with CONR$_{11}$R$_{12}$.
(ba) R$_{10}$ is pyridyl substituted with CN.
(bb) R$_{10}$ is pyridyl substituted with CO$_2$R$_2$. (bc) R$_{10}$ is pyridyl substituted with NR$_2$SO$_2$R$_2$.
(bd) Preferred optional substitution is halo, C$_1$–C$_4$ haloalkyl, hydroxy, carboxy, tetrazolyl, acyl, COOR$_2$, CONR$_{11}$R$_{12}$, cyano, C$_1$–C$_4$ alkoxy, C$_1$–C$_4$ alkyl, phenyl, benzyl, nitro, NR$_{11}$R$_{12}$, NHCO(benzyl), SO$_2$(C$_1$–C$_4$ alkyl), or SO$_2$(phenyl).
(be) Other preferred optional substitution is halo, C$_1$–C$_4$ haloalkyl, hydroxy, carboxy, tetrazolyl, acyl, COOR$_2$, CONR$_{11}$R$_{12}$, cyano, C$_1$–C$_4$ alkoxy, C$_1$–C$_4$ alkyl, phenyl, nitro, or NR$_{11}$R$_{12}$.
(bf) Other preferred optional substitution is halo, hydroxy, carboxy, acyl, COOR$_2$, CONR$_{11}$R$_{12}$, cyano, C$_1$–C$_4$ alkoxy, C$_1$–C$_4$ alkyl, phenyl, or NR$_{11}$R$_{12}$.
(bg) Other preferred optional substitution is halo, hydroxy, acyl, C$_1$–C$_4$ alkoxy, C$_1$–C$_4$ alkyl, or phenyl.
(bh) Preferred halo groups include bromine, chlorine, or fluorine.
(bi) Other preferred halo groups include chlorine or fluorine.
(bj) Most preferred halo groups include fluorine.
(bk) R$_7$ is hydrogen
(bl) R$_7$ is halo, hydroxy, OR$_2$, C$_1$–C$_4$ alkyl, C$_1$–C$_4$ haloalkyl, aryl, COOR$_2$, CONR$_2$R$_2$, NHCOR$_2$, C$_1$–C$_4$ alkoxy, NHR$_2$, SR$_2$, CN, SO$_2$R$_2$, SO$_2$NHR$_2$, or SOR$_2$.
(bm) R$_7$ is halo, hydroxy, OR$_2$, C$_1$–C$_4$ alkyl, or C$_1$–C$_4$ alkoxy.

Especially preferred compounds include the following:

[chemical structure of carbazole-oxy-propanol-amine-phenyl-pyridine carboxamide compound]

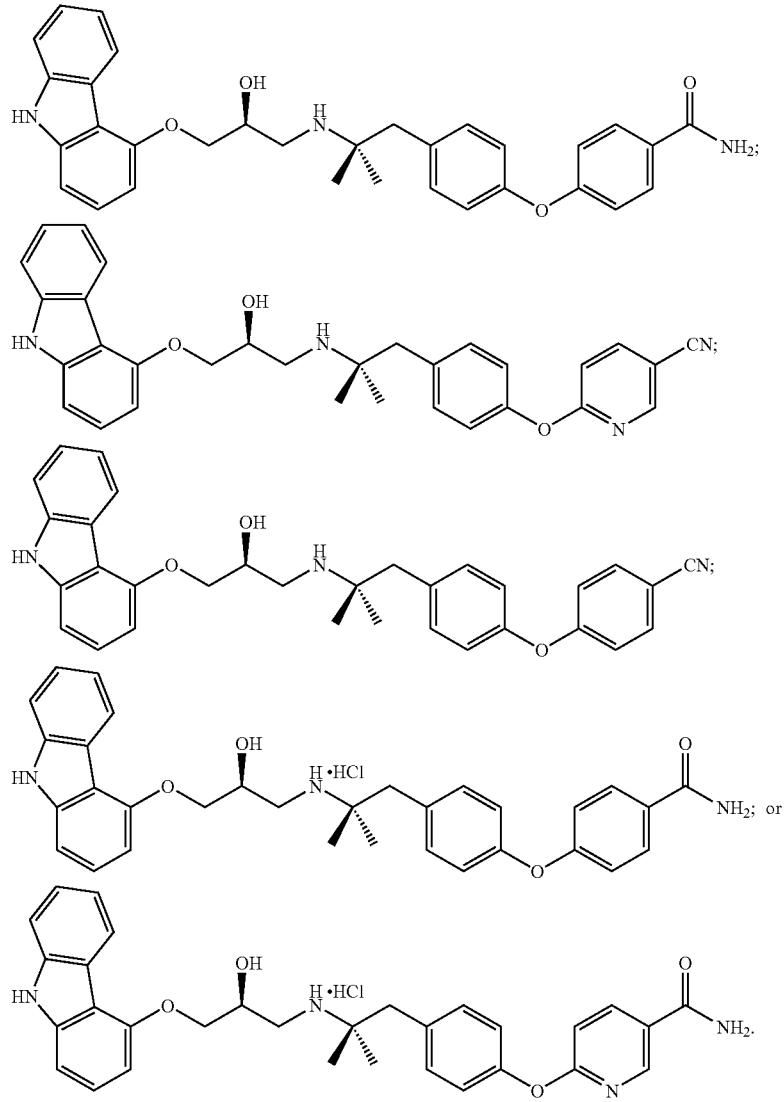

By virtue of their acidic moieties, some of the compounds of Formula I include the pharmaceutically acceptable base addition salts thereof. Such salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

Because of a basic moiety, some of the compounds of Formula I can also exist as pharmaceutically acceptable acid addition salts. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4 dioate, 3-hexyne-2,5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycollate, maleate, tartrate, methanesulfonate, propanesulfonate, naphthalene-1-sulfonate, naphthalene-2-sulfonate, mandelate and the like salts.

In addition, it is recognized that compounds of the present invention may for a variety of solvates with a number of different solvents. Representative solvates can be useful as final embodiments of the present invention or as intermediates in the isolation or preparation of the final embodiments of this invention. For example solvates can be prepared with lower alcohols such as ethanol and with alkyl esters such ethylacetate.

It is recognized that various stereoisomeric forms of the compounds of Formula I may exist. The compounds may be prepared as racemates and can be conveniently used as such. Therefore, the racemates, individual enantiomers, diastereomers, or mixtures thereof form part of the present invention. Unless otherwise specified, whenever a compound is described or referenced in this specification all the racemates, individual enantiomers, diastereomers, or mixtures thereof are included in said reference or description.

The compounds of Formula I can be prepared as described in the following Schemes and Examples. Schemes I and II describe methodology for the preparation of final embodiments of the present invention. Schemes III–VII represent methodology for the preparation of intermediates required for the construction of the final embodiments of the invention.

Scheme I

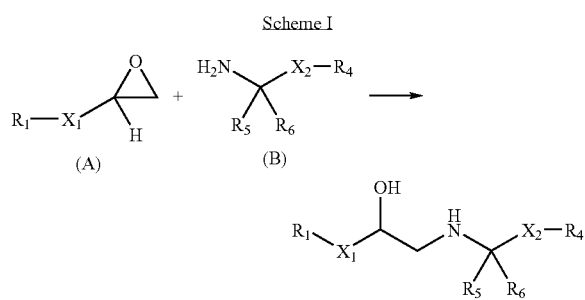

In Scheme I, $X_1$, $X_2$, $R_1$, $R_2$, $R_4$, $R_5$, and $R_6$ have the same meaning as previously described; and $X_3$ is a bond. The reaction of Scheme I is carried out under conditions appreciated in the art for the amination of epoxides. For example, the epoxide (A) may be combined with the amine (B) in an alcohol, such as ethanol, at room temperature to the reflux temperature of the reaction mixture. Preferably, the reaction is carried out under conditions generally described in Atkins et al., *Tetrahedron Lett*. 27:2451 (1986). These conditions include mixing the reagents in the presence of trimethylsilyl acetamide in a polar aprotic solvent such as acetonitrile, dimethylformamide (DMF), acetone, dimethylsulfoxide (DMSO), dioxane, diethylene glycol dimethyl ether (diglyme), tetrahydrofuran (THF), or other polar aprotic solvents in which the reagents are soluble. Preferably, the solvent is DMSO. The reaction is carried out at temperatures ranging from about 0° C. to reflux.

Expoxides utilized in scheme I can be prepared by methods well known in the art, or according to Scheme III from starting material known in the art.

Certain compounds of the present invention are prepared by a novel combinatorial/parallel synthesis. This synthesis is described in Scheme II.

Scheme II

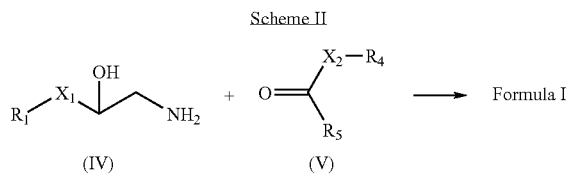

In Scheme II, $X_1$, $X_2$, $R_1$, $R_4$, and $R_5$ have the same meaning as previously described and $R_6$ is hydrogen. The reaction of Scheme II is preferably carried out by adding to a glass vial: a non-reactive solvent such as methanol, DMF, methylene chloride or acetonitrile, amine (IV), and ketone (V). The solution is shaken to allow for imine formation and treated with Amberlite IRA400 borohydride resin (Aldrich Chemicals). The slurry is then shaken an additional 24 hours to effect reduction to the secondary amine. Methylene chloride and polystyrene-linked benzaldehyde resin (Frechet, J. M. et al., *J. Am Chem. Soc*. 93:492 (1971)) is added to the vial, in order to scavenge excess primary amine starting material. The slurry is shaken, preferably overnight. The slurry is then filtered through a cotton plug, and the residual solids are rinsed with methanol. Evaporation under a flow of air, followed by drying for several hours at room temperature in a vacuum oven yields the desired product of sufficient purity.

Alternatively, compounds of formula (V) can be prepared by dissolving, in a vial, the amine and ketone in a non-reactive solvent or solvent mixture such as methanol, DMF, or the like. Acetic acid and sodium cyanoborohydride are then added. After being shaken for approximately 72 hours the reaction mixture is applied to an ionexchange column such as SCX. The column is flushed with solvent and the product was then eluted using a solution such as ammonia, in methanol. The solvent was evaporated, followed by drying in a vacuum oven to yield the secondary amine product.

A modification of Scheme II is necessary when the amine hydrochloride salt is used. Addition of resin-bound base to the initial reaction mixture prior to reduction or scavenging allows the desired reaction to proceed. Imine formation using amine hydrochloride salts, an aldehyde or ketone, and a resin bound amine base may be carried out using two different resins: poly(4-vinylpyridine), commercially available from Aldrich, and resin (VIII), synthesized by the reaction of Merrifield resin with piperidine (Scheme IIa):

Scheme IIa

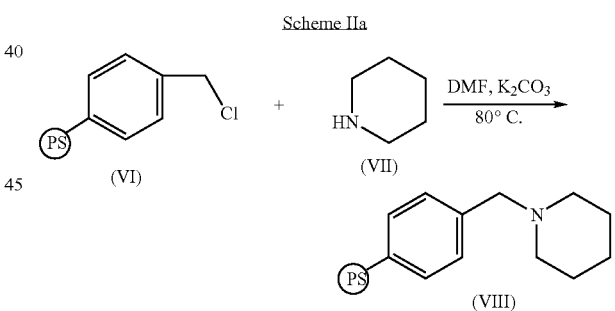

In Scheme IIa, PS is polysytrene. Both the poly(4-vinylpyridine) and resin (VIII) promote imine formation.

Scheme II can also be carried out by utilization of traditional techniques. Reductive aminations described in scheme II are well known in the art. They are typically performed by mixing the amine and ketone starting materials in a solvent and adding a reducing agent. Solvents typically include lower alcohols, DMF, and the like. A wide variety of reducing agents can be utilized, most commonly utilized are sodium borohydride and sodium cyanoborohydride. The reaction is typically performed at room temperature to the reflux temperature of the solvent. Products are isolated by techniques well known in the art.

The ketone and amino starting materials of Scheme II can be prepared by techniques recognized and appreciated by one skilled in the art. The synthesis of the starting materials is generally described in Schemes III and VII.

Scheme III

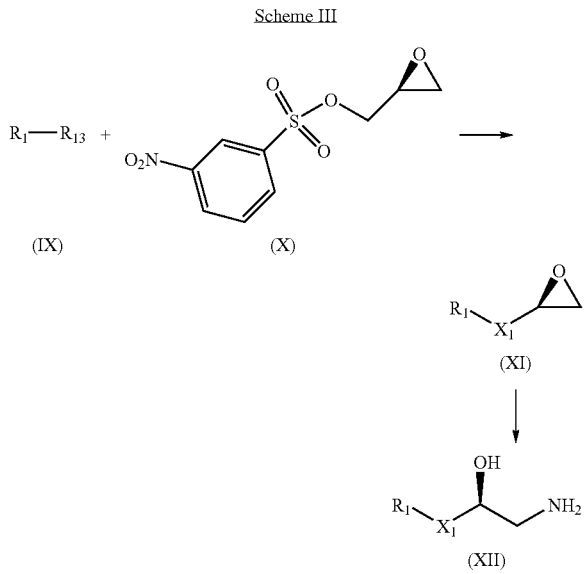

In Scheme III, $R_1$ is the same as previously defined. $R_{13}$ is OH or SH. Equimolar amounts of the aromatic compound (Compound IX) and (2S)-(+)-glycidyl 3-nitrobenzene-sulfonate (Compound X) are dissolved in an inert solvent such as acetone or DMF and treated with about 1.1 equivalents of a non-reactive acid scavenger, such as $K_2CO_3$. The suspension is then heated at reflux for 16–20 hours with stirring. The solvent is removed in vacuo. The residue is partitioned between chloroform or other organic solvent and water. The organic layer is dried over $Na_2SO_4$ and concentrated in vacuo to give the compound (XI) in sufficient purity (>95%) and yield (85–100%).

The epoxide (XI) is dissolved in an alcohol, preferably methanol, and treated with one equivalent of dibenzylamine. The solution is preferably stirred at reflux for three to four hours and then cooled to ambient temperature. Approximately 10 equivalents of ammonium formate are added to the flask, followed by 10% palladium on carbon, and the suspension stirred vigorously at reflux for 30–45 minutes. The reaction mixture is then filtered through Celite, concentrated in vacuo to a minimum volume and treated with 1.1 equivalents of a 1.0 M anhydrous solution of HCl in ether. The solution is concentrated to dryness. The solid residue is triturated with pentane to yield products of sufficient purity (>97%) and yield (60–100%). If desired, further purification may be carried out by passing over a short plug of silica, eluting with $CHCl_3$, then 95:5 $CHCl_3/MeOH$, then 25:5:1 $CHCl_3/MeOH/NH_4OH$.

Alternatively, the epoxide (XI) is treated with a solution of methanol saturated with ammonia gas and stirred at room temperature in a sealed tube for 16 hours. This solution is then evaporated, and the residue subjected to standard purifications such as column chromatography or recrystallization. The HCl salt is then optionally produced by the addition of HCl gas in ether.

The ketone moieties of Scheme II, that are either unknown in the art or not commercially available, can be prepared in accordance with Scheme IV.

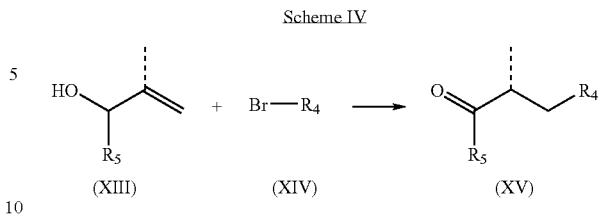

In Scheme IV, $R_4$ and $R_5$ are the same as previously defined. The notation - - - indicates optional branching. Preferably, $R_4$ is a substituted phenyl. The reaction described in Scheme IV is referred to as a Heck reaction and is described in A. J. Chalk et al., *J. Org. Chem.* 41: 1206 (1976). The reaction is achieved by treating compound (XIII) with an arylpalladium reagent. The arylpalladium reagent is generated in situ by treating Compound (XIV) with a palladium-triarylphosphine complex. The reaction is generally carried out under conditions appreciated in the art.

Additional amines, of the type where $X_2$ is methylene, $R_4$ is aryl, and $R_{10}$ is aryl, heterocycle, optionally substituted aryl, or optionally substituted heterocycle, that are reacted in a manner analogous to Scheme I can be prepared in accordance with Scheme V.

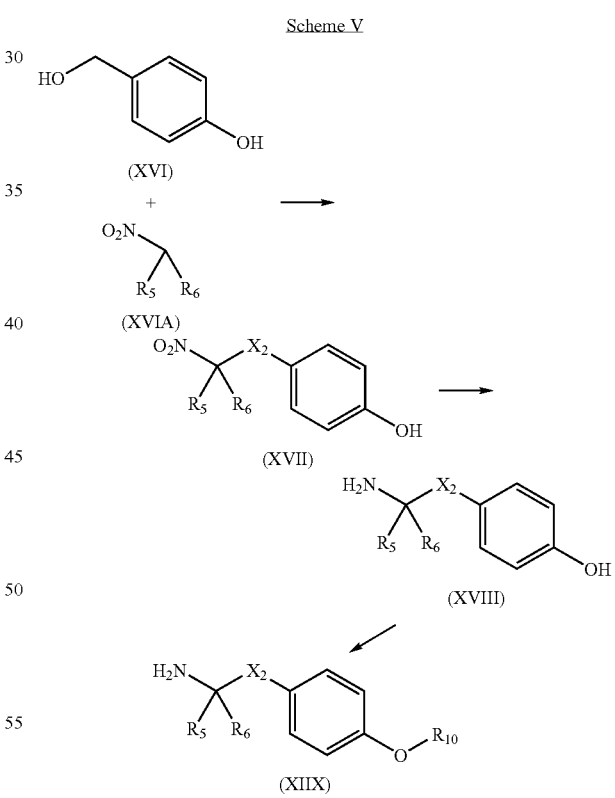

$R_5$, $R_6$, and $R_{10}$ are as previously defined and $X_2$ is methylene. Compounds of the formula (XVII) can be prepared by reacting 4-hydroxybenzyl alcohol with excess (5 mol/equiv) of a compound of formula (XVIA) by methods well known in the art. (see Sh. Prikl. Kin., Vol 45, 1573–77 (1972); Russ.) The reaction can also be carried out by mixing the reagents in an aprotic solvent, preferably diglyme, and adding potassium t-butoxide (0.5 mol/equiv.). The reaction is then heated to reflux and water removed. After removal of water is complete, generally 2–8 hours depending upon the scale of the reaction, the resulting solution is subjected to aqueous workup including acidic washes and the product is isolated by crystallization. Compound (XVII) can be reduced by methods well known in the art. Compound (XVIII) is preferably prepared by hydrogenation of the corresponding compound (XVII) over a precious metal catalyst. The hydrogenation can be affected at between 20 and 60 psi of hydrogen, and with a variety of solvents, temperatures, and catalysts well known in the art. The reaction is preferably carried out at 50 psi of hydrogen over 5% palladium on carbon wetted with 2B3 ethanol. Compound (XVII) is charged to the reactor along with one equivalent of acetic acid, diluted with methanol, heated to 50° C., and subjected to hydrogen for 5–24 hours depending on the scale of the reaction. The product is isolated as the acetic acid salt upon work up by methods well known in the art.

A skilled artisan would appreciate that compound (XVIII) could be coupled with a wide variety of aromatic halides to yield the claimed ethers. The coupling can be carried out according to procedures well known in the art and is preferably performed by mixing the starting materials in N,N-dimethylacetamide and toluene in the presence of potassium carbonate. The reaction is then heated to reflux for 5 to 24 hours and water removed. The product is typically isolated by aqueous work up after rotory evaporation of the reaction solvent. The crude product can be purified by methods well know in the art. A skilled artisan would appreciate that the amines prepared by Scheme V can be utilized in Scheme I to prepare compounds of the present invention.

Other amines used to construct final embodiments of the present invention can be prepared according to scheme VI.

Scheme VI

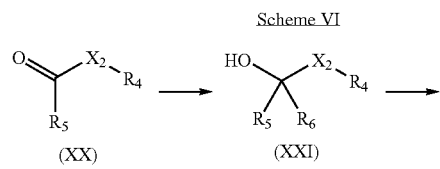

(XX) (XXI)

-continued

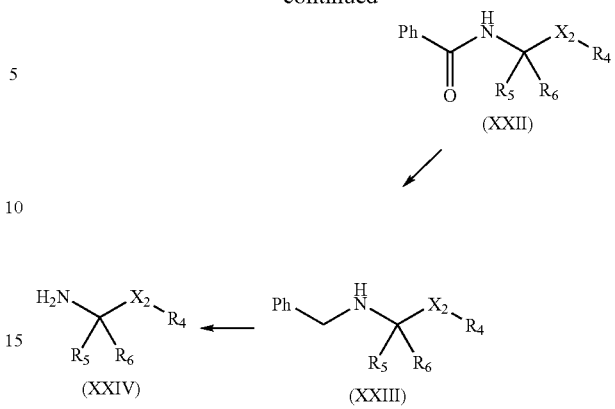

Compounds of formula (XXI) can be prepared by the addition of a nucleophile, of the formula $R_6$-M, wherein M is a metal or metal salt, to the compounds of formula (XX) according to procedures well known in the art. The skilled artisan would appreciate a wide variety of conditions amenable to performing the additions. Preferred nucleophiles include, but are not intended to be limited to, alkyl grignard reagents, alkyl lithium reagents, and the like.

Compounds of formula (XXII) can be prepared from the compounds of formula (XXI) by the Ritter reaction. (See *Organic Reactions*, Vol. 17, pp. 213–325, (1979)).

Compounds of formula (XXIII) can be prepared by reduction of the compounds of formula (XXII) according to procedures well known in the art. Preferred reducing agents include, but are not intended to be limited to, borane complexes and the like.

Compounds of formula (XXIV) can be prepared by reduction of the compounds of formula (XXIII) according to procedures well known in the art. (See Greene T. W., *Protective Groups in Organic Synthesis*, John Wiley and Sons, (1981)).

Other amines used to construct final embodiments of the present invention can be prepared according to scheme VII, wherein J is a protecting group.

Scheme VII

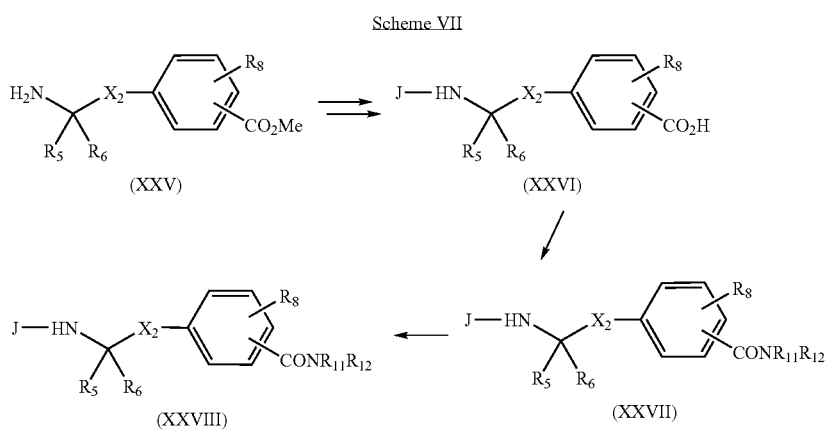

The compounds of formula (XXVI) can be prepared from the amino esters of formula (XXV) by methods well known in the art. (see, Greene supra).

The amides of formula (XXVII) can be prepared from the N-protected amino acids of formula (XXVI) by methods well known in the art. For example, any number of peptide coupling procedures will affect the desired reaction. (see March, Advanced Organic Chemistry, 3 ed.)

The deprotection of the compounds of formula (XXVII) can be accomplished by methods well known in the art. (see, Greene supra).

Scheme VIII

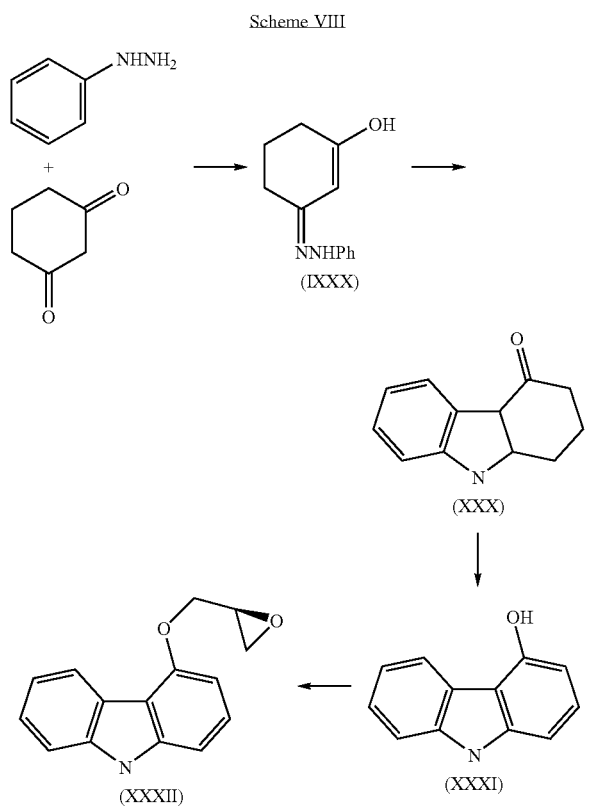

Compound (IXXX) can be prepared by the addition of phenyl hydrazine to 1,3-cyclohexanedione by methods known in the art. For example, phenylhydrazine or it salt can be dissolved in water and cyclohexanedione added. The addition is preferably carried out in a dropwise fashion at room temperature. Other methods of addition and temperatures, however, would be operable. After stirring for 4–24 hours, the resulting precipitate can be collected by filtration and purified by methods known in the art.

Compound (XXX) can be prepared by the cyclization of compounds of formula (IXXX) by methods known in the art. For example, the transformation can be affected by heating the compound of formula (IXXX) in the presence of an acid such as phosphoric acid, sulfuric acid, trifluoracetic acid, and the like. While the reaction can be affected at lower temperatures, the reaction is preferably performed at about 90° C., for about 1–2 hours, in neat phosphoric acid.

Dehydrogenation of the compound of formula (XXX) yield 4-hydroxycarbazole can be accomplished by methods well known in the art. For example, the compound of formula (XXX) can be reacted with rainey-nickel, copper bromide, or palladium on carbon. The preferred conditions include stirring with 5% or 10% palladium on carbon in cymene and dodecene. The skilled artisan would appreciate that such a transformation can be performed at a range of temperatures, the progress of which is typically monitored by TLC or other analytical techniques.

Compound of formula (XXXII) can be prepared from 4-hydroxycarbazole by methods well known in the art. For example, equimolar amounts of the 4-hydroxycarbazole and (2S)-(+)-glycidyl 3-nitrobenzenesulfonate can be dissolved in an inert solvent such as acetone and treated with 1.1 equivalents of a non-reactive acid scavenger, such as potassium carbonate or cesium carbonate. The suspension is then heated at reflux for about 16–20 hours with stirring. The solvent can be removed in vacuo. The residue is partitioned between chloroform or other organic solvent and water. The organic layer can be dried over $Na_2SO_4$ and concentrated in vacuo to give the compound (XI) in sufficient purity (>95%) and yield (85–100%).

Alternatively, 4-hydroxycarbazole can be reacted with epichlorohydrin, by methods known in the art and the resulting product can be closed to the epoxide compound of formula (XXXII) by methods well known in the art.

Starting materials for the compounds described in Schemes I–VIII, as well as starting materials for the Preparations and Examples included herein, are either commercially available, known in the art, or can be prepared by methods known in the art or described herein.

Another embodiment of the present invention is a process of preparing novel compounds of the formula IA;

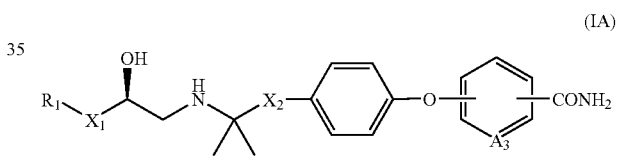

(IA)

wherein:

$A_3$ is CH or N;

which comprises:

in step 1, hydrolysis of a compound of the formula IB;

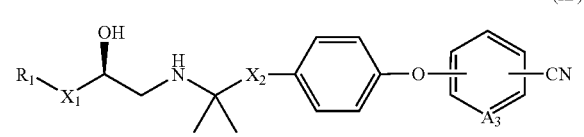

(IB)

and, optionally, in step 2, reacting the product of step 1 with an acid to form an acid addition salt.

Step one of the process can be carried out by a variety of agents known in the art. It is, however, preferably affected by utilization of one of the following agents: polyphosphoric acid, $H_2O_2$ and $K_2CO_3$ in dimethylsulfoxide, $H_2O_2$ and ammonium hydroxide, $H_2O_2$ and sodium hydroxide, potassium hydroxide and t-butanol, or water and mineral or organic acid. Step 2 of the process involves addition of an agent capable of forming an acid addition salt with the product of step 1. Step 2 can be carried out by numerous methods known in the art involving addition of mineral acid, or other acid, to a solution of the product of step 1. Additionally, the product of step one could be purified prior to step 2 and the present invention contemplates such an optional purification step.

Another embodiment of the present invention is a process of preparing a compound of Formula I which comprises:

In step 1, reacting an epoxide of the formula XI:

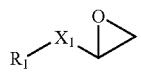

(XI)

with an amine of formula (B):

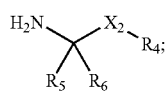

(B)

and optionally in step 2, reacting the product of step 1 with an acid to form an acid addition salt.

The process can be carried out by a variety of agents known in the art or described herein, it is however preferably affected by reacting the amine and epoxide in a solvent at elevated temperature. Preferred solvents include: lower alcohols, dimethylformamide, dimethylsulfoxide, acetone and the like. The reaction is generally performed at a temperature ranging from ambient to the reflux temperature of the solvent. Most preferably, it is done in ethanol at 40–60° C. Step 2 can be carried out by numerous methods known in the art involving addition of mineral acid, or other acid, to a solution of the product of step 1. Additionally, the product of step one could be purified prior to step 2 and the present invention contemplates such an optional purification step.

PREPARATIONS OF THE EXAMPLES

The following examples and preparations are provided merely to further illustrate the invention. The scope of the invention is not construed as merely consisting of the following examples. In the following examples and preparations, melting point, nuclear magnetic resonance spectra, mass spectra, high pressure liquid chromatography over silica gel, gas chromatography, N,N-dimethylformamide, palladium on charcoal, tetrahydrofuran, ethyl acetate, thin layer chromatography and elemental analysis are abbreviated M.Pt., NMR, MS, HPLC, GC, DMF, Pd/C, THF, EtOAc, TLC and EA respectively. The terms "EA", "TLC", "NMR", and "MS", when being utilized in the preparations, indicate that the data indicated was consistent with the desired structure.

Preparations 1 through 24 describe syntheses of compounds utilized in combinatorial scheme II.

Preparation 1

4-(3-Oxobutyl)-1-(2-oxazolidinyl)benzene

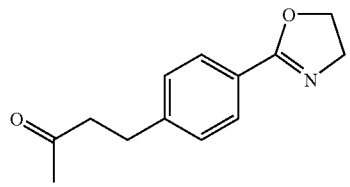

4-Bromo-1-(2-oxazolidine)benzene (3.0 g, 13.3 mmol), 3-buten-2-ol (1.4 g, 20 mmol), Pd(OAc)$_2$ (60 mg, 0.26 mmol), (o-tolyl)$_3$P (158 mg, 0.52 mmol), sodium bicarbonate (1.34 g, 15.9 mmol) in 30 mL of N-methylpyrrolidinone were heated under nitrogen at 130° C. for 1 hour. The reaction mixture was then cooled and partitioned between ethyl acetate and water. The combined organic layers were washed with water and then dried (Na$_2$SO$_4$), filtered, and concentrated in vacuo to yield 2.6 g of a tan oil. Purification by flash chromatography (silica gel, 1:1 ethyl acetate/hexane) yielded 1.9 g of a pale yellow oil which crystallized upon drying under vacuum. Recrystallization from hexane gave 1.47 g (49%) of white needles, m.p. 62–64° C. NMR. MS.

Preparation 2

4-[4-(3-Oxobutyl)phenoxy]benzonitrile

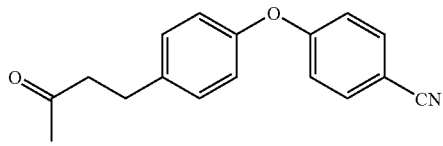

4-Fluorobenzonitrile (6.05 g, 50 mmol), 4-(4-hydroxyphenyl)-2-butanone (8.21 g, 50 mmol) and potassium carbonate (8.3 g, 60 mmol) were dissolved in N,N-dimethylacetamide (50 mL) and heated at 150° C. for 4 hours under nitrogen. The reaction mixture was then poured into 800 mL of ice water. A slowly crystallizing solid was filtered to give 13 g of crude product. This material was recrystallized from ethanol/water (3:1) to give 10.48 g (79%) of pale brown crystals, m.p. 64–66° C. EA. NMR. MS.

Preparation 3

[4-(3-Oxobutyl)phenoxy]benzamide

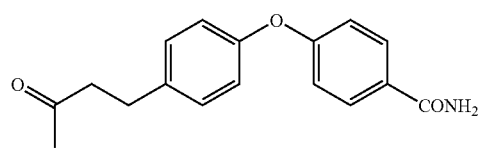

4-[4-(3-Oxobutyl)phenoxy]benzonitrile (6.0 g, 22.6 mmol) and potassium carbonate (1.0 g, 7.2 mmol) were slurried in DMSO (50 mL) and cooled to 0° C. in an ice bath. Aqueous 30% hydrogen peroxide (6 mL) was added slowly, and the mixture stirred at 0° C. for 1 hour. The reaction was quenched by pouring into 500 mL water, and the subsequent white precipitate was collected and washed with water. This material was recrystallized from 300 mL ethanol to give 5.35 g (84%) white crystals, m.p. 169–172° C. NMR. MS. EA.

Preparation 4

2-Triphenylmethyl-5-chloromethyltetrazole

5-Chloromethyltetrazole (1.19 g, 10 mmol) in $CH_2Cl_2$ (10 mL) was treated with triphenylmethyl chloride (2.79 g, 10 mmol) and diisopropylethylamine (2.0 mL, 11.5 mmol) and stirred for 40 minutes at room temperature. The reaction mixture was concentrated in vacuo and partitioned between ethyl acetate/water. The organic layer was washed with saturated $NaHCO_3$ solution, then brine, dried ($Na_2SO_4$) and concentrated in vacuo to yield 3.48 g of an off-white solid. Trituration of this residue in diethyl ether yielded 3.04 g (84%) of a white solid, m.p.162–165° C. NMR. MS. EA.

Preparation 5

5-[4-(2-Oxobutyl)phenoxymethyl]tetrazole

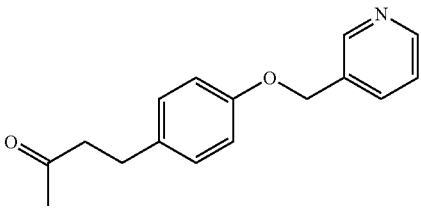

4-(4-Hydroxyphenyl)-2-butanone (493 mg, 3 mmol) was cooled to 5° C. and treated with NaH (180 mg, 4.5 mmol, 60% in mineral oil) under nitrogen. After 15 minutes the ice bath was removed and the solution allowed to warm to room temperature over 45 minutes. The reaction was cooled to 5° C. and treated with 2-triphenylmethyl-5-chloromethyltetrazole (1.08 g, 3 mmol) and stirred at room temperature for 3 hours. The reaction mixture was poured into EtOAc (300 mL), and washed with water then brine. The organic layer was dried (MgSO₄) and concentrated in vacuo to provide a yellow solid. This material was suspended in a mixture of MeOH (100 mL) and THF (50 mL) and treated with 4N HCl in dioxane (7.5 mL, 30 mmol). The resulting mixture was stirred for 1.5 hr. and then concentrated in vacuo to provide a tan solid. The residue was applied to a silica chromatography column and eluted with 33–100% ethyl acetate in hexane to provide 235 mg (32%) of a white solid, m.p.148–150° C. NMR. MS. EA.

Preparation 6

3-[4-(2-Oxobutyl)phenoxymethyl]pyridine

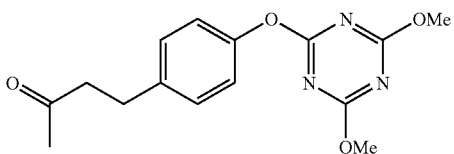

4-(4-Hydroxyphenyl)-2-butanone (4.11 g, 25 mmol) and potassium carbonate (10.37 g, 75 mmol) in acetone (30 mL) was treated with 3-picolyl chloride hydrochloride (4.27 g, 26 mmol) under nitrogen. The mixture was stirred at reflux for 21 hours, proceeding about 50% towards completion. Potassium iodide (2.0 g, 13 mmol, 0.5 eq) was added and after 3 hours no picolyl chloride was observed on TLC. The volatiles were removed in vacuo and the resulting residue partitioned between EtOAc/water. The combined organic layers were washed with water, saturated $NaHCO_3$ solution, 10% $Na_2SO_3$, and then brine. The organic layer was dried (MgSO₄) and concentrated in vacuo to provide 4.8 g of a yellow oil. The material was purified on a Waters Prep 2000LC by elution with 10–80% ethyl acetate in hexanes over 45 minutes to yield 2.20 g (34%) of an oil which solidified on standing, m.p. 35–37° C. NMR. MS. EA.

Preparation 7

2,6-Dimethoxy-4-[4-(2-oxobutyl)phenoxy]-1,3,5-triazine 4-(4-Hydroxyphenyl)-2-butanone (4.93 g, 30 mmol) was added to a solution of sodium methoxide (1.62 g, 30 mmol) in methanol (150 mL) under nitrogen. After stirring for 1 hour the methanol was removed in vacuo and the residue suspended in acetone (200 mL). The suspension was treated with 4,6-dimethoxy-2-chlorotriazine and refluxed for 3 hours. The volatiles were removed in vacuo and the residue partitioned between ethyl acetate/water. The organic layers were dried (MgSO₄) and concentrated in vacuo to provide 10.28 g of a white semi-solid. The material was purified on a Waters Prep 2000LC by elution with a gradient of 20–60% ethyl acetate in hexanes over 55 minutes to yield 4.43 g (49%) of a colorless oil. NMR. MS. EA.

Preparation 8

2-[4-(2-Oxobutyl)phenoxy]-5-carboxamidopyridine

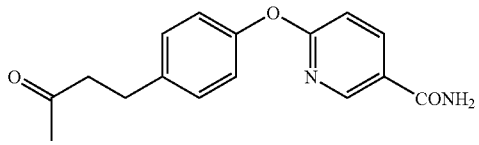

4-(4-Hydroxyphenyl)-2-butanone (3.28 g, 20 mmol) in anhydrous DMF (150 mL) was treated with NaH (1.2 g, 30 mmol, 60% in mineral oil) under nitrogen. The solution was stirred for 30 minutes at ambient temperature and then treated with 6-chloronicotinamide (3.13 g, 20 mmol). The reaction was stirred at 60° C. for 1.5 hours and then 90° C. for five hours. The reaction was allowed to cool, poured into 50% saturated ammonium chloride solution, and extracted with EtOAc. The organic layer was dried ($MgSO_4$) and concentrated in vacuo with a xylene azeotrope to yield 11.4 g of a brown oil. The material was purified on a Waters Prep 2000LC by elution with 75–100% EtOAc over 60 minutes. The resulting material was triturated in cold EtOAc and collected by filtration to provide 2.73 g (48%) white solid m.p. 137–139° C. EA. NMR. MS.

Preparation 9

2-[4-(2-Oxopropyl)phenoxy]-5-carboxamidopyridine

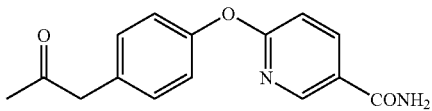

In a manner similar to the above examples, 3-(4-hydroxyphenyl)-2-propanone (2.25 g, 15 mmol) was treated with NaH (0.9 g, 22.5 mmol, 60% in mineral oil) followed by reaction with 6-chloronicotinamide (2.34 g, 15 mmol). Following workup the material was purified on a Waters Prep 2000LC to provide 1.28 g (32%) of a light yellow solid. m.p. 172–174° C. NMR. MS. EA.

Preparation 10

{4-[(2-Oxocyclohexyl)methyl]benzonitrile

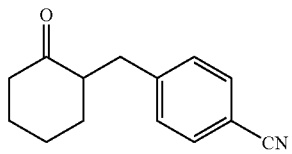

A mixture of methyl cyclohexanone-2-carboxylate (11.0 g, 70 mmol, from Fluka), α-bromo-p-toluunitrile (12.3 g, 63 mmol), potassium carbonate (10.5 g, 76 mmol) in THF (200 mL) was refluxed for 24 hours. The progress of the reaction was followed by GC. The reaction was diluted with water and the THF was removed under reduced pressure. The aqueous portion was extracted with EtOAc, dried ($MgSO_4$), and concentrated to give 19.3 g of a white solid that was 74% pure by gas chromatrophy. The solid was recrystallized from hexane/EtOAc to give 7.75 g white crystals that were 100% pure by glc. A second crop of 3.65 g was obtained by adding more hexane to the filtrate. Overall, 11.4 g (67%) of 1-[(4-cyanophenyl)methyl]-1-methoxycarbonyl-2-oxocyclohexane carboxylate, was obtained; mp 82–84° C. NMR. MS.

Under a blanket of nitrogen, a mixture of 1-[(4-cyanophenyl)methyl]-1-methoxycarbonyl-2-oxocyclohexane carboxylate (7.6 g, 28 mmol), sodium cyanide (2.1 g, 42 mmol) and DMSO (100 mL) was heated at 115° C. for 1.5 hours. The progress of the reaction was monitored by glc. The reaction was cooled and partitioned between water, EtOAc and brine. The organic layer was washed with water and dried ($MgSO_4$). After concentration, crude product was obtained as a tan oil. Purification by plug filtration (200 g silica gel, 15% EtOAc/hexane) gave 3.3 g (55%) product as colorless oil. NMR. MS.

Preparation 11

[(2-Oxocyclohexyl)methyl]benzamide

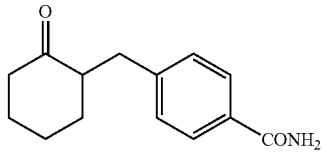

A DMSO (20 mL) solution of the compound of Preparation 28 (2.5 g, 11.7 mmol) was cooled in an ice bath. Solid $K_2CO_3$ (500 mg) was added followed immediately by 30% $H_2O_2$ (3 mL). After 20 minutes, TLC (3/7 EtOAc/hexane) showed a trace of starting material remained. The ice bath was removed and the reaction was stirred and room temperature for 1 hour. The reaction was diluted with 500 mL water and the white solid collected and dried to give 2.44 g (90%) desired amide. The product was recrystallized from 1/9 EtOAc/hexane to give 2.02 g of the titled product as white crystals, mp 167–170° C. NMR. MS.

Preparation 12

Tetralone-6-carboxylic acid, ethylene ketal

6-Bromo-2-tetralone (2.0 g, 8.89 mmol) was dissolved in toluene (50 mL) and treated with excess ethylene glycol (4.88 mL, 88.9 mmol) and catalytic p-toluenesulfonic acid (15 mg). The solution was stirred at reflux 16 hours, and water was removed from the reaction mixture using a Dean-Stark condenser. After cooling to ambient temperature, the toluene solution was washed 2×1N NaOH, 1× water, 1× brine, dried over $Na_2SO_4$ and concentrated in vacuo to give 2.23 g (93%) of 6-bromo-2-tetralone ethylene ketal as a brown oil which was used without further purification.

6-Bromo-2-tetralone ethylene ketal (2.2 g, 8.15 mmol) was dissolved in anhydrous THF (30 mL), cooled to −78° C. and treated with tert-butyllithium (12.05 mL, 20.4 mmol, 1.7M in pentane) under an atmosphere of nitrogen. After stirring for 30 minutes, anhydrous carbon dioxide gas was passed through the reaction mixture for 20 minutes at 78° C. The suspension was then allowed to warm to ambient temperature. The solution was quenched with water and acidified with 1N HCl, then extracted 2×EtOAc. The organic extracts were washed with brine, dried over $Na_2SO_4$ and concentrated in vacuo to a pale brown oil. The oily residue was applied to a silica flash chromatography column and eluted with 30%–50% EtOAC in hexanes to yield tetralone-6-carboxylic acid, ethylene ketal 1.06 g (55%) of a slowly crystallizing solid. NMR. MS.

Preparation 13

Tetralone-6-carboxamide

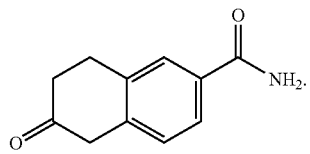

Tetralone-6-carboxylic acid, ethylene ketal (395 mg, 2.07 mmol) was codissolved in $CH_2Cl_2$ (50 mL) with N-hydroxysuccinimide (260 mg, 2.76 mmol) at 0° C. and treated with a slight excess of 1,3-dicyclohexylcarbodiimide (502 mg, 2.50 mmol). The mixture was allowed to warm to ambient temperature over 30 minutes, during which time a fine white precipitate formed. Ammonium chloride (333 mg, 6.23 mmol) and triethylamine (1.58 mL, 12.5 mmol, d=0.797) were added. The solution was stirred at ambient temperature for 16 hours. The suspended urea and salts were filtered away and the solution concentrated in vacuo to a colorless oil. The oil was applied to a silica flash chromatography column and eluted with 50–100% EtOAc in hexanes to yield 250 mg (64%) of 2-tetralone-6-carboxamide, ethylene ketal as a white solid, clean by NMR, TLC.

2-Tetralone-6-carboxamide ethylene ketal (250 mg, 1.07 mmol) and catalytic p-toluenesulfonic acid were stirred in acetone (50 mL) at ambient temperature for 48 hours. The volatiles were removed in vacuo and the residue triturated in ethyl acetate. The solids were filtered, washed and dried to yield 77.5 mg (38%) of 2-tetralone-6-carboxamide as a white powder, pure by NMR, TLC. MS.

Preparation 14

Tetralone-6-morpholinamide

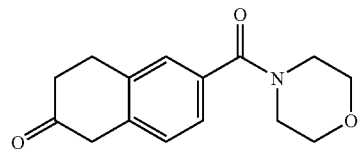

2-Tetralone-6-carboxylic acid, ethylene ketal (395 mg, 2.07 mmol) was co-dissolved in $CH_2Cl_2$ (50 mL) with N-hydroxysuccinimide (260 mg, 2.76 mmol) at 0° C. and treated with a slight excess of 1,3-dicyclohexylcarbodiimide (502 mg, 2.50 mmol). The mixture was allowed to warm to ambient temperature over 30 minutes, during which time a fine white precipitate formed. Morpholine (0.91 mL, 10.4 mmol, d=0.998) was added and the solution stirred at ambient temperature for 16 hours. The suspended urea was filtered away and the solution concentrated in vacuo to a colorless oil. The oil was applied to a silica flash chromatography column and eluted with 50–100% EtOAc in hexanes to yield 323 mg (51%) of 2-tetralone-6-morpholinamide, ethylene ketal as a slowly crystallizing solid, clean by NMR, TLC.

2-Tetralone-6-morpholinamide, ethylene ketal (323 mg, 1.06 mmol) and catalytic p-toluenesulfonic acid were stirred in acetone (50 mL) at ambient temperature for 48 hours. TLC indicated a mixture of 2-tetralone-6-morpholinamide, ethylene ketal and desired product, so the solution was heated to reflux for 16 hours. The volatiles were removed in vacuo and the residue applied to a silica flash chromatography column and eluted with 50–100% EtOAc in hexanes to yield 27 mg (10%) of 2-tetralone-6-morpholinamide a slowly crystallizing solid, pure by NMR, TLC. MS.

The following compounds were prepared in a manner analogous to schemes IV and/or preparations 1 through 14 described herein or by techniques appreciated in the art:

| Name | Structure | m.p. | Yld | NMR | MS |
|---|---|---|---|---|---|
| 4-(3-oxobutyl) benzonitrile Preparation 15 | 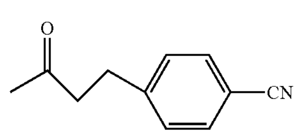 | oil | 33% | x | x |
| 3-(3-oxobutyl) benzonitrile Preparation 16 | 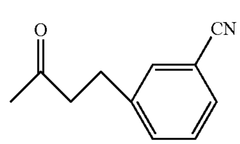 | oil | 44% | x | x |

-continued

| Name | Structure | m.p. | Yld | NMR | MS |
|---|---|---|---|---|---|
| 3-(3-oxobutyl)benzamide Preparation 17 | 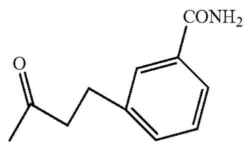 | 104–6 | 45% | x | x |
| 2-(3-oxobutyl)benzonitrile Preparation 18 | 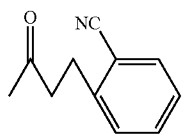 | oil | 43% | x | x |
| (2-(3-oxobutyl)benzamide Preparation 19 | 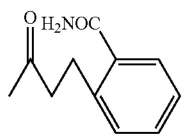 | 113–114 | 91% | x | x |
| 4-(3-oxohexyl)benzonitrile Preparation 20 | 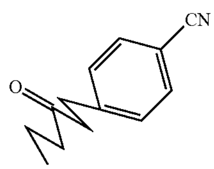 | oil | 85% | x | x |
| 4-(3-oxohexyl)benzamide Preparation 21 | 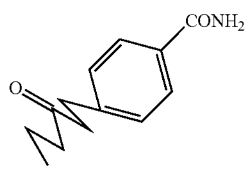 | 90–93 | 67% | x | x |
| 3-methyl-5-(4-(3-oxobutyl)phenyl)-1H-tetrazole Preparation 22 | 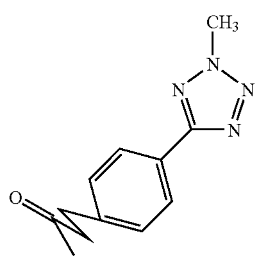 | 90–93 | 67% | x | x |
| (4-(3-oxobutyl)phenyl)sulfonamide Preparation 23 | 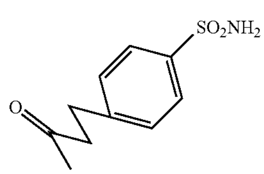 | 132–4 | 36% | x | x |
| 4-(1-methyl-3-oxobutyl)benzonitrile Preparation 24 | 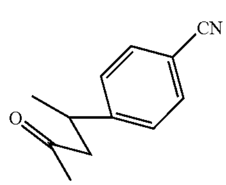 | oil | 44% | x | x |

-continued

| Name | Structure | m.p. | Yld | Data NMR | MS |
|---|---|---|---|---|---|
| 3-benzyl-5-(4-(3-oxobutyl)phenyl)-1H-tetrazole Preparation 25 | 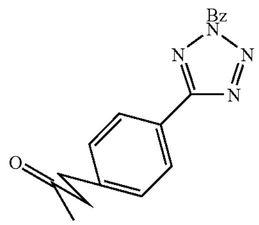 | 66–9 | 41% | x | x |
| 4-(1-methyl-3-oxobutyl)benzamide Preparation 26 | 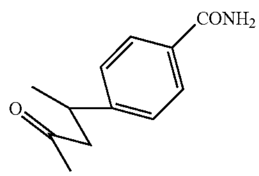 | 127–9 | 95% | x | x |
| 5-(4-(3-oxobutenyl)phenyl)-1H-tetrazole Preparation 27 | 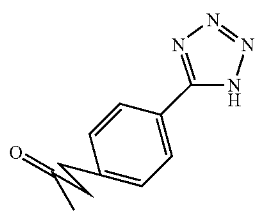 | 197–9 | 94% | x | x |
| 5-(3-oxobutyl)-2-furanoic acid Preparation 28 | 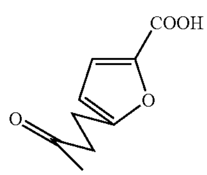 | 129–32 | 86% | x | x |
| 3-(2-fluoro-4-(3-oxobutyl)phenyl)propenoic acid Preparation 29 | 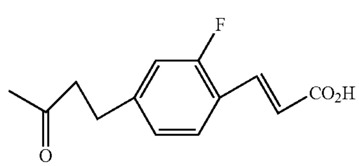 | 143–6 | 95% | x | x |
| 4-(3-oxobutyl-1-cyanomethylbenzene Preparation 30 | 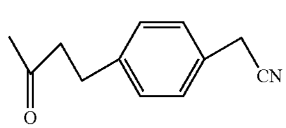 | oil | 100% | x | x |
| (4-(3-oxobutyl)phenyl)thioamide Preparation 31 | 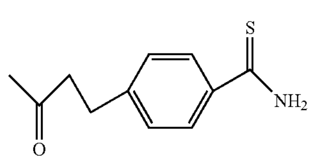 | 96–8 | low* | x | x |
| (2-fluoro-4-(3-oxobutyl)benzonitrile Preparation 32 | 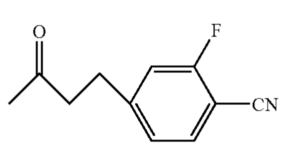 | oil | 78% | x | x |

-continued

| Name | Structure | m.p. | Yld | Data NMR | MS |
|---|---|---|---|---|---|
| 2-fluoro-4-(3-oxobutyl)benzamide Preparation 33 | 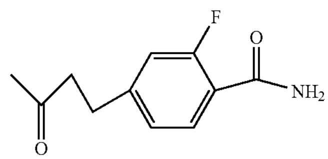 | 150–3 | 85% | x | x |
| 3-methyl-5-(2-(3-oxobutyl)phenyl-1N-tetrazole Preparation 34 | 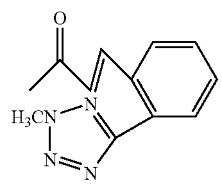 | 64–5 | 45% | x | x |
| 4-(3-oxocyclohexyl)benzonitrile Preparation 35 | 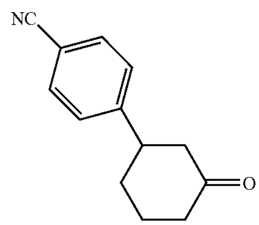 | 66–69 | 36% | x | x |
| 1-methyl-5-(2-(3-oxo-butenyl)phenyl)-1H-tetrazole Preparation 36 | 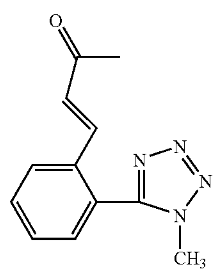 | 100–102 | 18% | x | x |
| (2,6-difluoro-(4-(3-oxobutyl)phenyl))sulfonamide Preparation 37 | 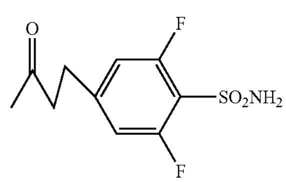 | oil | 41% | x | x |
| N-methoxyl-4-(3-oxobutyl)benzamide Preparation 38 | 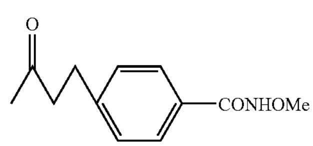 | | low | x | x |
| 4-(2-methyl-3-oxobutyl)benzonitrile Preparation 39 | 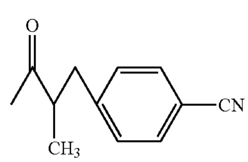 | oil | 66% | x | x |
| 4-(2-methyl-3-oxobutyl)benzamide Preparation 40 | 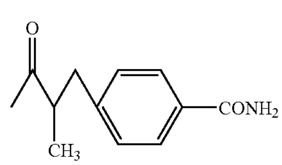 | 112–115 | 87% | x | x |

-continued

| Name | Structure | m.p. | Yld | Data NMR | MS |
|---|---|---|---|---|---|
| (1-methyl-2-(4-(3-oxobutyl)phenyl)-4-trifluoromethyl)imidazole Preparation 41 | 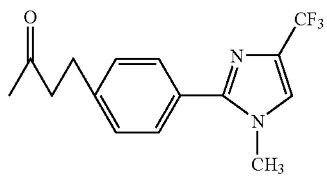 | 62–3 | 68% | x | x |
| 4-(1,2-dimethyl-3-oxobutyl)benzamide Preparation 42 | 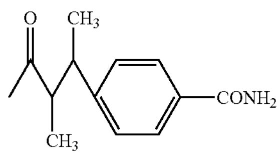 | 100–102 | 90% | x | x |
| 4-(3-oxocyclohexyl)benzamide Preparation 43 | 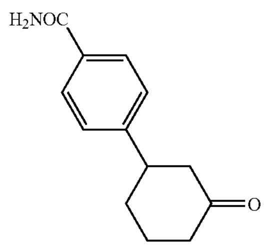 | 188–91 | 42% | x | x |
| 5-(3-oxobutyl)-2-thiophene sulfonamide Preparation 44 | 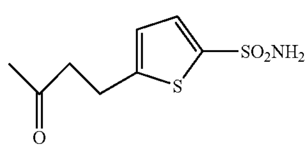 | 96–98 | 66% | x | x |
| (3-(3-oxobutyl)phenyl)sulfonamide Preparation 45 | 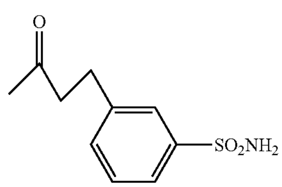 | 87–90 | 35% | x | x |
| 2-methyl-5-(3-(3-oxobutyl)phenoxy)phenyl)tetrazole Preparation 46 | 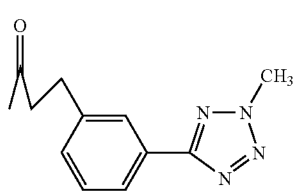 | 98 | 65% | x | x |
| 4-(3-oxocyclopentyl)benzamide Preparation 47 | 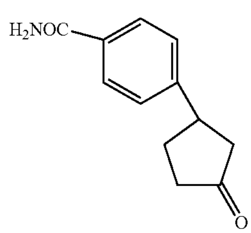 | 203–4 | 43% | x | x |

-continued

| Name | Structure | m.p. | Yld | NMR | MS |
|---|---|---|---|---|---|
| 4-(1,1-dimethyl-3-oxobutyl)benzamide Preparation 48 | 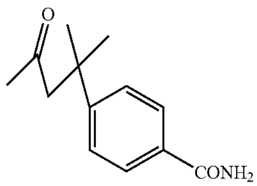 | 106–8 | 61% | x | x |
| 4-(3-oxocycloheptyl)benzonitrile Preparation 49 | 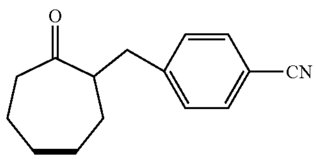 | oil | 54% | x | x |
| 4-(3-oxohexyl)benzonitrile Preparation 50 | 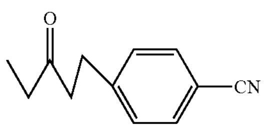 | oil | 77% | x | x |
| 4-(3-oxobutyl)-phthalhydrazide Preparation 51 | 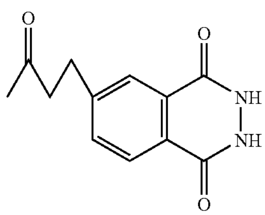 | 161–4 | 13% | x | x |
| 4-(3-oxohexyl)benzamide Preparation 52 | 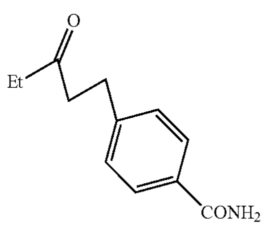 | 158–61 | 82% | x | x |
| 4-(2,2-dimethyl-3-oxobutyl)benzonitrile Preparation 53 | 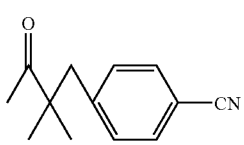 | oil | 72% | x | x |
| 4-(2,2-dimethyl-3-oxobutyl)benzamide Preparation 54 | 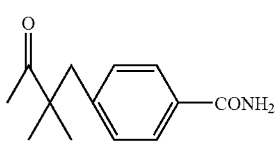 | 127–131 | 62% | x | x |
| 5-(2-methyl-3-oxobutyl)-2-thiophene sulfonamide Preparation 55 | 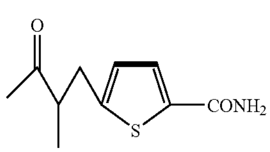 | oil | low | x | x |

-continued

| Name | Structure | m.p. | Yld | Data NMR | MS |
|---|---|---|---|---|---|
| 4-((2-oxocycloheptyl methyl)benzamide Preparation 56 | 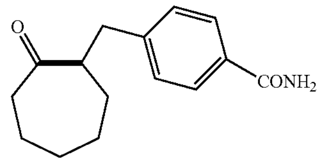 | 132–4 | 88% | x | x |
| 4-((2-oxocyclopentyl) benzonitrile Preparation 57 | 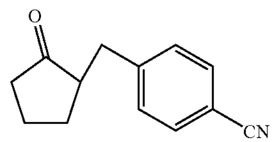 | oil | 62% | x | x |
| 4-((2-oxocyclopentyl) methyl)benzamide Preparation 58 | 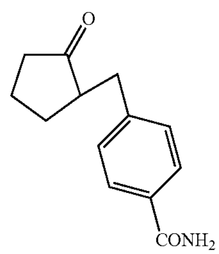 | 138–142 | 81% | x | x |
| 4-(4-(3-oxobutyl) phenoxy)benzonitrile Preparation 59 | 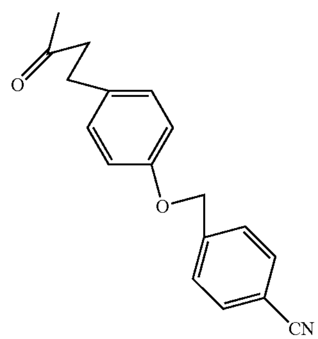 | 94–7 | 84% | x | x |
| 4-(4-(3-oxobutyl) phenoxy)methyl benzamide Preparation 60 | 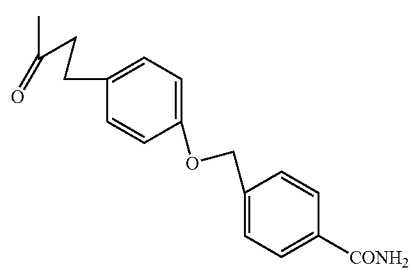 | 215–17 | 95% | x | x |
| 2-fluoro-4-(2-methyl-3-oxobutyl) benzonitrile Preparation 61 | 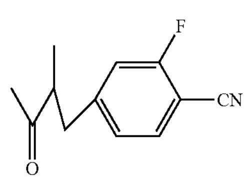 | oil | 42% | x | x |
| 2-fluoro-4-(2-methyl-3-oxobutyl)benzamide Preparation 62 | 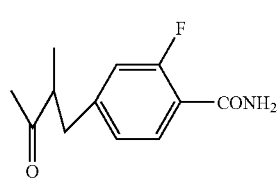 | 112–15 | 93% | x | x |

-continued

| Name | Structure | m.p. | Yld | NMR | MS |
|------|-----------|------|-----|-----|-----|
| 5-(2-fluoro-4-(2-methyl-3-oxobutyl)phenyl)-1H-tetrazole Preparation 63 | 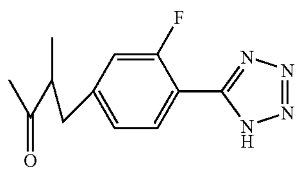 | 175–8 | 32% | x | x |
| 5-(3-oxobutyl)-2-(morpholinosulfonyl)-thiophene Preparation 64 | 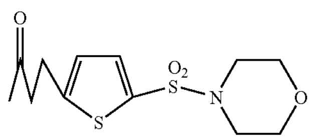 | 80–83 | 69% | x | x |
| 5-(2-methyl-3-oxobutyl)-2-(morpholinosulfonyl)-thiophene Preparation 65 | 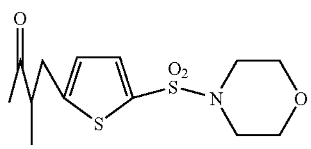 | oil | 15% | x | x |
| 4-(2-(4-(3-oxobutyl)phenoxy)ethyl)benzonitrile Preparation 66 | 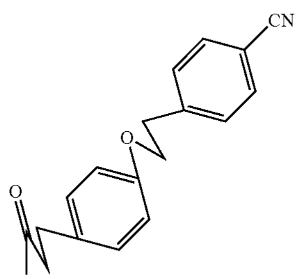 | oil | 41% | x | |
| 4-(4-(3-oxobutyl)phenyl)benzonitrile Preparation 67 | 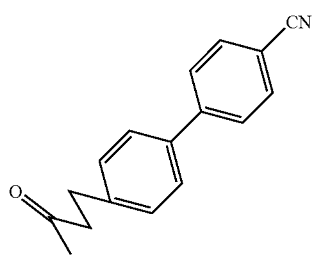 | 133–5 | 62% | x | x |
| 2-methyl-4-(3-oxobutyl)benzonitrile Preparation 68 | 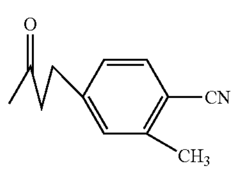 | oil | 55% | x | x |
| 4-(4-(3-oxobutyl)phenyl)benzamide Preparation 69 | 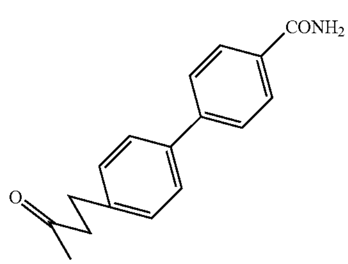 | 229–31 | 94% | x | x |

-continued

| Name | Structure | m.p. | Yld | NMR | MS |
|------|-----------|------|-----|-----|-----|
| (3-methyl-4-(3-oxobutyl)phenyl)methanenitrile Preparation 70 | 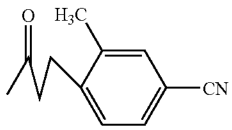 | 34–6 | 75% | x | x |
| 2-methyl-4-(3-oxobutyl)benzamide Preparation 71 | 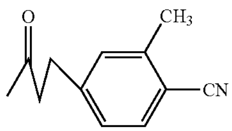 | 147–50 | 39% | x | x |
| 3-methyl-4-(3-oxobutyl)benzamide Preparation 72 | 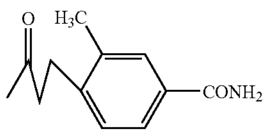 | 103–5 | 46% | x | x |
| 4-(2-(4-(3-oxobutyl)phenoxy)ethyl)benzamide Preparation 73 | 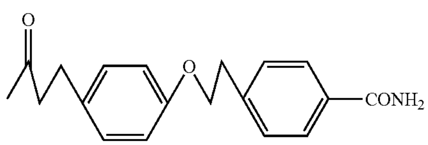 | semi-solid | 17% | x | x |
| 4-(4-oxopentyl)benzonitrile Preparation 74 | 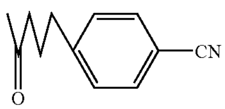 | oil | quant | x | x |
| 4-(4-oxopentyl)benzamide Preparation 75 | 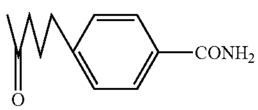 | 111–13 | 87% | x | x |
| 3-methyl-4-(2-methyl-3-oxobutyl)benzonitrile Preparation 76 | | oil | 64% | x | x |
| (3-methyl-4-(2-methyl-3-oxobutyl)benzamide Preparation 77 | 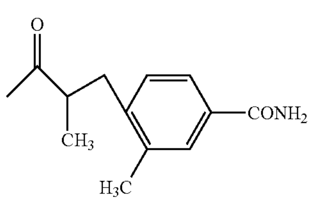 | 105–7 | 71% | x | x |
| 4-(2,5-dimethyl-4-(3-oxobutyl)phenoxy)benzonitrile Preparation 78 | 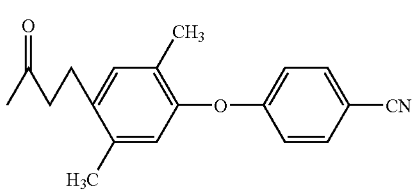 | 57–9 | low | x | x |

| Name | Structure | m.p. | Yld | NMR | MS |
|---|---|---|---|---|---|
| 4-(2-ethyl-3-oxobutyl)benzoic acid Preparation 79 | 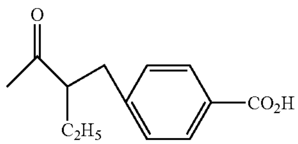 | 126–9 | 24% | x | x |
| 4-(2,5-dimethyl-(3-oxobutyl)phenoxy)benzamide Preparation 80 | 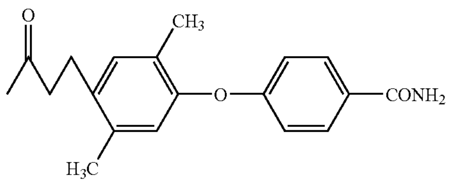 | 191–3 | 76% | x | x |
| (4-2,6-dimethyl-(3-oxobutyl)phenoxy)phenyl)methanenitrile Preparation 81 | 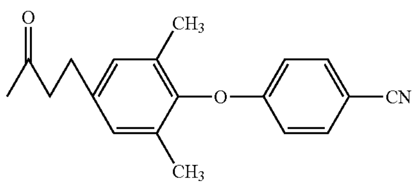 | yellow oil | 72% | x | x |
| 4-(2,6-dimethyl-(3-oxobutyl)phenoxy)benzamide Preparation 82 | 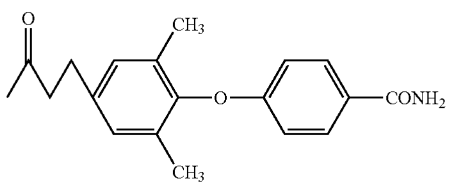 | 238–41 | 63% | x | x |

Preparation 83

4-(2-Methyl-2-nitropropyl)phenol

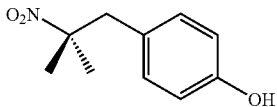

A mixture of 4-hydroxybenzyl alcohol (100.08 g, 806 mmol), 2-nitropropane (400 mL, 4.45 mol), and diglyme (800 mL) was heated to 38° C. Potassium t-butoxide (45.29 g, 403.6 mmol) was added, and the mixture was heated to reflux at 132° C. with a Dean-Stark trap. Water began collecting in the trap, and continued at a high rate for approximately 1.5 h. When water collection slowed (around 2.5 h) then aliquats of solvent (30–40 mL each) were removed every thirty minutes. During the water collection and solvent removal the temperature rose from 132° C. to 149° C. After 4 h less than 1% of the 4-hydroxybenzyl alcohol remained by HPLC analysis. The heating mantle was removed, and the reaction mixture was allowed to cool. When the temperature was 100° C. water (200 mL) was added, and the solution was allowed to cool to room temperature. The solvent was removed on a rotary evaporator under vacuum until 593 g of solution remained. Water (500 mL) and EtOAc (500 mL) were added and the layers were separated, and the aqueous layer was extracted with EtOAc (200 mL). The combined organic layers were extracted with 1N HCl (500 mL) and water (300 mL). The organic layer was distilled in vacuo to 261 g of oil to which EtOAc was added (160 mL). Heptane (3.4 L) was added rapidly with vigorous stirring for 30 min, and the product crystallized to yield a beige solid (112.36 g, 71% yield, >98% purity by HPLC analysis). Another crop of crystals may be obtained from the filtrate by concentrating and filtering the solids, or by concentrating more fully to a solution and adding heptane to crystallize. NMR, MS, and EA.

Preparation 84

4-(2-Amino-2-methylpropyl)phenol acetic acid salt

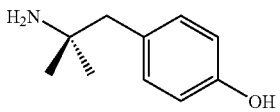

A one-gallon high-pressure reactor was charged with 4-(2-methyl-2-nitropropyl)phenol (120 g, 614 mmol), HOAc (35.2 mL, 614 mmol), 5% Palladium on carbon (24 g) wetted with 2B3 EtOH (60 mL), and MeOH (1230 mL). The mixture was heated to 50° C. with agitation (600 rpm), and the reactor was purged with $N_2$ and pressurized to 50 psi with $H_2$. After 15.5 h the reactor was purged with $N_2$, and the cooled mixture was filtered. The filter cake was washed with MeOH and the filtrate was concentrated to 514 g of slurry on a rotary evaporator. To this slurry was added EtOAc (2 L) with vigorous agitation. After stirring for 1 h, the resulting crystals were filtered and washed with a small amount of EtOAc. The product was dried overnight in a 45° C. vacuum oven to yield 118.83 g (86%) of product as small white needles (mp 211–216° C. dec). This material was 99% pure by HPLC analysis, and while another 9.00 g of material was obtained from the mother liquor it was found to be only 88% pure. NMR. EA.

Preparation 85

2-(4-(2-Amino-2-methylpropyl)phenoxy)-5-carbamoylpyridine

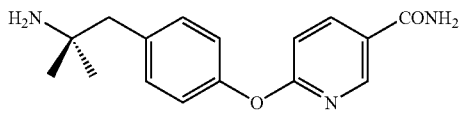

A mixture of 4-(2-amino-2-methylpropyl)phenol acetic acid salt (45.06 g, 200 mmol), powdered $K_2CO_3$ (69.1 g, 500 mmol), 6-chloronicotinamide (31.32 g, 200 mmol), DMAC (622 mL) and iso-octane (70 mL) was slowly heated to reflux at 140° C. A water trap filled with iso-octane was used to collect water formed in the reaction, and reflux was maintained for 5.5 h. The mixture was allowed to cool to room temperature, and the solids were filtered and washed with EtOAc. The filtrate was concentrated in vacuo to 88.6 g of solid which was dissolved in EtOAc (500 mL). To this solution was added water (800 mL), 1N HCl (200 mL) and MeOH (50 mL). The pH of this mixture was adjusted to 7.2 with con. HCl, and the aqueous layer was separated and washed with methyl t-butyl ether (500 mL). The product was crystallized by addition of 10N NaOH (20 mL) which raised the pH to 11. This pH was maintained by addition of 10N NaOH as needed during the course of the crystallization (90 min). The product was filtered, washed with water and dried in vacuo at 45° C. to 53.11 g (93%) of white solid which was >98% pure by HPLC analysis: $^1$H NMR (300 MHz, DMSO-$d_6$) NMR was consistent with the desired product.

Preparation 86

4-(4-(2-Amino-2-methylpropyl)phenoxy)benzonitrile

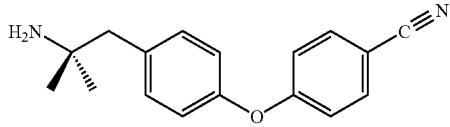

A mixture of 4-(2-amino-2-methylpropyl)phenol acetic acid salt (45.06 g, 200 mmol), powdered $K_2CO_3$ (69.1 g, 500 mmol), and DMAC (550 mL) was heated to 75–100° C. Toluene (166 mL) was added, and the mixture was slowly heated to reflux at 134° C. The reflux temperature was raised by distillation of toluene and water into a water trap until the temperature reached 141° C. The mixture was then allowed to cool to below 100° C. at which point 4-fluorobenzonitrile (24.46 g, 202 mmol) was added along with 50 mL of toluene. The mixture was again heated to reflux at 140° C. with water being collected in a toluene-filled water trap for 4 h. The mixture was allowed to cool to room temperature, and the solids were filtered and rinsed with toluene. The filtrate was concentrated on a rotary evaporator to 77 g of syrup which was dissolved in EtOAc (400 mL). This solution was extracted with water (400 mL), and the aqueous layer was back-extracted with EtOAc (100 mL). The combined organic layers were washed with water (3×400 mL) and concentrated in vacuo to 53.4 g (100%) of oil which was >98% pure by HPLC analysis. NMR.

Preparation 87

4-(4-(2-Amino-2-methylpropyl)phenoxy)benzamide

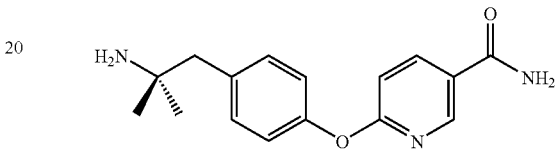

Aqueous 30% $H_2O_2$ (62.1 mL, 548 mmol) was added dropwise to a mixture of 4-(4-(2-amino-2-methylpropyl)phenoxy)benzonitrile (53.2 g, 200 mmol), $K_2CO_3$ (15.78 g, 114 mmol) and DMSO (270 mL) over 20 min while the temperature was held at 20° C. with a cooling bath. The mixture was stirred at this temperature for 1 h after the addition was complete, and then water (209 mL) was added slowly. The slurry was cooled in an ice bath with stirring for 1 h, and the product was then filtered, washed with water and dried in vacuo at 50° C. to yield 55.0 g (97%) of white solid. Analysis by HPLC indicated purity of >99%. NMR.

Preparation 88

2-(4-(2-Amino-2-methylpropyl)phenoxy)-5-cyanopyridine

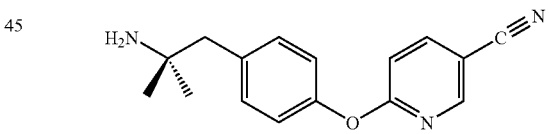

A mixture of 4-(2-amino-2-methylpropyl)phenol acetic acid salt (22.53 g, 100 mmol), powdered $K_2CO_3$ (34.55 g, 250 mmol) and DMAC (275 ml) was heated to 100° C. Toluene (94 ml) was added and the mixture slowly heated to reflux. The reflux temperature was raised by distillation of toluene and water until it reached 140° C. The mixture was then cooled to below 100° C. and 2-chloronicotinonitrile (13.86 g, 100 mmol) added with a toluene rinse (50 ml). The mixture was again heated to reflux and the reflux temperature raised to 140° C. as before. Then the water trap was filled with toluene and the reflux continued for 40 min., at which point HPLC showed no 2-chloronicotinonitrile remained but the reaction was not complete. After cooling the reaction below reflux, additional 2-chloronicotinonitrile (0.63 g, 4.5 mmol) was added and reflux continued for 90 min. The reaction was cooled to room temperature and the solids filtered with a toluene wash. The filtrate was concentrated on a rotary evaporator to 41 g of syrup which was dissolved in EtOAc (200 ml). This solution was washed with water (200 ml) and the aqueous layer back-extracted with EtOAc (50 ml). The combined organic layers were washed with water (3×200 ml) and concentrated in vacuo to 26.93 g of solid, ~100% of theory. HPLC indicated 94.3% purity. $^1$H NMR (300 MHz, DMSO-$d_6$) was consistent with the desired product.

Preparation 89

N-(4-[2-Methyl-2-aminopropyl]phenyl)benzene-sulfonamide

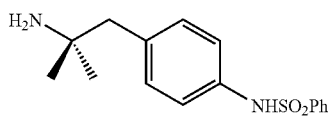

A solution of 4-(2-amino-2-methylpropyl)aniline hydrochloride salt (1.0 g, 4.98 mmol) in anhydrous DMF (30 mL) was treated with benzenesulfonyl chloride (880 mg, 4.98 mmol). The solution was stirred at ambient temperature for 16 h. The solvent was removed under reduced pressure and the residue was washed twice with hexane. The insoluble material was dissolved in water and extracted twice with ethyl ether to remove any remaining neutral impurities. The aqueous layer was separated and basified with excess 1N sodium hydroxide. Upon standing, a crystalline solid soon precipitated. The solid was collected, and dried under vacuum at 60° C. to provide 570 mg (38%) of the desired product as a white crystalline solid. Mp 180–181° C.

Preparation 90

4-(2-Hydroxy-3-aminopropoxy)-9H-carbazole

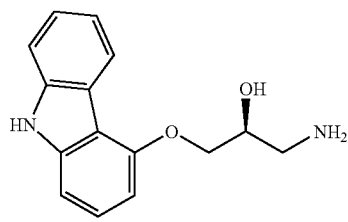

A solution of (S)-4-(oxiranylmethoxy)-9H-carbazole (215.5 mg, 0.9 mmol) in methanol (25 ml) was treated with dibenzylamine (520 ml, 2.7 mmol) and stirred at reflux for 4 h. The solution was cooled to ambient temperature, treated with 10% palladium on carbon (400 mg) and ammonium formate, (2.0 g, 31.7 mmol) and heated to reflux for 4 hours. The suspension was cooled and filtered through a pad of celite, and the filtrate concentrated in vacuo. The residue was purified by flash chromatography over silica eluting with CHCl$_3$:MeOH (95:5) and then CHCl$_3$:MeOH:NH$_4$OH (25:5:1) to give a white solid (140 mg, 61%). NMR Preparation 91

Ethyl-(4-[2-methyl-2-nitropropyl]phenoxy)acetate

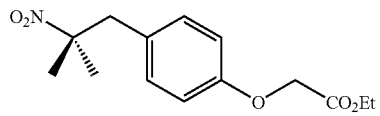

A mixture of 4-(2-methyl-2-nitropropyl)phenol (3.0 g, 15.4 mmol), ethylbromoacetate (2.04 mL, 17.0 mmol) and potassium carbonate (6.4 g, 46.2 mmol) was stirred at room temperature for 18 h. The reaction was concentrated in vacuo and the resulting residue partitioned between EtOAc and water. The layers were separated and the aqueous layer extracted with EtOAc (3×). The combined organic layers were washed with water (3×), brine, dried (Na$_2$SO$_4$), and concentrated in vacuo to a brown oil. The material was purified by flash chromatography over silica gel eluting with 5% MeOH/CHCl$_3$ to provide 4.22 g (97%) of a clear oil. NMR Preparation 92

Ethyl-(4-[2-amino-2-methylpropyl]phenoxy)acetate

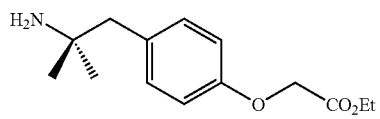

A solution of ethyl(4-[2-methyl-2-nitropropyl]phenoxy)ethanoate (3.6 g, 12.8 mmol) in ethanol (35 mL) was charged with platinum oxide (0.72 g) and hydrogenated on a Parr shaker using 60 psi of hydrogen for 72 h at room temperature. The catalyst was filtered and the solution concentrated in vacuo. The resulting residue was purified by flash chromatography over silica gel eluting with 5% MeOH/CHCl$_3$/NH$_3$ to provide 0.9 g (28%) of a clear oil. MS (FD+): m/z 251.

Preparation 93

4-(4-(N-benzyl-2-aminoethyl)phenoxy)benzamide

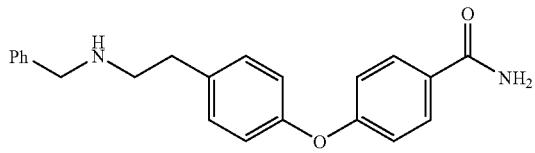

N-benzyl-4-hydroxyphenethylamine (J. Het. Chem., p. 839, 1971; 7.26 g, 0.032 mol) and 6-chloronicotinamide (5.0 g, 0.032 mol) were dissolved in 180 ml of dimethylacetamide and heated to reflux while water was collected in a Dean-Stark trap prefilled with isooctane. The reaction was refluxed under nitrogen for 17 hrs and additional 6-chloronicotinamide (1 g) added. After 2 hours, the solvent was removed in vacuo and the residue dissolved in 125 ml of ethyl acetate. The solution was shaken with dilute HCl and the solids collected by filteration (8.2 g). NMR.

Preparation 94

Ethyl-3-iodo-4-(4-(2-amino-2-methylpropyl)phenoxy)benzoate

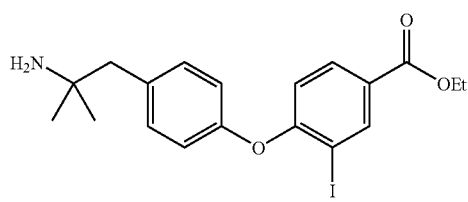

Ethyl-3-iodo-4-fluorobenzoate (2.28 g, 7.75 mmol) and the acetic acid salt of 4-(2-amino-2-methylpropyl)phenol (1.75 g, 7.75 mmol) were dissolved in N,N-dimethylacetamide (40 ml) and toluene (20 ml) and treated with potassium carbonate (3.2 g, 23.3 mmol, 3 eq.). The mixture was heated with vigorous stirring at 125° C. for 16 hours. The crude reaction mixture was diluted with ethyl acetate (100 ml), washed with water (2×) then brine (1×), dried with $Na_2SO_4$, filtered, and concentrated in vacuo to afford the biphenyl ether as a golden oil (3.15 g, 93%). NMR. MS.

Preparation 95

2-Cyanomethoxyanisole

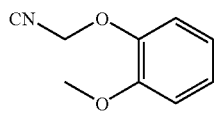

Potassium carbonate (24 g) was added to a solution of of 2-methoxy phenol (18.94 g, 0.152 mol) in acetone (500 ml) at room temperature. A solution of bromoacetonitrile (17.43 g, 0.145 mol) in acetone (500 ml) was then added and the resulting suspension was heated at reflux for 10 h. The reaction vessel was then cooled and the solution was concentrated under reduced pressure and taken up into water (150 ml). Chloroform (250 ml) was added and the two layers separated. The organic phase was washed with brine (100 ml) and 10% aqueous NaOH (100 ml). The organic phase was dried ($MgSO_4$) and concentrated under reduced pressure to give the product (19.91 g, 80%) as an oil. $^1$H NMR ($CDCl_3$, 250 MHz) 7.0 (4H m), 4.8 (2H, s), 3.9 (3H, s).

Preparation 96

2-Aminomethoxyanisole

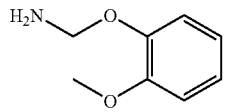

A solution of the 2-cyanomethoxyanisole (5.6 g, 0.034 mol) in anhydrous ammonia (25 ml) and ethanol (50 ml) was heated to 120° C. at 500 psi for 12 h in the presence of raney nickel (1.4 g). The reaction mixture was filtered, concentrated under reduced pressure, the residue taken up in ether, and washed with 1.2 M HCl. The acidic phase was then rendered basic (pH=12) with careful addition of solid KOH and the alkaline solution extracted with ether. The organic phase was dried ($MgSO_4$) and concentrated under reduced pressure to give the product (1.99 g, 35%) as an oil. IR. NMR. MS.

Preparation 97

4-(4-(2-amino-2-methylpropyl)phenoxy)phenyl methylsulfone

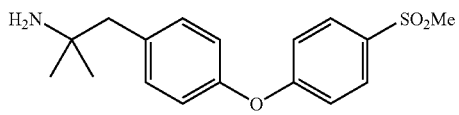

Titled compound was prepared substantially in accordance with Example 94 by starting with 4-fluorophenylmethylsulfone (3.1 g, 17.75 mmol) to yield product (4.67 g) after purification as a tan solid. NMR.

Preparation 98

Methyl-2-trifluoromethyl-4-(4-(2-amino-2-methylpropyl)phenoxy)benzoate

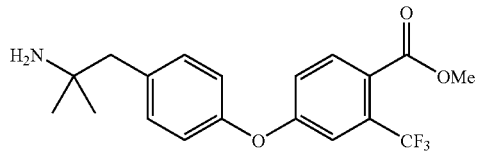

The phenol from preparation 16 (2.9 g, 13 mmol), 4-fluorophenyl-2-trifluoromethyl-methylsulfone (2.9 g, 13 mmol), and potassium carbonate (4.2 g, 30 mmol) were heated to 100° C. in 50 ml of dimethylacetamide. After 17 hours, the reaction mixture was cooled, filtered, and concentrated in vacuo. The residue was purified by column chromatography to yield 1.9 g of pale yellow oil. NMR.

Preparation 99

4-(4-Cyanophenoxy)benzoic acid

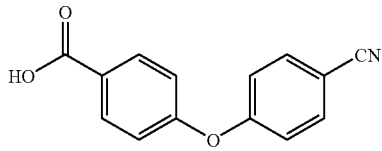

A mixture of 4-hydroxybenzoic acid (3.50 g, 25 mmol), 4-fluorobenzonitrile (3.00 g, 35 mmol), and powdered $K_2CO_3$ (6.80 g, 49 mmol) were heated in DMAC (50 mL) at 140° C. for 20 hours. The cooled mixture was then acidified with 1N HCl and extracted with EtOAc (3×50 mL). Concentration of the extracts in vacuo left a residue which was chromatographed over silica gel (5% MeOH/CHCl$_3$) to provide 2.30 g (39%) of pure product. MS (FD+) 238.9

Preparation 100

2-(4-(2-Amino-2-methylpropyl)phenoxy)pyridine

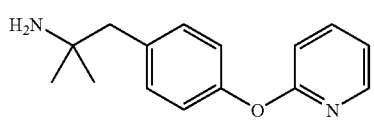

Titled compound was prepared substantially in accordance with Example 94 by starting with 2-fluoropyridine (1.72 g, 17.75 mmol) to yield product (1.28 g) after purification as a brown oil. EA. NMR.

Preparation 101

N-[2-Amino-2-methylpropyl]-4-(4-cyanophenoxy)benzamide

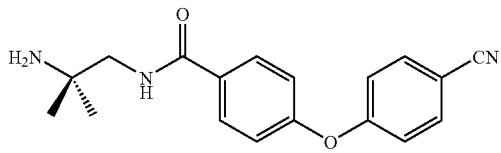

4-(4'-Cyanophenoxy)benzoic acid (1.00 g, 4.2 mmol) was dissolved in THF (40 mL) followed by the addition of 1,1-carbonyldiimidazole (0.745 g, 4.6 mmol) in small portions. This mixture was stirred for 1 hour whereupon 1,2-diamino-2-methylpropane (0.48 mL, 4.6 mmol) was added and the resultant mixture stirred for 20 hours at RT. The mixture was then concentrated in vacuo and the residue chromatographed over silica (10% MeOH/CHCl$_3$) to provide 0.50 g (38%) of the desired product. MS. (FD+) 310.2 m.p. 133–137° C.

Preparation 102

4-(4-(2-Methyl-2-nitropropyl)phenoxy)benzaldehyde

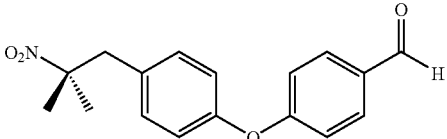

A mixture of 4-(2-methyl-2-nitropropyl)phenol (5.00 g, 25.6 mmol), 4-fluorobenzaldehyde (3.17 g, 25.6 mmol), and powdered $K_2CO_3$ (4.00 g, 29 mmol) were heated in DMAC (50 mL) at 140° C. for 20 hours. The cooled mixture was then diluted with water and the organics extracted with EtOAc (3×50 mL). Concentration of the extracts in vacuo left a residue which was chromatographed over silica gel (5% MeOH/CHCl$_3$) to provide 6.15 g (80%) of pure product. MS(FD+) 299. EA.

Preparation 103

4-(4-(2-Methyl-2-nitropropyl)phenoxy)phenol

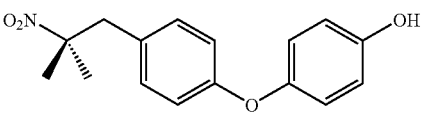

4-(4-(2-Methyl-2-nitropropyl)phenoxy)benzaldehyde (6.00 g, 20 mmol) was dissolved in chloroform (500 mL). m-Chloroperoxy-benzoic acid (10.0 g, 58 mmol) was added in small portions at RT. After stirring for 1 hour, the mixture was concentrated in vacuo and MeOH (300 mL) added followed by the dropwise addition of conc. HCl (5 mL). This mixture was stirred for 3 hours at RT and then concentrated in vacuo. Chromatography over silica gel (MeOH/CHCl$_3$) allowed for the isolation of 3.20 g (55%) of the desired product. MS(FD+): 287.2

Preparation 104

4-(4-(2-Methyl-2-aminopropyl)phenoxy)phenol

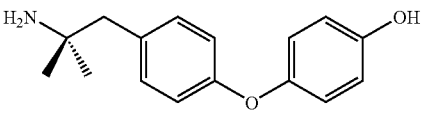

A mixture of NiCl$_2$.6H$_2$O (1.40 g, 5.9 mmol) in MeOH (100 mL) was stirred at RT under a nitrogen atmosphere. Sodium borohydride (0.675 g, 17.9 mmol) was carefully added to the mixture in small portions. Twenty minutes after complete addition of the initial sodium borohydride 4-(4-(2-methyl-2-nitropropyl)phenoxy)phenol (3.20 g, 11 mmol) was added followed by the careful portionwise addition of more NaBH$_4$ (1.58 g, 42 mmol) which caused a frothing exothermic reaction. All starting nitro compound had been consumed within 15 minutes of the last hydride addition as judged by TLC analysis. The mixture was then filtered through Celite and the filtrate concentrated in vacuo. The resulting residue was chromatographed over silica gel (MeOH/CHCl₃) which allowed for isolation of both the incompletely reduced hydroxylamine product (0.675 g, 22%) and the desired amine product (0.94 g, 34%). MS (FD+): 258 (amine)

Preparation 105

Ethyl-4-benzyloxyphenoxyacetate

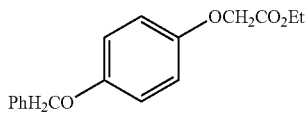

Ethylbromoacetate (4.17 g, 25 mmol) was added to a mixture of 4-benzyloxyphenol (5.00 g, 25 mmol) and K₂CO₃ (3.50 g, 25 mmol) in DMF (75 mL) and stirred for 20 hours at ambient temperature. The mixture was then concentrated in vacuo and the residue partitioned between water and EtOAc. The aqueous phase was further extracted with 2×50 mL of EtOAc and the combined extracts were washed with 2×50 mL of water and dried over Na₂SO₄. Concentration of the organic solution in vacuo left 7.00 g (97%) of product as a white solid. m.p. 65–68° C.

Preparation 106

Ethyl-4-hydroxyphenoxyacetate

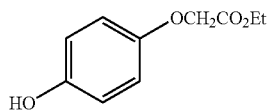

Ethyl-4-benzyloxyphenoxyacetate compound (3.50 g, 12.2 mmol) was placed in a PARR bottle along with EtOAc (75 mL), EtOH (75 mL), and 5% Pd/C (1.20 g) and the mixture placed under 40 psi of H₂. The reaction was shaken under pressure for 4 hours after which no starting material remained by TLC. The catalyst was removed by filtration through Celite and the filtrate concentrated in vacuo to give 2.35 g (97%) of the desired phenol. MP Preparation 107

Ethyl-4-(2-t-butylcarboxyethyl)phenoxyacetate

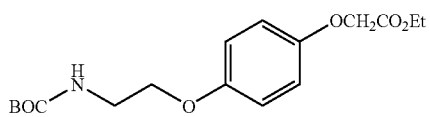

Ethyl-4-hydroxyphenoxyacetate (1.35 g, 6.9 mmol) was combined with N-(t-butoxycarboxy)ethanolamine (1.00 g, 6.2 mmol), triphenylphosphine (1.79 g, 6.8 mmol) and DEAD (1.30 mL, 8.3 mmol) in THF (50 mL) and stirred for 35 hours at RT. The solvent was removed in vacuo and the resulting residue chromatographed over silica gel (30–40% EtOAc/Hexanes) which resulted in recovery of a phenol/product mix. Subsequent chromatography over silica gel (1% MeOH/CHCl₃) allowed for the isolation of the desired product as an oil 0.870 g (41%). MS (FD+): 339. EA.

Preparation 108

Ethyl-4-(2-aminoethyl)phenoxyacetate

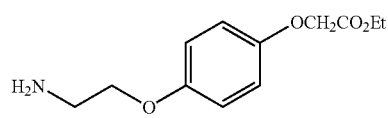

Ethyl-4-(2-t-butylcarboxyethyl)phenoxyacetate (0.80 g, 2.35 mmol) was stirred for two hours at RT with TFA (2 mL) in dichloromethane (20 mL). The mixture was then quenched into aqueous NaHCO₃ and the organics extracted with 3×20 mL of dichloromethane. The combined extracts were concentrated in vacuo and the resulting residue chromatographed over silica gel (CHCl₃) which allowed for isolation of 0.50 g (89%) of the desired amine as a thick oil. MS (FD+): 239.

Preparation 109

N-Butyloxycarbonyl-4-(3-methyl-3-aminobutyl)methyl benzoate

To a suspension of 4-(3-methyl-3-aminobutyl)methyl benzoate hydrochloride (3.01 g), sodium carbonate (3.71 g, 3.0 eq.), 30 mL of dioxane, and 30 mL of water at 0° C. was added di-t-butyldicarbonate (2.55 g, 1 eq.) in 5 mL of dioxane. The resulting solution was allowed to stir for 1.5 hours. The reaction was diluted with and partitioned between ethyl acetate and water. The aqueous layer was removed and the organic layer was washed with brine, dried over sodium sulfate, filtered, and concentrated in vacuo. The residue was purified via silica gel column chromatography eluting with 25% ethyl acetate/toluene to give 2.81 g of the title compound. Yield: 75%.

Preparation 110

N-Butyloxycarbonyl-4-(3-methyl-3-aminobutyl) benzoic acid

To a solution of N-butyloxycarbonyl-4-(3-methyl-3-aminobutyl)methyl benzoate (1.9 g) in 20 mL of ethanol was added 12 mL of 5N sodium hydroxide (10 eq.). The resulting solution was allowed to stir for 3 hours. The solvent was concentrated in vacuo and the residue was taken up in water. The resulting alkaline solution was neutralized with 5N hydrochloric acid (3 mL). This mixture was extracted twice with ethyl acetate and the extracts were washed with brine, dried over sodium sulfate, filtered, and concentrated in vacuo to give 1.59 g of the title compound. Yield: 87%. ¹H NMR.

Preparation 111

N-(Benzamid-4-yl)-N'-butyloxycarbonyl-4-(3-methyl-3-aminobutyl)benzamide

To a solution of N-butyloxycarbonyl-4-(3-methyl-3-aminobutyl)benzoic acid (1.9 g) in 5 mL of pyridine under a nitrogen atmosphere was added thionyl chloride (0.036 mL, 1.1 eq.). The resulting solution was allowed to stir until TLC indicated conversion of the starting acid to the acid chloride. 4-Aminobenzamide (44 mg, 1 eq.) was then added and the resulting solution was allowed to stir for 4 hours. The solvent was removed in vacuo and the crude product was recrystallized from ethanol to give 62 mg of the title compound.
Yield: 45%. $^1$H NMR.

Preparation 112

N-Butyloxycarbonyl-4-(3-methyl-3-aminobutyl) benzoic acid piperidyl amide

To a flame dried flask under a nitrogen atmosphere was added N-butyloxycarbonyl-4-(3-methyl-3-aminobutyl)benzoic acid (500 mg), piperidine (0.161 mL, 1.0 eq.), 1-hydroxybenzotriazole (47 mg, 1.0 eq.), diisopropylethylamine (0.2 mL, 3.5 eq.), and 25 mL of methylene chloride. A solution of (dimethylaminopropyl)ethyl carbodiimide in 20 mL of methylene chloride was then added and the resulting solution was allowed to stir for 1 hour before diluting with ethyl acetate. This mixture was acidified with 10% aqueous citric acid. The organics were washed twice each with saturated aqueous sodium bicarbonate and brine, dried over sodium sulfate, filtered, and concentrated in vacuo. The residue was taken up in ethyl acetate and was washed twice with 10% aqueous sodium bicarbonate, once with brine, dried over sodium sulfate, filtered, and concentrated in vacuo to give the title compound.

Preparation 113

N-(Benzamid-4-yl)-4-(3-methyl-3-aminobutyl)benzamide

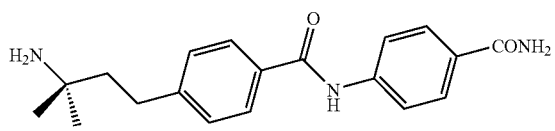

To a flame dried flask under a nitrogen atmosphere was added N-(benzamid-4-yl)-N'-butyloxycarbonyl-4-(3-methyl-3-aminobutyl)benzamide (370 mg), 10 mL of methylene chloride, and trifluoroacetic acid (0.67 mL, 10.0 eq). The resulting solution was allowed to stir for about 18 hours. The pH was adjusted to 7 with 1N hydrochloric acid and the mixture was extracted with ethyl acetate. The organics were washed with brine, dried over sodium sulfate, filtered, and concentrated in vacuo to give 260 mg of the title compound.
Yield: 92%. MS(FD): 326 (M+1). $^1$H NMR.

Preparation 114

4-(3-Methyl-3-aminobutyl)benzoic acid piperidyl amide

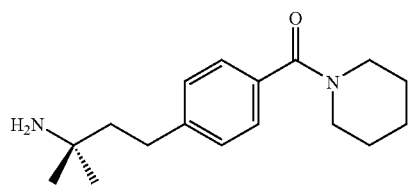

N-Butyloxycarbonyl-4-(3-methyl-3-aminobutyl)benzoic acid piperidyl amide(540 mg) was converted to the titled product substantially in accordance with procedure 113 except that after final concentration the residue is redissolved in 1N hydrochloric acid. This acidic solution was made basic with 5N sodium hydroxide and extracted twice with ethyl acetate. The organic extracts were washed with brine, dried over sodium sulfate, filtered, and concentrated in vacuo to give 284 mg of the title compound. Yield: 72%. MS(FD): 275 (M+1). $^1$H NMR.

Preparation 115

(2R)-1-(4-hydroxyphenyl)-2-(N-[(R)-a-methylbenzyl])amino propane hydrochloride

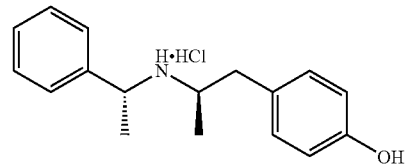

A mixture 4-(2-oxopropyl)phenol (101.03 g, 673 mmol), (R)-(+)-α-methylbenzylamine (91.1 mL, 706 mmol), wet (60% (w/w) H$_2$O) 2% Pt, 8% Pd/C (8.42 g, 5 wt % dry load), and EtOH (560 mL) was placed in an autoclave which was pressurized to 50 psi with hydrogen at 23° C. After stirring for 4 h, the mixture was filtered, and the filtrate was concentrated on a rotary evaporator to 179 g of thick oil. This oil was dissolved in CH$_2$Cl$_2$ (1300 mL), and 2N HCl (363 mL) was added which caused precipitation of the hydrochloride salt. This mixture was stirred for 2 h, filtered, washed with CH$_2$Cl$_2$ and 2N HCl, and was dried in a 45° C. vacuum oven to yield 135.96 g (69%) of a white solid. The optical purity of the material was determined by GC analysis and was shown to be 93.7% de. A small portion of this material (10.02 g) was suspended in CH$_2$Cl$_2$ (65 mL), and concentrated NH$_4$OH (6.7 mL) and water (10 mL) were added which caused the solid to dissolve. The pH was then lowered to 0.2 with con. HCl, and the slurry was filtered, washed with water and CH$_2$Cl$_2$ and dried as above to give 9.47 g (94% recovery) of product as a white solid (mp 224° C. [dec]). NMR. MS (FD+) m/z 256 (39%), 148 (100%).

Preparation 116

(2R)-1-(4-Hydroxyphenyl)-2-aminopropane hydrochloride

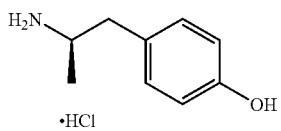

A hastalloy autoclave was charged with (2R)-1-(4-hydroxyphenyl)-2-(N-[(R)-a-methylbenzyl])amino propane hydrochloride (72.3 g, 248 mmol), 5% Pd/C (16.0 g, wetted with 100 mL of EtOH), and MeOH (400 mL). The autoclave was pressurized to 50 psi $H_2$ and heated to 50° C. for 6 h with vigorous stirring. After cooling, purging with nitrogen and filtering the mixture, the filtrate was concentrated on a rotary evaporator under vacuum. The resulting oily foam was dissolved in a minimal amount of MeOH and was triturated by addition of EtOAc. The solid was filtered, and another crop of solid which precipitated from the filtrate was also collected. The combined solids were dried in a 45° C. vacuum oven overnight to yield 34.2 g (73%) of a white solid. MP 160° C. [dec]). MS(FD+) m/z 151 (92%).

Preparation 117

(2R)2-(4-(2-Aminopropyl)phenoxy)-5-carbamoylpyridine hydrochloride

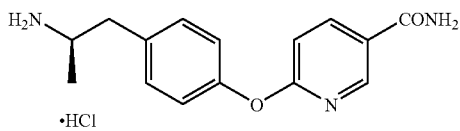

A 3-L flask was charged with (2R)-1-(4-hydroxyphenyl)-2-aminopropane hydrochloride (50.0 g, 266 mmol), powdered $K_2CO_3$ (91.91 g, 665 mmol), 6-chloronicotinamide (41.65 g, 266 mmol) and dry (<0.1% $H_2O$) DMAC (1 L). The mixture was heated to 140–142° C., and a steady stream of nitrogen was passed through the flask and out of the distillation apparatus. After 4.5 h, 415 mL of distillate had been collected, and the mixture was cooled to 15° C. The potassium salts were filtered and the filter cake was washed with DMAC (200 mL). The filtrate was concentrated under vacuum with an 80° C. water bath. Xylenes (250 mL) were added to the residue and the solution was concentrated as above to yield 107 g of solid. This product was crystallized from refluxing methyl-t-butyl ether (500 mL) which was allowed to cool slowly to 23° C. over 3 h. The solid material was filtered, washed with MTBE (200 mL) and dried in a 45° C. vacuum oven to provide 69.91 g of solid. This product was taken up in refluxing toluene (1738 mL) which caused an oil to form in solution. The stirring was stopped to allow the oil to settle to the flask sides, and the flask was then removed from the heating mantle. The hot toluene solution was decanted from the oil into another flask, and the solution was allowed to cool to ambient temperature with stirring over the course of 4 h. The resulting precipitate was filtered, rinsed with toluene (200 mL) and was dried in a 45° C. vacuum oven to yield 55.40 g (77%) of material as a white solid (mp 140–141° C.). $^1$H NMR. MS(FAB) m/z 272.1393.

Preparation 118

4-Fluoroanisole-2-Boric Acid

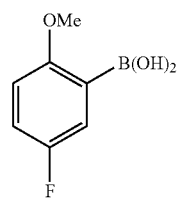

To a solution of 2-bromo-4-fluoroanisole (20.0 g, 97.6 mmol) in 100 mL of tetrahydrofuran at −55° C. to −65° C. was added n-butyl lithium (2.5 M in hexanes, 39 mL) via syringe. After 15 minutes, triisopropylborate (25 mL, 110 mmol) was added and the resulting solution was allowed to warm to −25° C. at which point 1N hydrochloric acid was added. The quenched reaction was stirred for 15 minutes, diluted with 200 mL of ethyl acetate, and the 2 layers were separated. The organic layer was dried over magnesium sulfate, filtered, and concentrated in vacuo to give a pale yellow semi-solid which was triturated with hexane to give 6.8 g of the title compound.

Yield: 41%. $^1$H NMR. MS(FD).

Preparation 119

2-(2-Nitrophenyl)-4-fluoroanisole

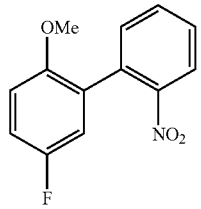

A mixture of 4-fluoroanisole-2-boronic acid (3.3 g, 19.4 mmol), 2-nitrobromobenzene (3.56 g, 17.6 mmol), triphenylphosphine (367 mg, 1.4 mmol), triethylamine (4.6 g, 45.8 mmol), and 40 mL of dimethylformamide was sparged with nitrogen for 5 minutes before adding palladium acetate (160 mg, 0.7 mmol) and heating the mixture to 100° C. for 5 hours. The reaction was cooled and concentrated in vacuo. The residue was partitioned between ethyl acetate and water. The organic layer was shaken with 0.1N sodium hydroxide, dried over magnesium sulfate, filtered, and concentrated in vacuo. The crude product was purified via flash silica gel chromatography eluting with 2% ethyl acetate/hexanes followed by 4% ethyl acetate/hexanes to give 7.5 g of the title compound. Yield: 86%. EA. MS(FD).

Preparation 120

1-Fluoro-4-methoxycarbazole

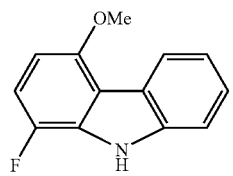

A mixture of 2-(2-nitrophenyl)-4-fluoroanisole (427 mg, 1.73 mmol) and triethyl phosphite (3 mL) was heated to reflux for 3.5 hours. The reaction was cooled and concentrated in vacuo. The crude product was purified via flash silica gel chromatography eluting with 2% ethyl acetate/hexanes followed by 5% ethyl acetate hexanes to give 212 mg of the title compound.
Yield: 57%. MS(FD).

Preparation 121

1-Fluoro-4-Hydroxycarbazole

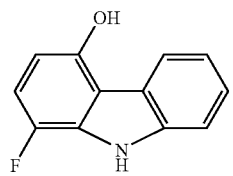

A mixture of 1-fluoro-4-methoxycarbazole (438 mg, 2.04 mmol) and pyridine hydrochloride (3 g) was placed into an oil bath that was preheated to 220° C. After 20 minutes, the reaction was poured onto a mixture of ice and concentrated ammonium hydroxide. The product was extracted into ethyl acetate and the extract was dried over magnesium sulfate, filtered, and concentrated in vacuo. The residue was azeotroped with toluene to give 470 mg of the title compound.
Yield: >100%. MS(FD).

Preparation 122

O-Glycidyl-1-Fluoro-4-Hydroxycarbazole

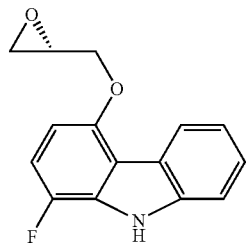

A mixture of 1-fluoro-4-hydroxycarbazole (470 mg, 2 mmol), potassium carbonate (345 mg, 2.5 mmol), (2R)-(–)-glycidyl 3-nitrobenzenesulfonate, (518 mg, 2 mmol), and 20 mL of acetone was heated to reflux for about 18 hours. The reaction was cooled and concentrated in vacuo. The residue was partitioned between ethyl acetate and water. The organic layer was dried over magnesium sulfate, filtered, and concentrated in vacuo. The crude product was purified via flash silica gel chromatography eluting with 10% ethyl acetate/hexanes to give 247 mg of the title compound.
Yield: 48%. $^1$H NMR. MS(FD).

Preparation 123

N-(2-Fluorophenyl)cyclohexenol-3-hydrazide

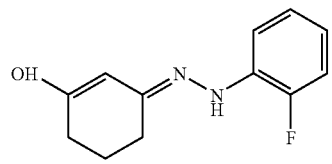

A solution of 2-fluorophenylhydrazine hydrochloride (24.8 g, 152.5.6 mmol) in 225 mL of water and 2.25 mL of isopropanol was added dropwise to a solution of 1,3-cyclohexanedione (17.1 g, 152.5 mmol) in 117 mL of water and 1.1 mL of isopropanol. Sodium bicarbonate (12.6 g, 152.5 mmol) was then added. After 3 hours, the orange powder that formed was collected, washed with 200 mL of water, and dried at 45° C. in a vacuum oven to give 31.5 g of the title compound. Yield: 94%. $^1$H NMR. MS(FD).

Preparation 124

1-Fluoro-5-oxo-5,6,7,8-tetrahydrocarbazole

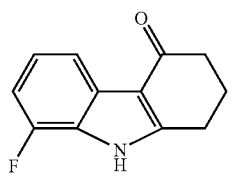

To phosphoric acid (85%, 150 mL) at 90° C. was added a solution of N-(2-fluorophenyl)cyclohexenol-3-hydrazide (30.5 g, 138.5 mmol) in 150 mL of phosphoric acid (85%) dropwise. The resulting solution was heated at 90° C. for 1 hour then cooled to room temperature. Ethanol (250 mL) was added and the quenched reaction mixture was poured into 600 mL of water. This mixture was stirred for 1 hour before the pH was adjusted to 5 with 50% aqueous sodium hydroxide. The alkaline mixture was extracted with ethyl acetate (1 L) and the extract was washed with brine, shaken with celite, filtered, and concentrated in vacuo. The residue was purified via flash silica gel chromatography eluting with 40% ethyl acetate/hexanes followed by 50% ethyl acetate/hexanes to give 2.8 g of the title compound. Yield: 10%. EA. MS(FD).

Preparation 125

1-Fluoro-5-hydroxycarbazole

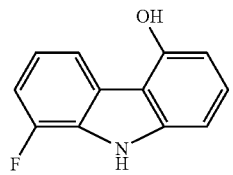

A mixture of 1-fluoro-5-oxo-5,6,7,8-tetrahydrocarbazole (111 mg, 0.55 mmol), copper II bromide (244 mg, 1.09 mmol), and 5 mL of ethyl acetate was heated to reflux for about 12 hours. The reaction was cooled to room temperature, treated with celite, and then filtered. The reaction was partitioned between aqueous sodium bicarbonate and ethyl acetate. The organic layer was dried over magnesium sulfate, filtered, and concentrated in vacuo. The residue was dissolved in 5 mL of dimethylformamide and lithium carbonate (52 mg, 0.7 mmol) and lithium bromide (61 mg, 0.7 mmol) were added. The resulting mixture was heated to reflux for 1.5 hours. The reaction was concentrated in vacuo and the crude product was purified via flash silica gel chromatography eluting with 15% ethyl acetate/hexanes to give 32 mg of the title compound. Yield: 18%. ¹H NMR. MS(FD).

Preparation 126

O-Glycidyl-1-fluoro-5-hydroxycarbazole

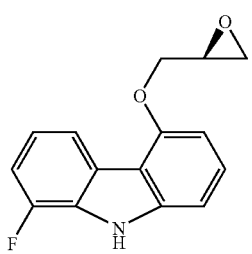

1-Fluoro-5-hydroxycarbazole (25 mg, 0.124 mmol) and (2R)-(−)-glycidyl 3-nitrobenzenesulfonate, (32 mg, 0.124 mmol) were converted to 25 mg of the title compound substantially in accordance with the procedure of Preparation 122. Yield: 65%. ¹H NMR. MS(FD).

Preparation 127

O-Glycidyl-5-hydroxycarbazole

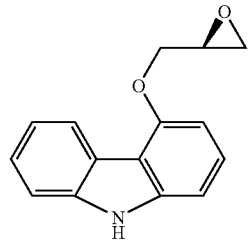

The titled compound can be prepared by procedures known in the art or by utilizing procedures substantially in accordance with preparations 123–126 provided phenyl hydrazine is utilized as a starting material in preparation 123 instead of fluorophenyl hydrazine.

See the following references to obtain 2-benzoyl-1,2,3,9-tetrahydro-4H-pyrido[3,4-b]indol-4-one

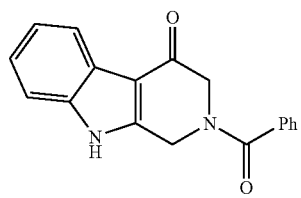

Cain, M.; Mantei R.; Cook, J. M.; *J. Org. Chem.*, 1982, 47, 4933–4936.

Hagen, T. J.; Narayanan, K.; Names J.; Cook, J. M.; *J. Org. Chem.*, 1989, 54, 2170–2178.

For 4-(oxiranylmethoxy)-9H-pyrido[3,4-b]indole as percurser to β-adrenergic blockers see the following:

Corbiere, J.; Fr. Demande FR 2,516,512; 19 Nov. 1981 (CA99:175742q)

Preparation 128

1,2,3,9-tetrahydro-4H-pyrido[3,4-b]indol-4-one

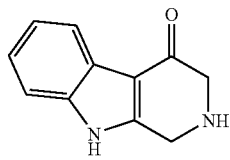

To a warm solution of 2-benzoyl-1,2,3,9-tetrahydro-4H-pyrido[3,4-b]indol-4-one (11.10 g, 38.2 mmol) in dioxane (240 mL) was added 5N NaOH (360 mL) and the mixture refluxed for 2 hr. The reaction was allowed to cool and separate into two layers. The aqueous layer was extracted with EtOAc (3×200 mL). All the organic portions were combined and washed with brine (300 mL), dried (MgSO₄), filtered and evaporated in vacuo to provide the crude product. The material was recrystillized from MeOH to give 5.53 g (78%) of a reddish brown solid. m.p. 220–233° C. decomposed. NMR. FD. EA.

Preparation 129

9H-pyrido[3,4-b]indol-4-ol

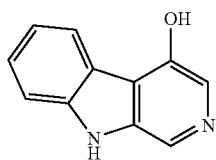

To a mixture of 1,2,3,9-tetrahydro-4H-pyrido[3,4-b]indol-4-one (1.86 g, 10 mmol), dodecene (2.78 mL, 12.5 mmol) and 10% Pd on carbon (750 mg) in 2-methoxyethyl ether (50 mL) was heated at 150° C. for 3 hr. The reaction was filtered while hot through a celite pad and then a majority of the 2-methoxyethyl ether was evaporated in vacuo. The resulting residue was absorbed on silica and chromatographed on a flash column by eluting with EtOAc and then 9 EtOAc/1 MeOH to give 1.65 g (90%) of a yellow foam. NMR. FD.

Example 1 is a combinatorial/parallel method for preparing compounds of the present invention in matrix fashion.

Example 1

A 5×8 grid of 4 mL screw cap vials is arranged. To each of the eight rows of vials in the grid is added 40 µL of a 0.5 M solution of carbazole amine (20 µmol) in 1:1 methanol/DMF, 0.40 µmoles of ketone (weighed into each vial), 100 µl of DMF, 80 µl of methanol, 30 µl of acetic acid, and 80 µL of a 0.25M solution of sodium cyanoborohydride (20 mmol) in methanol. The vial was sealed with a teflon backed cap and shaken at room temperature for 20 hours. The reaction mixture is applied to a 500 µg SCX column. The column was flushed with 2.5 mL methanol to remove byproducts (column was always left moist) and the product was then eluted using 2.5 mL of a 2M solution of ammonia in methanol. The solvent was evaporated, followed by drying in a vacuum oven to yield the product secondary amine product.

The following matrix lists additional examples 2–41. These compounds were prepared using combinatorial/parallel techniques in accordance with the present invention. All reaction conditions are the same from example to example and in substantial accordance with Scheme 2 and Example 1. The scaffold for each plate is the same and is depicted at the top corner of the 5×8 matrix. The variable functional groups are illustrated in the rows and columns. The ketones and the amine depicted for each example are prepared in accordance with the schemes and preparations described herein or by techniques known in the art. Compounds prepared according to Example 1 are those wherein $R_5$ is methyl, $R_6$ is hydrogen, and $R_4$ is as depicted in the matrix.

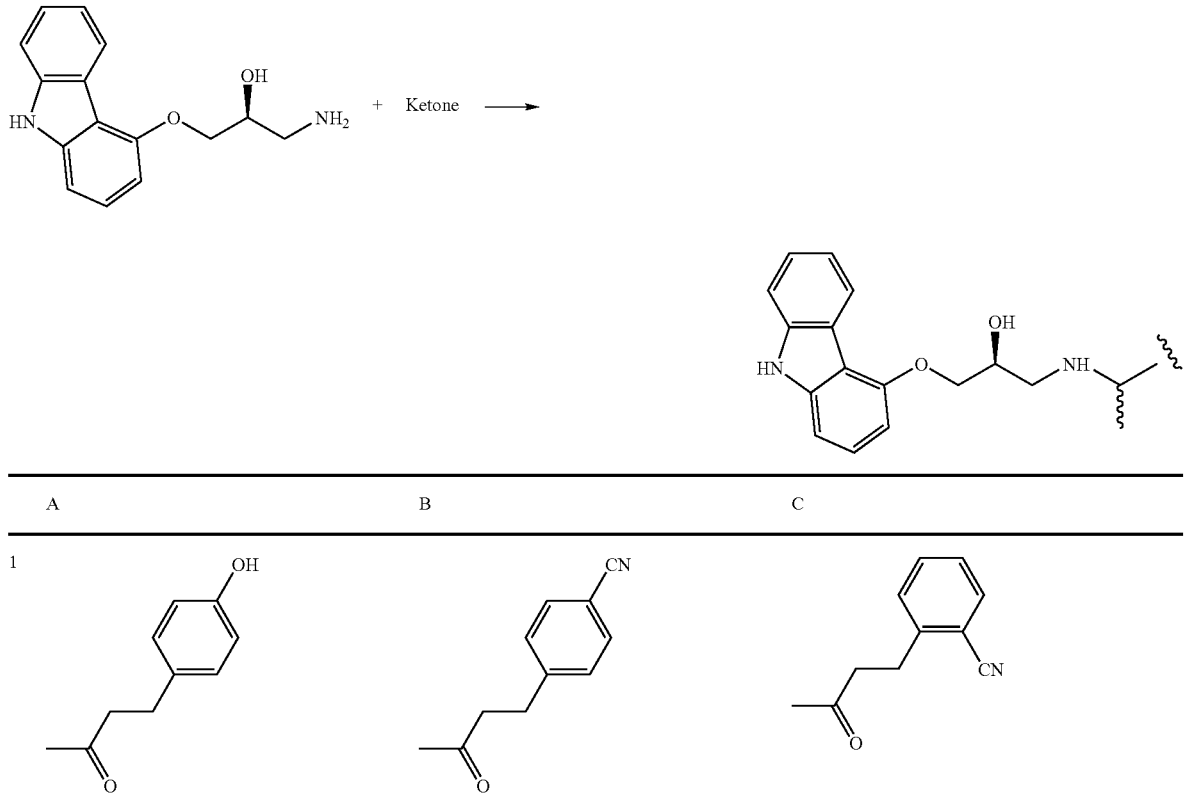

-continued
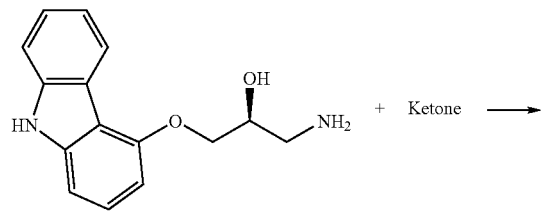 + Ketone → 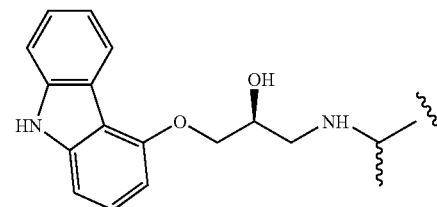
2 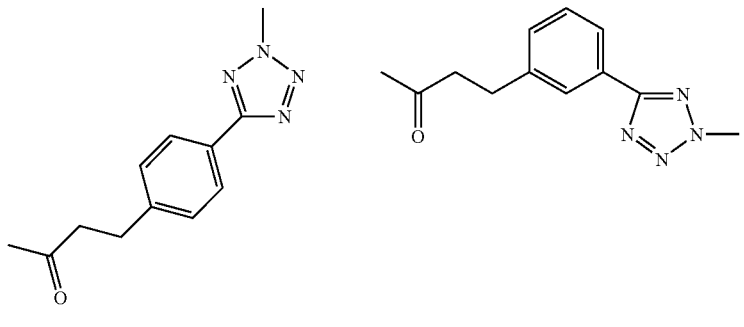
3 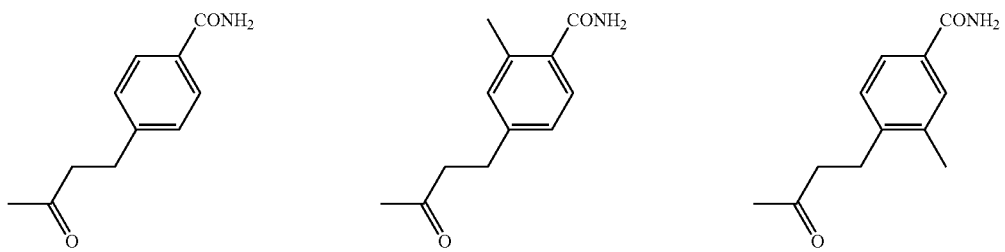
4 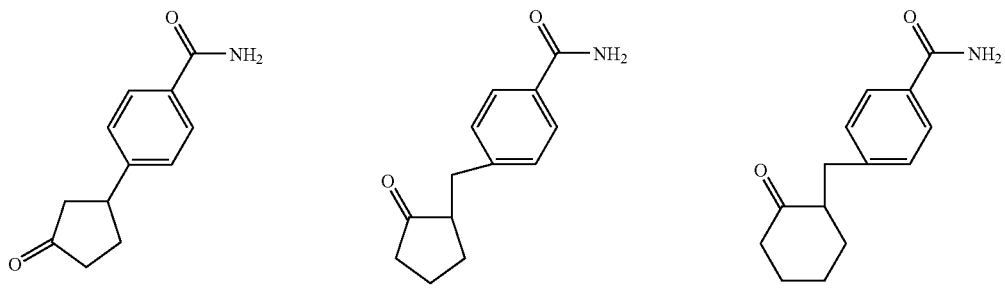

-continued
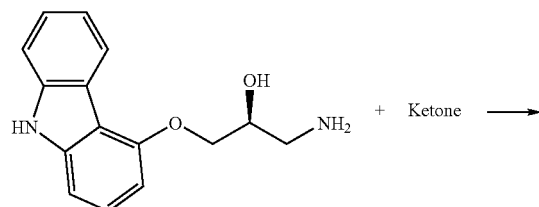 + Ketone →
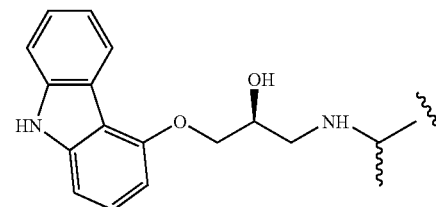
| | D | E | F |
|---|---|---|---|
| 5 | 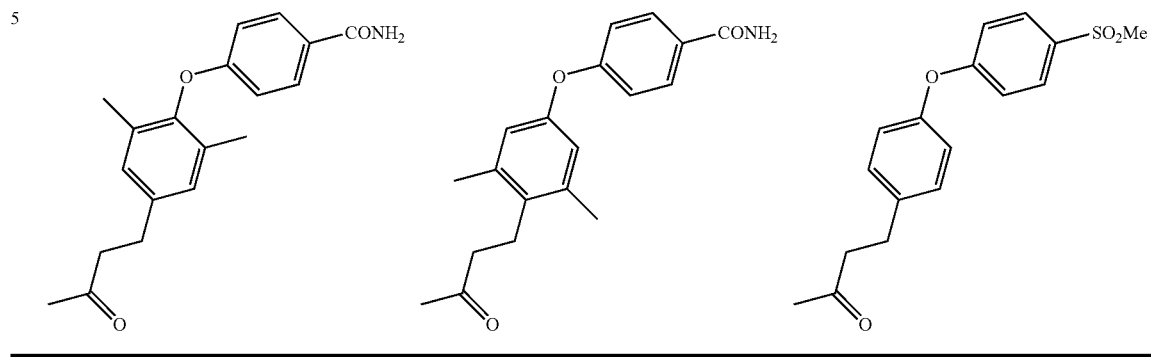 | | |
| 1 | 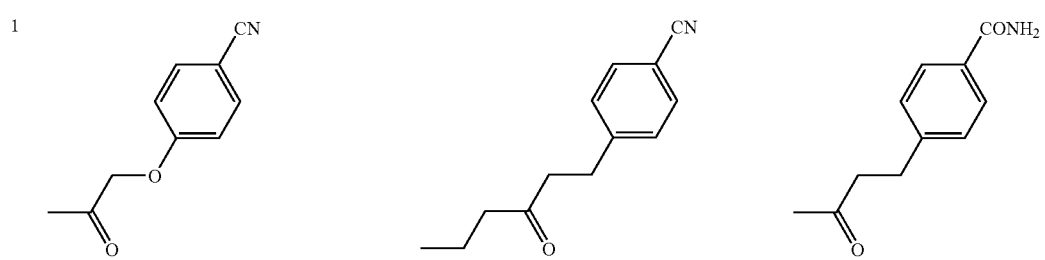 | | |
| 2 | 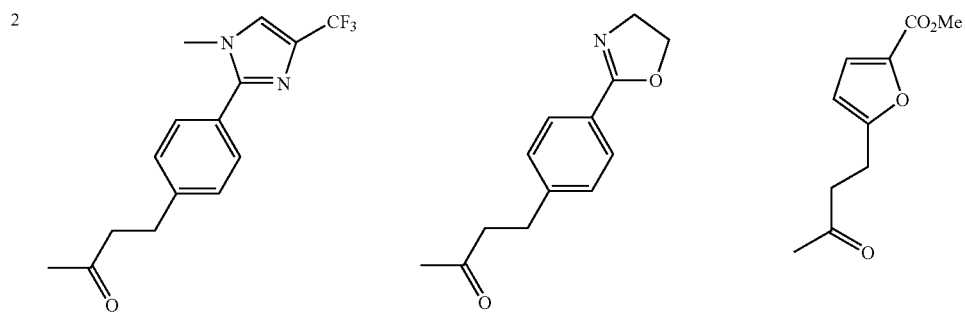 | | |

-continued
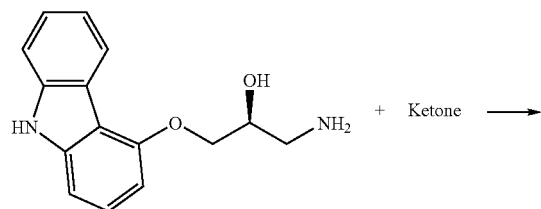 + Ketone ⟶ 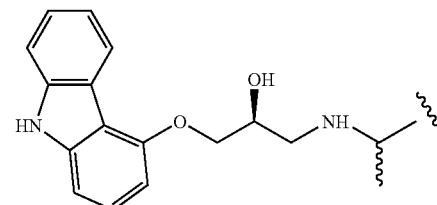
| | | | |
|---|---|---|---|
| 3 | 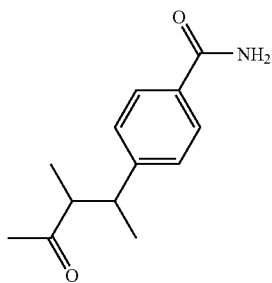 | 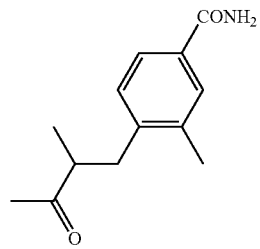 | 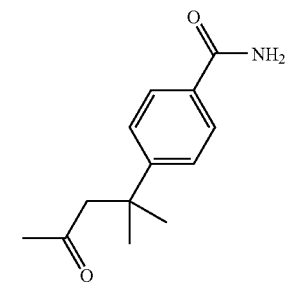 |
| 4 | 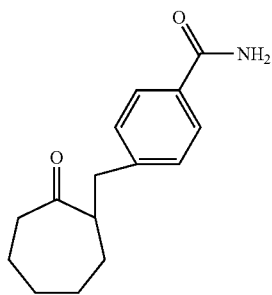 | 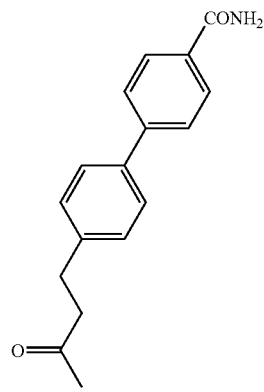 | 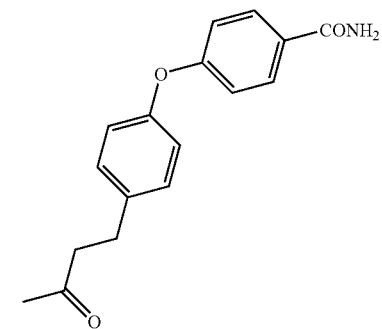 |
| 5 | 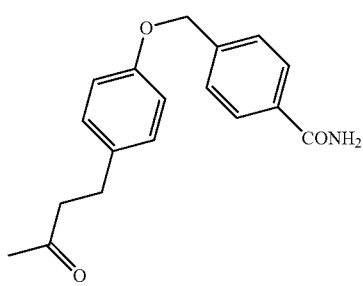 | 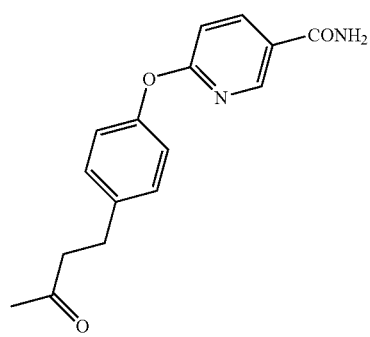 | 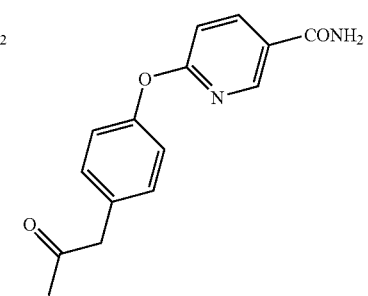 |

-continued
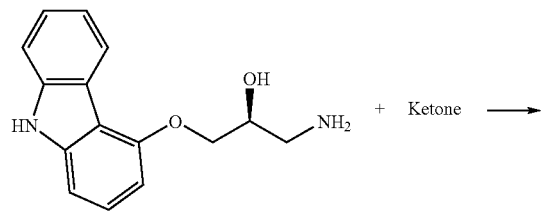 + Ketone →
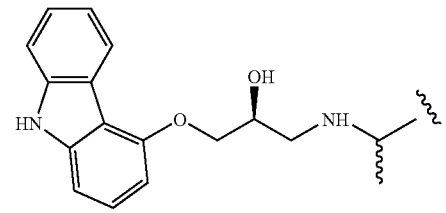
| | G | H |
|---|---|---|
| 1 | 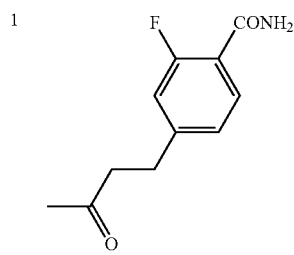 | 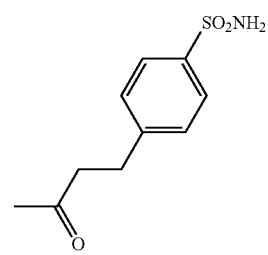 |
| 2 | 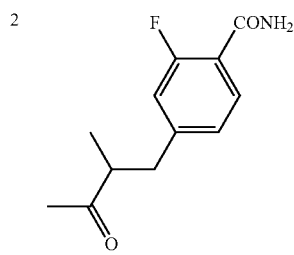 | 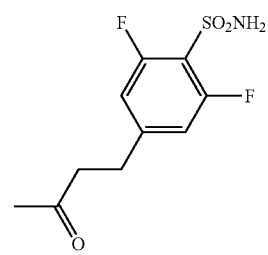 |
| 3 | 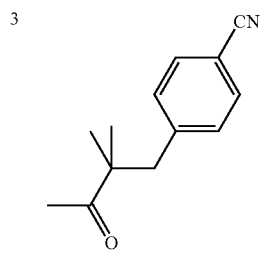 | 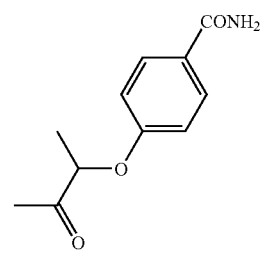 |
| 4 | 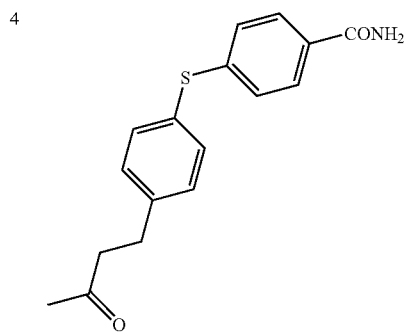 | 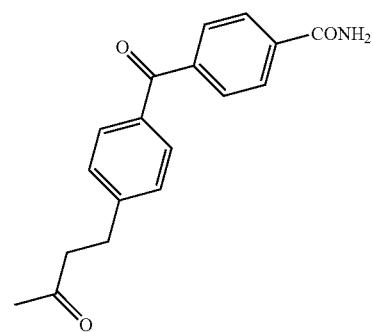 |

-continued

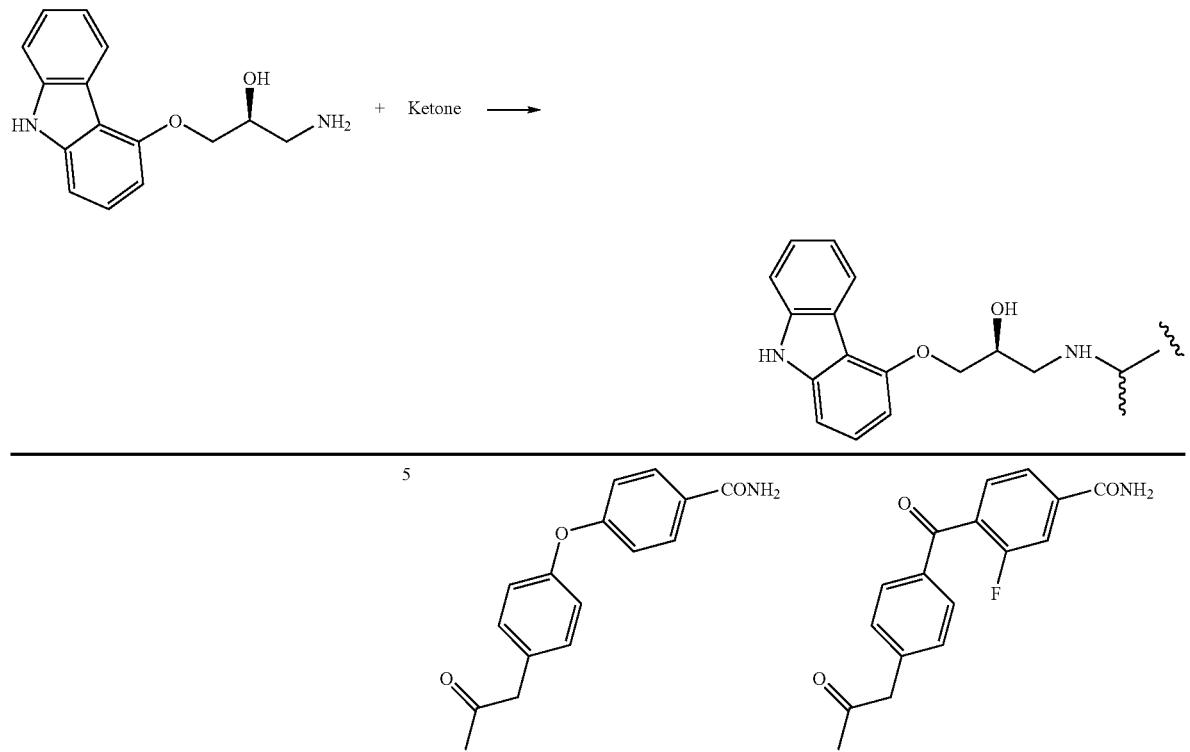

| Example 2 | Ketone A1 | 405.4 (M + 1) |
| Example 3 | Ketone B1 | 414.0 (M + 1) |
| Example 4 | Ketone C1 | 413.8 (M) |
| Example 5 | Ketone D1 | 416.0 (M + 1) |
| Example 6 | Ketone E1 | 442.0 (M + 1) |
| Example 7 | Ketone F1 | 446.0 (M + 1) |
| Example 8 | Ketone G1 | 450.0 (M + 1) |
| Example 9 | Ketone H1 | 468.0 (M + 1) |
| Example 10 | Ketone A2 | 471.0 (M + 1) |
| Example 11 | Ketone B2 | 471.0 (M + 1) |
| Example 12 | Ketone C2 | 547.0 (M + 1) |
| Example 13 | Ketone D2 | 537.0 (M + 1) |
| Example 14 | Ketone E2 | 458.0 (M + 1) |
| Example 15 | Ketone F2 | 436.8 (M) |
| Example 16 | Ketone G2 | 464.2 (M + 1) |
| Example 17 | Ketone H2 | 504.0 (M + 1) |
| Example 18 | Ketone A3 | 432.2 (M + 1) |
| Example 19 | Ketone B3 | 446.0 (M + 1) |
| Example 20 | Ketone C3 | 446.0 (M + 1) |
| Example 21 | Ketone D3 | 460.2 (M + 1) |
| Example 22 | Ketone E3 | 460.2 (M + 1) |
| Example 23 | Ketone F3 | 460.2 (M + 1) |
| Example 24 | Ketone G3 | 442.0 (M + 1) |
| Example 25 | Ketone H3 | 448.0 (M + 1) |
| Example 26 | Ketone A4 | 444.0 (M + 1) |
| Example 27 | Ketone B4 | 458.4 (M + 1) |
| Example 28 | Ketone C4 | 472.0 (M + 1) |
| Example 29 | Ketone D4 | 486.4 (M + 1) |
| Example 30 | Ketone E4 | 508.2 (M + 1) |
| Example 31 | Ketone F4 | 524.2 (M + 1) |
| Example 32 | Ketone G4 | 540.4 (M + 1) |
| Example 33 | Ketone H4 | 536.2 (M + 1) |
| Example 34 | Ketone A5 | 552.2 (M + 1) |
| Example 35 | Ketone B5 | 552.2 (M + 1) |
| Example 36 | Ketone C5 | 559.2 (M + 1) |
| Example 37 | Ketone D5 | 538.4 (M + 1) |
| Example 38 | Ketone E5 | 525.2 (M + 1) |
| Example 39 | Ketone F5 | 511.4 (M + 1) |
| Example 40 | Ketone G5 | 510.2 (M + 1) |
| Example 41 | Ketone H5 | 528.0 (M + 1) |

The skilled artisan would appreciate that Examples 42–82 could be prepared by utilizing methodology of Example 1 and the remaining ketones of preparations 1–82.

| | Ketone |
| --- | --- |
| Example 42 | (4-2,6-dimethyl-(3-oxobutyl)phenoxy)-phenyl)methanenitrile |
| Example 43 | 4-(2,5-dimethyl-(3-oxobutyl)phenoxy)-benzamide |
| Example 44 | 4-(2-ethyl-3-oxobutyl)benzoic acid |
| Example 45 | 4-(2,5-dimethyl-4-(3-oxobutyl)phenoxy)-benzonitrile |
| Example 46 | 3-methyl-4-(2-methyl-3-oxobutyl)-benzonitrile |
| Example 47 | 4-(4-oxopentyl)benzonitrile |
| Example 48 | 4-(2-(4-(3-oxobutyl)phenoxy)ethyl)-benzamide |
| Example 49 | (3-methyl-4-(3-oxobutyl)phenyl)-methanenitrile |
| Example 50 | 2-methyl-4-(3-oxobutyl)benzonitrile |
| Example 51 | 4-(4-(3-oxobutyl)phenyl)benzonitrile |
| Example 52 | 4-(2-(4-(3-oxobutyl)phenoxy)ethyl)-benzonitrile |
| Example 53 | 5-(2-methyl-3-oxobutyl)-2-(morpholinosulfonyl)thiophene |
| Example 54 | 5-(3-oxobutyl)-2-(morpholinosulfonyl)thiophene |

| | Ketone |
|---|---|
| Example 55 | 5-(2-fluoro-4-(2-methyl-3-oxobutyl)-phenyl)-1H-tetrazole |
| Example 56 | 2-fluoro-4-(2-methyl-3-oxobutyl)-benzonitrile |
| Example 57 | 4-(4-(3-oxobutyl)phenoxy)benzonitrile |
| Example 58 | 4-((2-oxocyclopentyl)benzonitrile |
| Example 59 | 5-(2-methyl-3-oxobutyl)-2-thiophene sulfonamide |
| Example 60 | 4-(2,2-dimethyl-3-oxobutyl)benzamide |
| Example 61 | 4-(3-oxobutyl)-phthalhydrazide |
| Example 62 | 4-(3-oxohexyl)benzonitrile |
| Example 63 | 4-(3-oxocycloheptyl)benzonitrile |
| Example 64 | (3-3-oxobutyl)phenyl)sulfonamide |
| Example 65 | 5-(3-oxobutyl)-2-thiophene sulfonamide |
| Example 66 | 4-(3-oxocyclohexyl)benzamide |
| Example 67 | 4-(2-methyl-3-oxobutyl)benzamide |
| Example 68 | 4-(2-methyl-3-oxobutyl)benzonitrile |
| Example 69 | N-methoxyl-4-(3-oxobutyl)benzamide |
| Example 70 | 1-methyl-5-(2-3-oxobutenyl)phenyl-1H-tetrazole |
| Example 71 | 4-(3-oxocyclohexyl)benzonitrile |
| Example 72 | 3-methyl-5-(2-(3-oxobutyl)phenyl-1N-tetrazole |
| Example 73 | (2-fluoro-4-(3-oxobutyl)benzonitrile |
| Example 74 | (4-(3-oxobutyl)phenyl)thioamide |
| Example 75 | 4-(3-oxobutyl)-1-cyanomehtylbenzene |
| Example 76 | tetralone-6-morpholinamide |
| Example 77 | tetralone-6-carboxamide |
| Example 78 | 4-[(2-Oxocyclohexyl)]benzonitrile |
| Example 79 | 2,6-dimethoxy-4-[4-(2-oxobutyl)phenoxy]-1,3,5-trizine |
| Example 80 | 3-[4-(2-oxobutyl)phenoxymethyl]pyridine |
| Example 81 | 5-[4-(2-oxobutyl)phenoxymethyl]tetrazole |
| Example 82 | 4-[4-(3-oxobutyl)phenoxy]benzonitrile |

Example 83

(S)-4-[2-Hydroxy-3-([4-(5-cyano-2-pyridyloxy)phenyl]-2-methylpropylamino)propoxy]carbazole hydrochloride salt

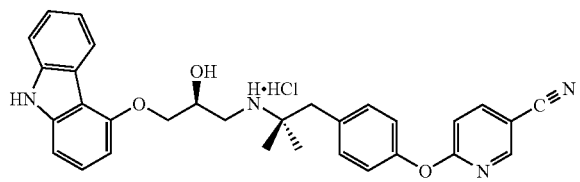

A mixture of 2-(4-[2-amino-2-methylpropyl]phenoxy)-5-pyridinecarbonitrile (20.58 g, 76.98 mmol), (S)-(+)-4-(oxiranylmethoxy)-9H-carbazole (9.18 g, 38.37 mmol), and HOAC (113.6 mg, 1.89 mmol) in MeOH (268 mL) was stirred at 60° C. for 22 hours. The mixture was cooled and concentrated in vacuo to an oil. The residue was dissolved in EtOAc (300 mL), 1N HCl (19 mL), and water (120 ml). The resulting layers were separated. The organic layer was extracted with a solution of 1N HCl/water (10 mL/120 mL), and with a solution of 1N HCl/water (4 mL/120 mL). The organic layer was extracted a final time with a solution of 1N NaOH/10% NaCl/water (10 mL/30 mL/30 mL), dried (Na$_2$SO$_4$) and concentrated in vacuo to yield 21.2 g of a foam. Purification of 20.3 g of the foam by flash chromatography over 500 g of 230–400 mesh silica gel using 50:1:0.01 EtOAc/MeOH/28% NH$_3$ as an eluent yielded 15.28 g (82.24%) of the free base. $^1$H NMR (DMSO-d$_6$) was consistent with the desired product.

A solution of the free base (2.02 g, 4.00 mmol) in EtOAc (40 mL) was made acidic by the addition of a 0.1633 g HCl/g EtOAc solution (897 mg, approx. 2.04 mmol) at room temperature. The resulting slurry was stirred 30 minutes and then vacuum filtered. The filter cake was washed with EtOAc and dried in vacuo at 50° C. to yield 1.58 g (72.81%) of the desired product as a solid. $^1$H NMR was consistent with the desired product and showed small amounts of EtOAc and water): $^1$H NMR (500 MHz, DMSO-d$_6$): d1.30 (s, 6H), 3.15–3.07 (m, 2H), 3.29–3.24 (m, 1H), 3.49–3.47 (m, 1H), 4.28–4.25 (m, 1H), 4.36–4.33 (m, 1H), 4.53 (m, 1H), 6.07 (br s, 1H), 6.75–6.73 (d, 1H), 7.16–7.11 (m, 4H), 7.23–7.21 (d, 1H), 7.36– 7.31 (m, 4H), 7.48–7.47 (d, 1H), 8.32–8.29 (m, 2H). 8.66–8.65 (d, 1H), 8.9 (br s, 1H), 9.5 (br s, 1H), 11.36 (s, 1H).

Example 84

(S)-4-[2-Hydroxy-3-([4-(4-carbamoylphenoxy)phenyl]-2-methylpropylamino)propoxy]carbazole

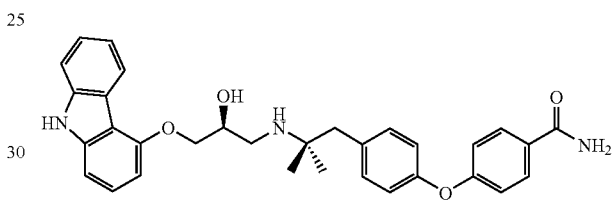

The nitrile from example 83 (2.02 g, 4 mmol) and 0.57 equivalents of powdered potassium carbonate (0.316 g, 2.28 mmol) were stirred in 5.4 ml of DMSO and a cooling bath applied to hold 20° C. as 2.74 equivalents of 30% hydrogen peroxide (1.24 ml, 11 mmol) were added dropwise over 20 min. Stirring was continued at 20 to 26° C. for 1 hour 40 min. Then the reaction mixture was added slowly to 54 ml of water stirring rapidly at ambient temperature, with a rinse of 0.6 ml of DMSO and 6 ml of water. This slurry was stirred 1 hour and filtered with a wash on the filter cake of 60 ml of water. The product was vac dried at room temperature to 1.97 g of white solid, 94% of theory. HPLC indicated 90.2% purity. NMR in DMSO-d6 was consistent with the desired product and showed small amounts DMSO and water.

Example 85

(S)-4-[2-Hydroxy-3-([4-(4-carbamoylphenoxy)phenyl]-2-methylpropylamino)propoxy]carbazole

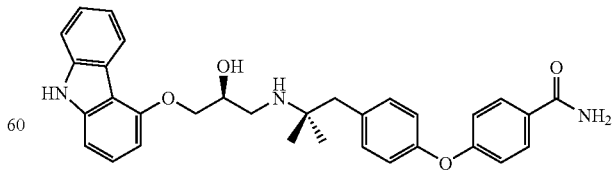

A stirred mixture of (S)-(+)-4-(oxiranylmethoxy)carbazole (7.50 g, 31.3 mmol), 4-(4-(2-amino-2-methylpropyl)-phenoxy)benzamide (17.82 g, 62.67 mmol), acetic acid (0.10 g, 1.7 mmol), water (10 mL) and methanol (260 mL)

was heated to 60° C. for 22.7 hrs. The mixture was cooled and concentrated in vacuo to an oil. The concentrate was taken up in ethyl acetate (250 mL) and partitioned with water (100 mL). The organic layer was then extracted with a solution of 25 mL 1N HCl (25 mL) in water (35 mL). A white precipitate formed during the extraction was mostly 4-(4-(2-amino-2-methylpropyl)-phenoxy)benzamide and was removed by filtration of the two phase mixture. The organic layer was extracted two times with a solution of 1N HCl (3 mL) in water (50 mL). The ethyl acetate layer was stripped to an oily residue. The crude product was purified by flash chromatography with 416 g 230–400 silica gel and eluting with ethyl acetate then 10:1–3 ethyl acetate:ethanol gradient. Concentration of the appropriate fractions and drying under vacuum gave 14.31 g (87.2%) of the desired product as a foamy white solid. $^1$H NMR was consistent with the desired compound.

Example 86

(S)-4-[2-Hydroxy-3-([4-(4-carbamoylphenoxy)phenyl]-2-methylpropylamino)propoxy]carbazole hydrochloride

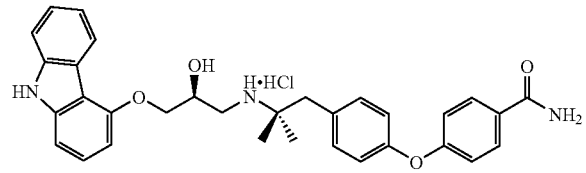

A stirred solution of the product from example 85 (11.01 g, 21.03 mmol) in 180 mL ethyl acetate (180 mL) was treated with a 1N HCl/ethyl acetate (21 mL) solution at ambient temperature. The resulting slurry was stirred for approximately 1 hour at room temperature. The slurry was pressure filtered under nitrogen through a stainless steel filter. The filter cake was washed three times with ethyl acetate (30 mL) and dried under a nitrogen purge for 2 hours. The filter cake was then dried in a vacuum oven at 60° C. overnight. This afforded 10.46 g (88.8%) of product as a white solid. EA: Calculate for $C_{32}H_{34}ClN_3O_4$: C, 68.63; H, 6.12; N, 7.50. Found: C, 68.58; H, 5.89; N, 7.17.

Example 87

(S)-4-[2-Hydroxy-3-([4-(5-carbamoyl-2-pyridyloxy) phenyl]-2-methylpropylamino)propoxy]carbazole

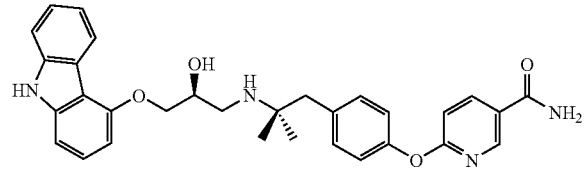

A mixture of 4-(2-amino-2-methylpropyl)phenoxy)-5-carboxamidepyridine (17.12 g, 60.00 mmol), (S)-4-(oxiranylmethoxy)-9H-carbazole (7.18 g, 30.00 mmol), HOAC (84.1 mg, 1.40 mmol), and water (10 mL) in MeOH (210 mL) was stirred at 60° C. for 22.5 hours. The mixture was cooled and concentrated in vacuo to an oil. The residue was dissolved in EtOAc (150 mL) and water (60 mL) and the resulting layers were separated. The organic layer was extracted with a solution of 1N HCl/water (28 mL/32 mL), and then with a solution of 1N HCl/water (2×2 mL/58 mL). The combined aqueous layers were extracted with EtOAc (2×60 mL) and MTBE (60 mL). The combined organic layers were washed with water (60 mL) and then were concentrated in vacuo to yield 16.01 g of a foam. Purification of the foam by flash chromatography over 230–400 mesh silica gel using first 25:4 chloroform/methanol and later 25:4:0.1 chloroform/methanol/~28% ammonia as eluents yielded 10.00 g (63.53%) of the free base. $^1$H NMR (DMSO-$d_6$) was consistent with the desired product.

Example 87(A)

(S)-4-[2-Hydroxy-3-([4-(5-carbamoyl-2-pyridyloxy) phenyl]-2-methylpropylamino)propoxy]carbazole hydrochloride salt

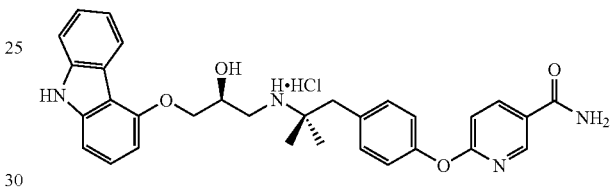

A mixture of the free base prepared above (9.80 g, 18.68 mmol) in EtOAc (150 mL) and isopropanol (19 mL) was heated to 60° C. to obtain a solution. The stirred solution was made acidic by the dropwise addition of 56.5 mL (approx. 19.2 mmol HCl) of an approximately 0.34M HCl in EtOAC solution over 30 minutes. The resulting slurry was allowed to slowly cool for 1.75 hours to ambient temperature. The mixture was filtered (nitrogen pressure). The filter cake was washed with EtOAc (2×20 mL) and dried in vacuo at 50–60° C. to yield 10.04 g (95.8%) of the desired product as a white powder. $^1$H NMR was consistent with the desired product and showed small amounts of EtOAc, IPA, and water): MS (FD+) m/z 1049 (46%), 525 (100%).

Example 88

(S)-4-[2-Hydroxy-3-([4-(5-carboxy-2-pyridyloxy) phenyl]-2-methylpropylamino)propoxy]carbazole

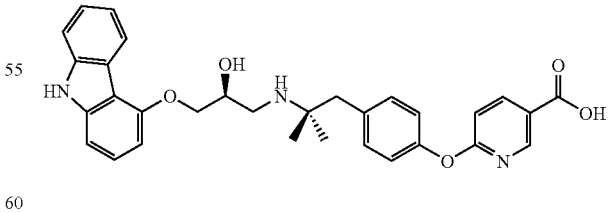

Product from Example 87 (525 mg, 1 mmol) was heated to 60° C. in 10 ml of methanol and 10 ml of 1M NaOH(aq.) for 22 hours. Reaction temperature was increased to reflux for 4 hours and the reaction cooled to room temperature. The reaction mixture was washed with isopropyl acetate and the aqueous phase acidified to a pH of 8.2 with 2M HCl and a gummy precipitate formed which crystallized upon further stirring. Solids were vigorously stirred for 4 hours, filtered, and washed with water. The solids were dissolved in 10 ml Of 0.1 M NaOH and filtered. The pH was adjusted to with 2M HCl and the solids filtered to yield 0.4 g of product. MS (m+1) 526. EA: theory: C, 70.84; H, 5.95; N, 8.00. Found: C, 70.60; H, 5.97; N, 7.98.

Example 89

(S)-4-[2-Hydroxy-3-(2-[4-phenylsulfonamidophenyl]propylamino)propoxy]carbazole

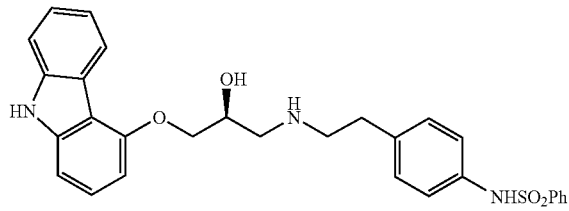

A stirred mixture of (S)-4-(oxiranylmethoxy)-9H-carbazole (478.5 mg, 2.0 mmol), N-(4-[2-aminoethyl]phenyl) benzenesulfonamide (829.1 mg, 3.0 mmol), acetic acid (1 drop), and ethanol (50 mL) was heated at 45° C. for 16 h with a slow stream of nitrogen bubbling through the reaction mixture. The mixture was cooled and concentrated in vacuo to an amorphous solid. The solid was taken up in ethyl acetate (150 mL) and washed once with 1N HCl (20 mL) and twice with aqueous saturated sodium bicarbonate solution and finally with water. The organic layer was then dried over anhydrous magnesium sulfate, filtered, and concentrated to dryness. The resulting white amorphous product was purified by radial chromatography (Chromatatron) using EtOAc:MeOH (9:1). Concentration of the appropriate fractions and drying under vacuum gave 290 mg (29%) of the desired product as an amorphous white solid. Anal. Calcd. for $C_{29}H_{29}N_3O_4S.0.5$ mol $H_2O$: C, 66.39; H, 5.76; N, 8.01. Found: C, 66.49; H, 5.81; N, 7.77.

Example 90

(S)-4-[2-Hydroxy-3-([4-(phenylsulfonamido)phenyl]-2-methylpropylamino)propoxy]carbazole

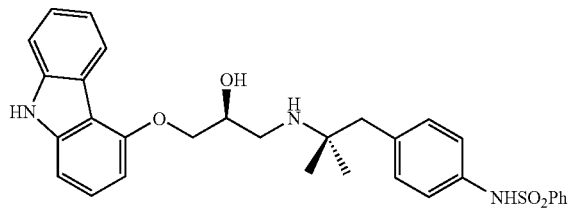

A solution of (S)-4-(oxiranylmethoxy)-9H-carbazole (1.0 g, 4.18 mmol) and N-(4-[2-methyl-2-aminopropyl]phenyl) benzenesulfonamide (1.9 g, 6.24 mmol) in absolute ethanol (100 mL) was refluxed for 18 h. The solvent was removed under vacuum and the residue was purified by column chromatography eluting with chloroform:methanol (95:5). Concentration of the appropriate fractions provided 1.53 g (69%) of the desired product. MS (FD) m/e 544.3 (MH+);

Anal. Calcd. for $C_{31}H_{33}N_3O_4S$: C, 68.48; H, 6.12; N, 7.73. Found: C, 68.49; H, 6.02; N, 7.53.

Example 91

(S)-4-[2-Hydroxy-3-([4-hydroxyphenyl]-2-methylpropylamino)propoxy]carbazole

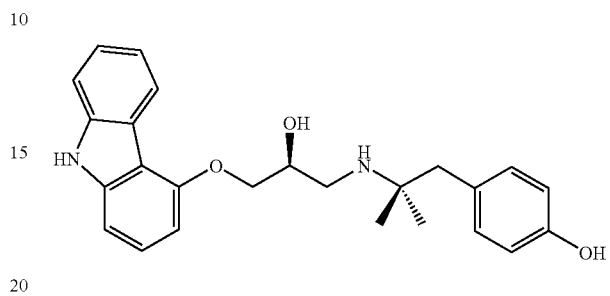

A solution of 4-(2-amino-2-methylpropyl)phenol acetic acid (2.0 g, 8.9 mmol) in water (50 mL) was treated with saturated $NaHCO_3$ (25 mL) and allowed to stand for 1 h. The resulting crystalline solid was filtered, washed with water and dried under house vacuum to provide 1.11 g (76%) of the free amine. A solution of the free amine (950 mg, 5.75 mmol) and (S)-4-(oxiranylmethoxy)-9H-carbazole (550 mg, 2.3 mmol) were refluxed in ethanol (50 mL) for 20 h. The solution was cooled to room temperature and concentrated under reduced pressure. The residue was flash chromatographed eluting with $CHCl_3$:MeOH:$NH_4OH$ (25:5:1) to give 900 mg (97%) of product. Anal. Calcd for $C_{25}H_{28}N_2O_3$: C, 74.23; H, 6.98; N, 6.93. Found: C, 74.51; H, 7.11; N, 6.88.

Example 92

(S)-4-[2-Hydroxy-3-([4-cyanomethoxyphenyl]-2-methylpropylamino)propoxy]carbazole

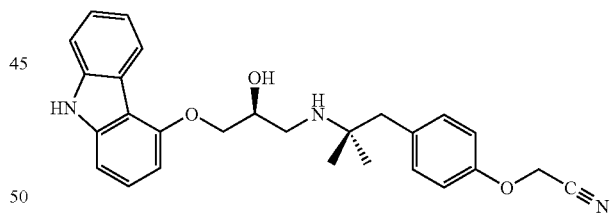

To the phenol prepared in example 91 (608 mg, 1.5 mmol) in THF (20 mL) at 0° C. was addded sodium hydride (66 mg of a 60% dispersion in oil, 1.66 mmol). After ten minutes bromoacetonitrile (199 mg, 1.66 mmol) was added. The suspension was stirred at room temperature whereupon another portion of bromoacetonitrile (360 mg, 3 mmol) was added and stirring continued until the reaction was complete by TLC. Water (50 mL) was added to the reaction and the two layers separated. The aqueous phase was extracted with ether (2×40 mL) and the combined organic phases dried ($MgSO_4$) and concentrated under reduced pressure. The residue was purified by flash chromatography eluting with 10% MeOH/$CHCl_3$ to provide 350 mg (53%) of product. Anal. Calcd for $C_{27}H_{30}N_3O_3$: C, 67.56; H, 6.30; N, 8.75. Found: C, 67.39; H, 6.51; N, 8.49.

Example 93

(S)-4-[2-Hydroxy-3-([4-carboethoxymethoxyphenyl]-2-methylpropylamino)propoxy]carbazole hydrochloride salt

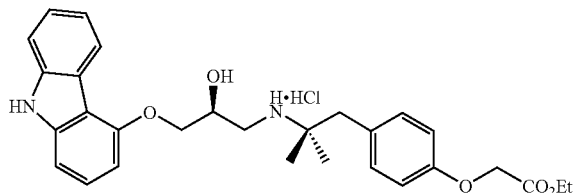

A solution of (S)-4-(oxiranylmethoxy)-9H-carbazole (0.33 g, 1.4 mmol) in ethanol (50 ml) was treated with ethyl (4-[2-amino-2-methylpropyl]phenoxy)ethanoate (0.7 g, 2.8 mmol) and stirred at reflux for 18 h. The reaction was concentrated in vacuo and the resulting residue purified by flash chromatography over silica gel eluting with 0.5% MeOH/CHCl$_3$ followed by 1% MeOH/CHCl$_3$ to provide 0.5 g (72%) of a clear oil.

The free base from above (0.45 g, 0.92 mmol) was dissolved in EtOAc (30 mL) and treated with anhydrous HCl in ether (30 mL) and concentrated in vacuo to provide 0.48 g of a white solid. MS (FD+): m/z 490. Anal Calcd for $C_{29}H_{35}ClN_2O_5$: C, 66.09; H, 6.69; N, 5.32. Found: C, 65.87; H, 6.66; N, 5.55.

Example 94

(S)-4-[2-Hydroxy-3-([4-carboxymethoxyphenyl]-2-methylpropylamino)propoxy]carbazole hydrochloride salt

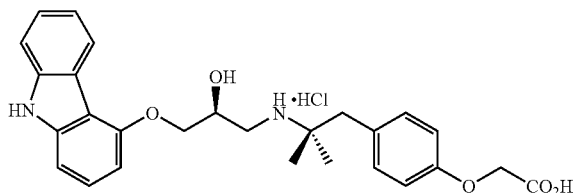

A solution of the free base (0.25 g, 0.47 mmol) from example 93 in ethanol/THF (50 mL/50 mL) was treated with 1N NaOH (14.1 mL, 14.1 mmol) and refluxed with stirring for 1 h, the reaction was neutralized with 1N HCl (13.6 mL, 13.6 mol, 29 eq), and concentrated in vacuo. The resulting residue was slurried in ether (30 ml) and anhydrous HCl in ether (30 ml) was added. The resulting slurry was concentrated in vacuo. The residue was dissolved in EtOAc and filtered. The filtrate was concentrated in vacuo to provide 0.08 g (35%) of a tan solid. MS (FD+): m/z 463. Anal Calcd for $C_{27}H_{31}N_2O_5Cl$: C, 64.99; H, 6.26; N, 5.61. Found: C, 65.29; H, 6.55; N, 5.35.

Example 95

(S)-4-[2-Hydroxy-3-{2-[4-carbamoylphenoxy]phenyl}propylamino}propoxy]carbazole

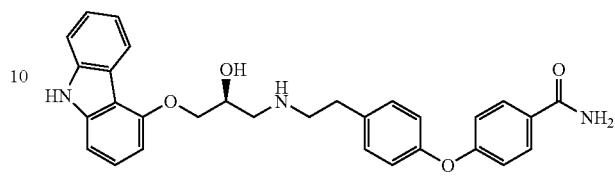

The product from Preparation 93 (0.76 g, 2.1 mmol) and (S)-(+)-4-(oxiranylmethoxy)-9H-carbazole (0.5 g, 2.2 mmol) were combined in 25 ml of dry methanol and were heated to reflux for 18 hrs under nitrogen. Ammonium formate (1.1 g, 16.7 mmol) and 10% palladium/carbon (0.2 g) were added and reflux continued for 45 minutes. The reaction mixture was filtered through celite and solvent removed in vacuo. The residue was purified by column chromotography (chloroform/methanol, 80:20) to give a white foam. The product was dried at 70° C. in a vacuum oven. MS (m+1) 497, EA: Theory: C, 70.15; H, 5.68; N, 11.28; Found: C, 68.43; H, 5.56; N, 11.13.

Example 96

(S)-4-[2-h Hydroxy-3-{2-[4-(4-carbamoylphenoxy)]}propylamino}propoxy]carbazole hydrochloride salt

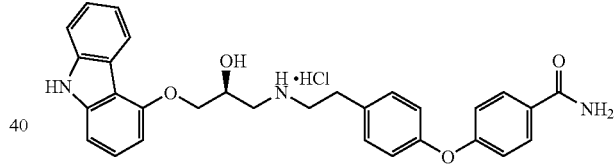

The product from Example 95 (0.25 g, 0.5 mmol) was dissolved in 40 ml of isopropanol and 0.50 ml of 1M HCl in diethyl ether was added. The solvent was removed in vacuo and the solid dried in a vacuum oven at 100° C. MS (m+1) 497(free base), EA: Theory: C, 65.35; H, 5.48; N, 10.51. Found: C, 65.10; H, 5.27; N, 10.29.

Examples 97 through 101 were prepared by utilization of the procedure outline below.

Procedure A: 0.2M solutions of both the (S)-(+)-4-(oxiranylmethoxy)-9H-carbazole and epoxides were prepared in DMSO. In a 1 dram screw cap vial was mixed 0.5 mL amine (0.1 mmol) and 0.05 mmol N,O-bis(trimethylsilyl)acetamide (BSA). After gently shaking for one-half hour, 0.6 mL (0.12 mmol) (S)-(+)-4-(oxiranylmethoxy)-9H-carbazole was added. The vial was capped and the reaction heated at 80° C. for 4–5 days. After cooling to room temperature, the reaction was quenched with 1 mL 5% HOAc/water. The reaction was diluted with 1 mL MeOH and then placed directly on a 500 mg SCX ion exchange column. Using vacuum, the column was washed with 7 mL MeOH. The collection tube under the column was changed and then the product was removed from the resin by washing with 4 mL 2N ammonia in MeOH. The solution of product was concentrated in a tarred flask and analyzed for purity by HPLC, ion-spray ms and $^1$H NMR. The average yield in the sample 10×10 plate was 35% with an average purity of 80% as determined by HPLC.

Example 97

(S)-4-[2-Hydroxy-3-([3-iodo-4-(4-carbamoylphenoxy)phenyl]-2-methylpropylamino)propoxy]carbazole

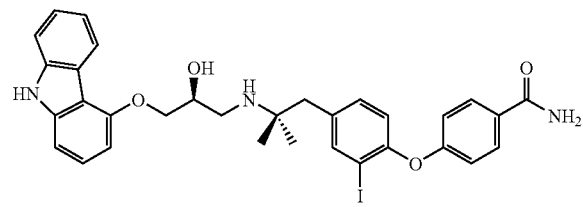

4-(2-iodo-4-(2-amino-2-methylpropyl)phenoxy)benzamide was treated according to Procedure A to yield product in 20%. MS(IEX) m+1 650.

Example 98

(S)-4-[2-Hydroxy-3-(-1-[4-aminosulfonylphenyl]-1-methylethylamino)propoxy]carbazole

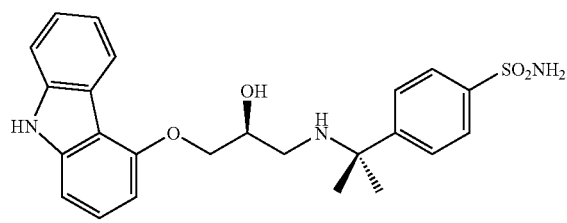

2-Methyl-2-(4-aminosulfonylphenyl)ethylamine was treated as in Procedure A to yield product in 43%. MS(IEX) m+1 454.

Example 99

(S)-4-[2-Hydroxy-3-([4-(2-carbamoylphenoxy)phenyl]-2-methylpropylamino)propoxy]carbazole

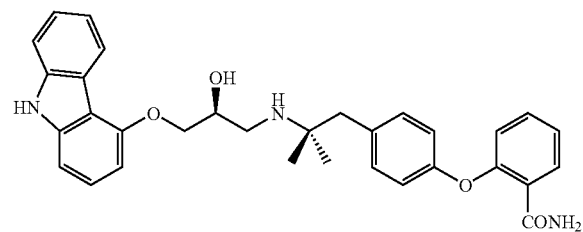

2-(4-(2-amino-2-methylpropyl)phenoxy)benzamide was treated according to Procedure A to yield product in 20%. MS(IEX) m+1 524.

Example 100

(S)-4-[2-Hydroxy-3-([4-(4-carboethoxylphenoxy)phenyl]-2-methylpropylamino)propoxy]carbazole

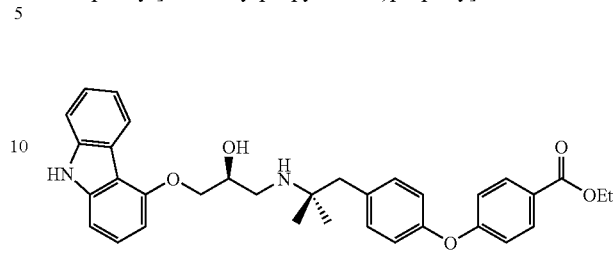

Ethyl-4-(4-(2-amino-2-methylpropyl)phenoxy)benzoate was treated as in Procedure A to yield product in 81%. MS(IEX) m+1 553.

Example 101

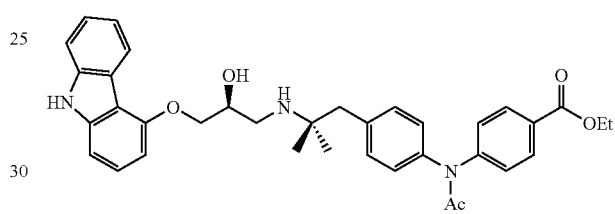

Ethyl-4-(N-acetyl-N'-4-(2-amino-2-methylpropyl)phenylamino)benzoate was treated as in Procedure A to yield product in 81%.

Example 102

(S)-4-[2-Hydroxy-3-([4-(4-carboethoxy-2-iodophenoxy)phenyl]-2-methylpropylamino)propoxy]carbazole

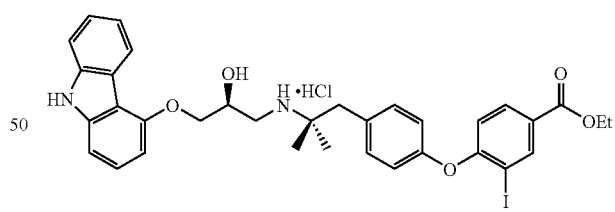

The product from preparation 94 (3.1 g, 7.06 mmol, 3 eq.) and S-(+)-glycidyl-4-hydroxycarbazole (563 mg, 2.35 mmol) were dissolved in ethanol (40 ml) and heated at 70° C. for 20 hours with stirring. The crude reaction mixture was concentrated in vacuo and applied to a flash silica column. Elution with ethyl acetate, then 9:1 ethyl acetate/ethanol afforded a white solid (1.6 g, 100%). NMR, MS. The material was dissolved in ether with methanol, filtered and treated with excess HCl (4.0N in dioxane). The resulting flocculent precipitate was filtered, triturated with pentane and dried in vacuo to afford the product as a white solid (1.19 g, 71%). NMR, MS, IR, HPLC

Example 103

(S)-4-[2-Hydroxy-3-([4-(4-carboxy-2-iodophenoxy)phenyl]-2-methylpropylamino)propoxy]carbazole

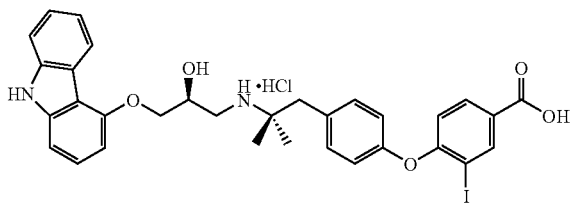

(S)-4-[2-hydroxy-3-([4-(4-carboethoxy-2-iodophenoxy)phenyl]-2-methylprbpylamino)propoxy]carbazole (386 mg, 0.54 mmol) was dissolved in a mixture of ethanol (20 ml) and aqueous potassium hydroxide (20 ml, 5.0N) and was stirred at ambient temperature for 16 hours. The crude reaction mixture was concentrated in vacuo and the residue acidified with 5.0N HCl. The solution was allowed to stir for one hour at 0° C. and then concentrated in vacuo to afford a white solid. The residue was suspended in water and filtered, and the solids washed with cold water. The solids were triturated with pentane and dried to afford product as a white solid (370 mg, 100%). NMR, MS, IR, HPLC

Example 104

(S)-4-[2-Hydroxy-3-([4-(1-methyl-1-carbamoylethoxy)phenyl]-2-methylpropylamino)propoxy]carbazole

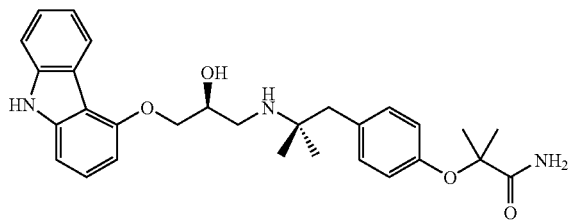

Sodium hydride (10.8 mg of a 60% dispersion in oil, 0.27 mmol) was added to a solution of the phenol prepared in example 91 (100 mg, 0.25 mmol) in dry dioxane (1 ml) and the mixture stirred for 1 h at room temperature. 2-Bromo-2-methylpropanamide (Coutts, I. G. C., Southcott, M. R. *J. Chem. Soc. Perkin Trans.* 1, 1990, 767) was then added and the mixture heated at 100° C. for 8 h. The reaction mixture was filtered, concentrated in vacuo, and purified by flash chromatography (1:1 ethyl acetate: hexanes) to afford a light yellow solid (94.4 mg, 94%). MS (FD+) 489.6, Mp 84–86° C.

Example 105

(S)-4-[2-Hydroxy-3-([4-(3-cyanopropoxy)phenyl]-2-methylpropylamino)propoxy]carbazole

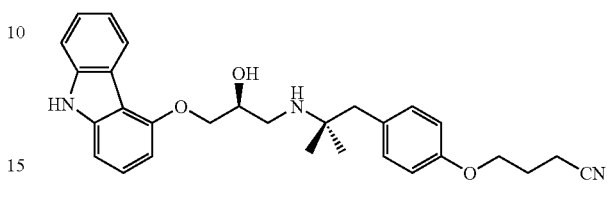

A mixture of the phenol prepared in example 91 (0.90 g, 2.2 mmol), 4-bromobutyronitrile (0.5 mL, 5.0 mmol), potassium carbonate (0.97 g, 7.0 mmol), potassium iodide (0.1 g) and methyl ethyl ketone (30 mL) was heated at reflux for 10 h. The reaction was concentrated in vacuo and the resulting residue partitioned between EtOAc and water. The layers were separated and the aqueous layer extracted with EtOAc (3×). The combined organic layers were washed with water (3×), brine, dried (MgSO$_4$), and concentrated in vacuo to a light pink oil. The material was purified by flash chromatography over silica gel eluting with 5% MeOH/CHCl$_3$ to provide 0.79 g (76%) of a clear oil. MS (FD+) 471.65. NMR.

Example 106

(S)-4-[2-Hydroxy-3-([4-(3-carbamoylpropoxy)phenyl]-2-methylpropylamino)propoxy]carbazole

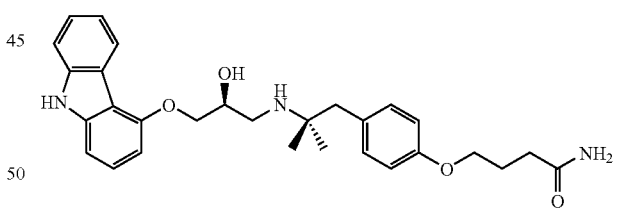

The nitrile from Example 105 (0.32 g, 0.68 mmol) and potassium carbonate (0.23 g, 1.67 mmol) were slurried in DMSO (5 mL) and cooled to 0° C. in an ice bath. Aqueous hydrogen peroxide (1.5 mL) was added slowly, and the reaction stirred at room temperature for 48 hours. The reaction was quenched by pouring into water, and extracting the aqueous layer with ethyl acetate. The combined organic layers were dried (MgSO$_4$), and concentrated in vacuo to a light tan oil. The material was purified by flash chromatography over silica gel eluting with EtOAc/hexanes/10% NH$_4$OH in MeOH (5:4:1) to provide 0.30 g (89%) of a light tan oil. MS (FD+) 489.62. NMR.

Example 107

(S)-4-[2-hydroxy-3-([4-(N-methyl-N-methoxycarbamoylmethoxy)phenyl]-2-methylpropylamino)propoxy]carbazole

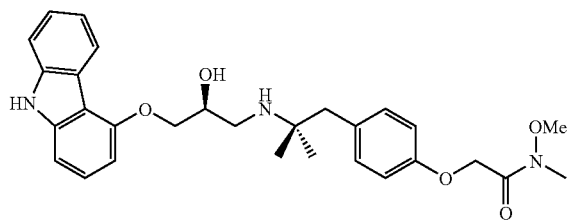

The title compound was prepared substantially in accordance with Example 105 from a mixture of phenol from Example 91 (500 mg, 1.2 mmol) and 2-chloro-N-methoxy-N-methyl acetamide (245 mg, 0.95 mmol) to yield after purification 267 mg of product. MS 505. NMR

Example 108

(S)-4-[2-Hydroxy-3-([4-(3-cyanopentoxy)phenyl]-2-methylpropylamino)propoxy]carbazole A mixture of the phenol prepared in example 91 (0.90 g, 2.2 mmol), 4-bromocaproonitrile (0.6 mL, 5.0 mmol), potassium carbonate (0.97 g, 7.0 mmol), potassium iodide (0.1 g) and mthyl ethyl ketone (30 mL) was heated at reflux for 10 h. The reaction was concentrated in vacuo and the resulting residue partitioned between EtOAc and water. The layers were separated and the aqueous layer extracted with EtOAc (3×). The combined organic layers were washed with water (3×), brine, dried (MgSO$_4$), and concentrated in vacuo to a light pink oil. The material was purified by flash chromatography over silica gel eluting with 5% MeOH/CHCl, to provide 0.80 g (72%) of a clear oil. MS (FD+) 500.78 (MH$^+$). NMR.

Example 109

(S)-4-[2-Hydroxy-3-([4-(3-carbamoylpentoxy)phenyl]-2-methylpropylamino)propoxy]carbazole

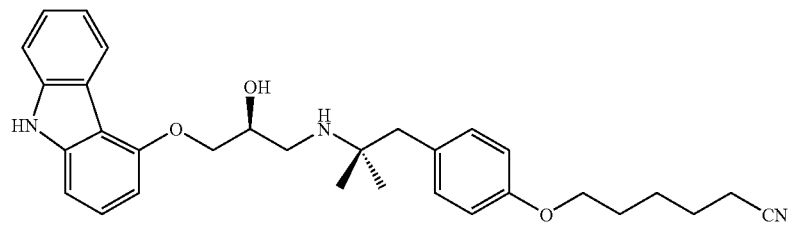

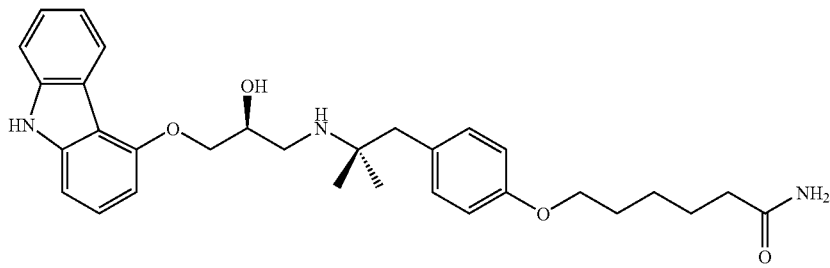

The nitrile prepared in example 108 (0.40 g, 0.80 mmol) and potassium carbonate (0.24 g, 1.70 mmol) were slurried in DMSO (5 mL) and cooled to 0° C. in an ice bath. Aqueous hydrogen peroxide (30%, 1.0 mL) was added slowly, and the reaction stirred at room temperature for 48 hours. The reaction was quenched by pouring into water, and extracting the aqueous layer with ethyl acetate. The combined organic layers were dried (MgSO$_4$), and concentrated in vacuo to a light tan oil. The material was purified by flash chromatography over silica gel eluting with EtOAc/hexanes/10% NH$_4$OH in MeOH (5:4:1) to provide 0.28 g (67%) of a colorless oil. MS (FD+) 518.07 (MH$^+$). NMR.

Example 110

(S,R)-4-[2-Hydroxy-3-([4-(4-carbamoylphenoxy)phenyl]propylamino)propoxy]carbazole

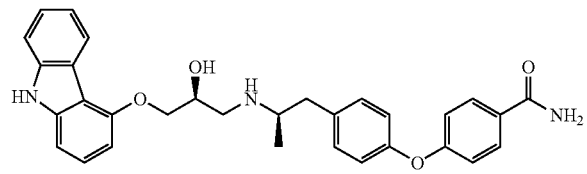

Trimethylsilylacetamide (0.26 g, 2.02 mmol) was added to a solution of the amine (0.50 g, 1.84 mmol) in DMSO (20 mL) and the mixture stirred at room temperature for 10 minutes before (S)-4-(oxiranylmethoxy)-9H-carbazole (0.44 g, 1.84 mmol) was added, and the resulting mixture heated at 66° C. for 8 h. After cooling to room temperature, the reaction was quenched with 5% AcOH/MeOH (5 mL). The crude reaction mixture was filtered through a cation-exchange column (Varian Bond Elut 500 mg SCX), and the column washed with methanol (2×5 mL). The amine was then collected by rinsing the column with 2.0M ammonia in methanol (2×5 mL). The solvent was evaporated, and the crude material purified by flash chromatography (10% methanol/chloroform) to provide the desired compound (0.44 g, 47%). MS (FD+) 511.1 (MH$^+$). EA: Calculated for C$_{30}$H$_{30}$N$_4$O$_4$: C, 70.57; H, 5.92; N, 10.97. Found: C, 70.53; H, 5.95; N, 10.94.

Example 111

(S)-4-[2-Hydroxy-3-{2-[2-methoxyphenoxy]ethylamino}propoxy]carbazole hydrochloride salt

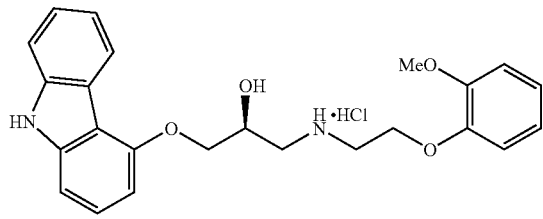

A solution of the product from preparation 96 (185 mg, 1.11 mmol) in ethanol (1 ml) was added (S)-4-(oxiranyl-methoxy)-9H-carbazole (87.9 mg, 0.37 mmol) in ethanol (5 ml) and the resulting solution was heated at 45° C. for 19 h. The reaction mixture was concentrated under reduced pressure and residue was purified by flash chromatography (10:1 CHCl$_3$/MeOH) to yield the product as a white foam (86 mg, 58%); Mass spec, found 407.1.

The hydrochloride salt was prepared by dissolving the free base in isopropyl alcohol and adding one equivalent of hydrochloric acid (as a 4M solution in dioxane). The solvent was immediately removed under reduced pressure to yield the product as a white solid; Anal. calcd. for C$_{24}$H$_{27}$N$_2$O$_4$Cl: C, 65.08; H, 6.14; N, 6.32; Cl, 8.00. Found: C, 64.86; H, 6.17; N, 6.02; Cl, 7.98.

Example 112

(S)-4-[2-Hydroxy-3-([4-(4-methylsulfonylphenoxy)phenyl]-2-methylpropylamino)propoxy]carbazole

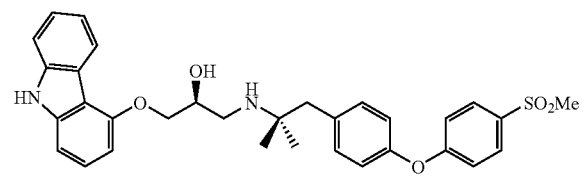

(S)-4-(oxiranylmethoxy)-9H-carbazole (0.3 g, 1.6 mmol) was added to 4-(4-(2-amino-2-methylpropyl)phenoxy)phenyl methylsulfone (1.0 g, 3.1 mmol) in 30 ml of ethanol with 2 drops of acetic acid and the reaction was heated to reflux for 16 hours. The reaction was cooled and concentrated in vacuo, and purified by column chromatography (8% methanol/EtOAc) to yield a pale yellow foam (664 mg).

MS(m+1) 510.

Example 113

(S)-4-[2-Hydroxy-3-([4-(3-trifluoromethyl-4-methyl-sulfonylphenoxy)phenyl]-2-methylpropylamino)propoxy]carbazole

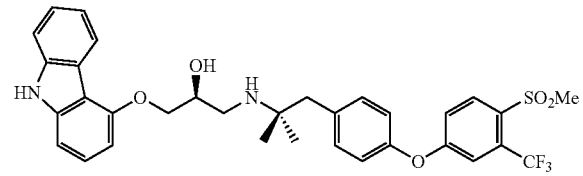

(S)-4-(oxiranylmethoxy)-9H-carbazole (0.335 g, 1.4 mmol) was added to 4-(4-(2-amino-2-methylpropyl)phenoxy)3-trifluoromethylphenyl methylsulfone (1.0 g, 3.1 mmol) in 30 ml of ethanol with 2 drops of acetic acid and the reaction was heated to reflux for 48 hours. The reaction was cooled, concentrated in vacuo, and purified by column chromatography (5% methanol/EtOAc) to yield a colorless oil (561 mg).

MS(m+1) 607.

Example 114

(S)-4-[2-Hydroxy-3-([4-carbamoylphenyl]-2-methyl-butylylamino)propoxy]carbazole

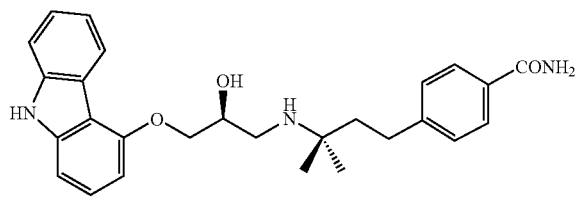

(S)-4-(oxiranylmethoxy)-9H-carbazole (0.479 g, 2 mmol) was added to 4-[3-amino-3-methylbutyl]benzamide (1.24 g, 6 mmol) in 60 ml of ethanol with 1 drop of acetic acid and the reaction was heated to 45° C. for 18 hours. The reaction was cooled, concentrated in vacuo, and purified by preparative thinlayer chromatography (100% EtOAc) to yield product as the hydrate (150 mg). MS(m+1) 446. Anal. theory: C, 72.78; H, 7.01; N, 9.43. Found: C, 69.41; H, 7.20; N, 8.99.

Example 115

(S)-4-[2-Hydroxy-3-([4-carbamoylphenyl]-2-methylpropylamino)propoxy]carbazole

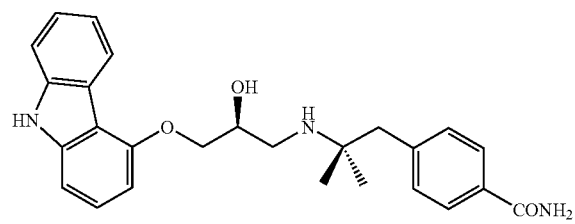

Titled compound was prepared substantially in accordance with Example 114 from (S)-4-(oxiranylmethoxy)-9H-carbazole (0.479 g, 2 mmol) and 4-[3-amino-3-methylpropyl]benzamide (580 mg, 3 mmol) to yield product after purification. MS(m+1) 432.

Example 116

(S)-4-[2-Hydroxy-3-(2-methyl-2-N-[4-cyanophenoxy]benzoylaminopropyl]amino)propoxy]carbazole

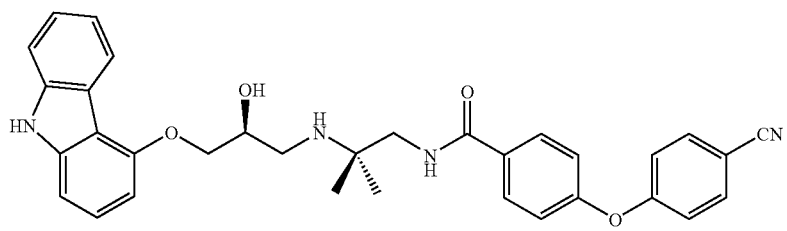

The amine from preparation 104 (0.430 g, 1.4 mmol) was combined with (S)-4-(oxiranylmethoxy)-9H-carbazole (0.225 g, 0.9 mmol) in EtOH (40 mL) and the mixture heated at 60° C. for 20 hours. The mixture was then concentrated in vacuo and the resulting residue chromatographed over silica (1–10% MeOH/CHCl$_3$) which allowed for isolation of the product as the free base. The free base was then dissolved in minimal EtOAc and treated with diethyl ether saturated with HCl (20 mL). Filtration and drying netted 0.293 g (50%) of product as the HCl salt. MS (FD+): 549 m.p. 120–130° C. (dec) Anal. Calcd for $C_{33}H_{32}N_4O_4 \cdot 1.3HCl$: C, 66.38; H, 5.63; N, 9.38. Found: C, 66.47; H, 5.54; N, 9.28.

Example 117

(S)-4-[2-Hydroxy-3-([4-(4-hydroxyphenoxy)phenyl]-2-methylpropylamino)propoxy]carbazole

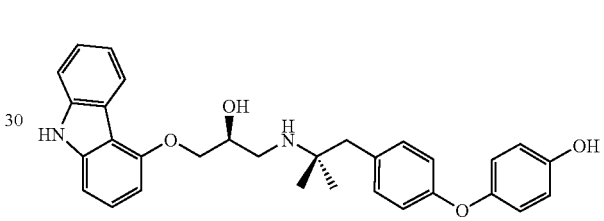

4-(4-(2-Methyl-2-aminopropyl)phenoxy)phenol (0.40 g, 1.55 mmol) was combined with (S)-4-(oxiranylmethoxy)-9H-carbazole (0.250 g, 1.0 mmol) in EtOH (50 mL) and the mixture heated at 60° C. for 20 hours. The mixture was then concentrated in vacuo and the resulting residue chromatographed over silica (1–10% MeOH/CHCl$_3$) which allowed for isolation of the product as the free base. The free base was then dissolved in minimal EtOAc and treated with diethyl ether (25 mL) saturated with HCl. Filtration and drying netted 0.410 g (76%) of product as the HCl salt. MS (FD+): 497. m.p. 80–85° C. (dec). Anal. Calcd for $C_{31}H_{32}N_2O_4 \cdot 1.3HCl$: C, 68.31; H, 6.16; N, 5.14. Found: C, 68.30; H, 6.75; N, 4.62.

Example 118

4-[2-Hydroxy-3-(2-(4-carboxyethylmethoxyphenoxy)ethylamino)]propoxy-9H-carbazole

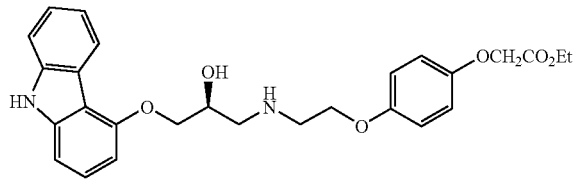

Ethyl-4-(2-aminoethyl)phenoxyacetate (0.270 g, 1.1 mmol) was combined with (S)-4-(oxiranylmethoxy)-9H-carbazole (0.200 g, 0.84 mmol) in EtOH (35 mL) and the mixture heated at 60° C. for 20 hours. The mixture was then concentrated in vacuo and the resulting residue chromatographed over silica (CHCl$_3$) which allowed for isolation of the desired product as the free base 0.22 g (55%) as well as the undesired bis-product 0.12 g (40%). The free base was treated with diethyl ether (25 mL) saturated with HCl. Filtration and drying left the product as the HCl salt. MS (FD+): 478 m.p. 57–61° C. (dec) Anal. Calcd for $C_{27}H_{29}N_2O_6 \cdot 1.85HCl$: C, 59.51; H, 5.71; N, 5.14. Found: C, 59.44; H, 5.86; N, 4.91.

Example 119

(S)-4-(3-[N-(4-[(4-carboxypiperidinyl)phenyl]-2-methyl)butylamino]-2-hydroxypropoxy)-9H-carbazole

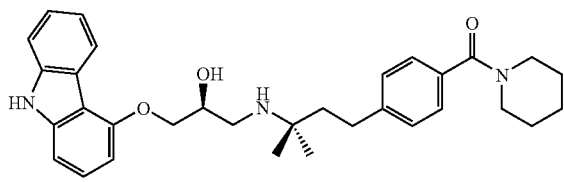

Titled compound was prepared substantially in accordance with Example 118 from (S)-4-(oxiranylmethoxy)-9H-carbazole (0.77 g) and 4-(3-methyl-3-aminobutyl)benzoic acid piperidyl amide(0.234 g) to yield product (0.87 g) after purification. MS 513.

Example 120

(S)-4-[2-Hydroxy-3-([4-(4-carbamoylphenylamido)phenyl]-2-methylbutylamino)propoxy]carbazole

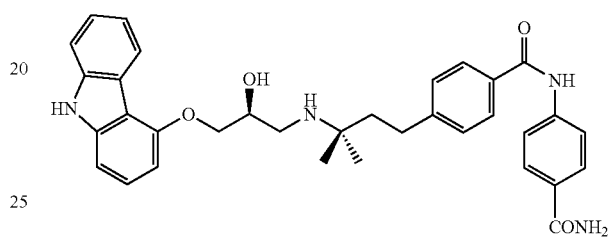

Titled compound was prepared substantially in accordance with Example 118 from (S)-4-(oxiranylmethoxy)-9H-carbazole (0.73 g) and N-(Benzamid-4-yl)-N'-butyloxycarbonyl-4-(3-methyl-3-aminobutyl)benzamide (0.21 g) to yield product (0.87 g) after purification. MS 564.

Example 121

(S)-1-Fluoro-4-[2-hydroxy-3-([4-(5-carbamoyl-2-pyridyloxy)phenyl]-2-methylpropylamino)propoxy]carbazole

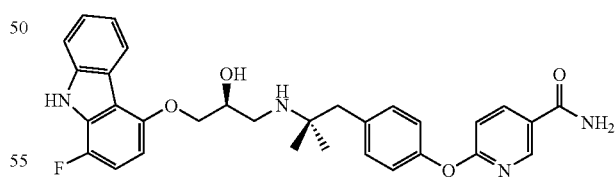

The title compound was prepared substantially in accordance with Example 118 from a mixture of 4-(2-amino-2-methylpropyl)phenoxy)-5-carboxamidepyridine (543 mg, 1.9 mmol) and (S)-1 fluoro-4-(oxiranylmethoxy)-9H-carbazole (245 mg, 0.95 mmol) to yield 417 mg of product.

Anal. Theory (1/4 H2O): C, 68.06; H, 5.80; N, 10.24. Found: C, 67.97; H, 5.83; N, 9.70.

Example 122

(S)-1-Fluoro-5-[2-hydroxy-3-([4-(5-carbamoyl-2-pyridyloxy)phenyl]-2-methylpropylamino)propoxy]carbazole

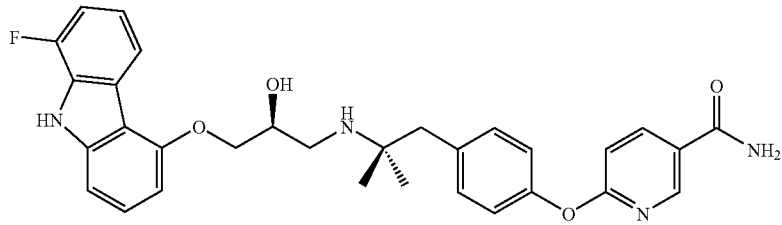

The title compound was prepared substantially in accordance with Example 118 from a mixture of 4-(2-amino-2-methylpropyl)phenoxy)-5-carboxamidepyridine (756 mg, 3.0 mmol) and (S)-1 fluoro-5-(oxiranylmethoxy)-9H-carbazole (385 mg, 1.5 mmol) to yield 750 mg of product. MS. Anal. Theory (.MeOH): C, 66.18; H, 6.14; N, 9.75. Found: C, 66.34; H, 5.97; N, 9.45.

Example 123

(S)-4-[2-Hydroxy-3-(2-[4-hydroxyphenyl]-1-carbomethoxyethylylamino)propoxy]carbazole

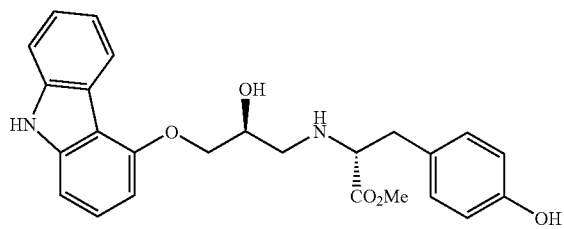

Titled compound was prepared substantially in accordance with Example 118 from (S)-4-(oxiranylmethoxy)-9H-carbazole (0.25 g) and L-tyrosine methylester (0.31 g) to yield product (0.26 g) after purification. MS 435. EA. NMR.

Example 124

(S)-4-[2-Hydroxy-3-([4-(2-pyridyloxy)phenyl]-2-methylpropylamino)propoxy]carbazole

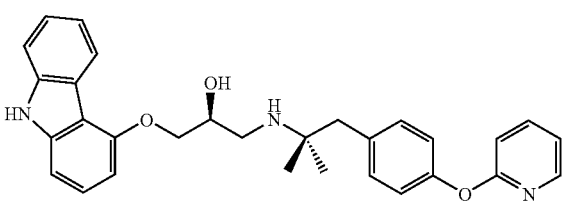

Titled compound was prepared substantially in accordance with Example 118 from (S)-4-(oxiranylmethoxy)-9H-carbazole (0.375 g) and 2-(4-(2-amino-2-methylpropyl)phenoxy)pyridine (0.496 g) to yield product (0.26 g) after purification. NMR.

Example 125

(S)-4-[2-Hydroxy-3-([4-(2-hydroxy-ethoxy)phenyl]-2-methylpropylamino)propoxy]carbazole

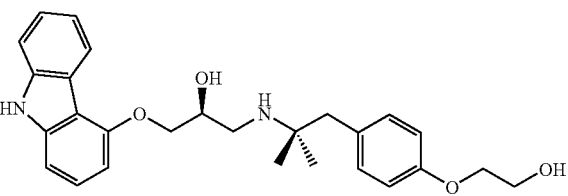

The title compound was prepared substantially in accordance with Example 118 from (S)-4-(oxiranylmethoxy)-9H-carbazole (329 mg, 1 mmol) and 1,1-dimethyl-2-(4-(2-hydroxy)ethoxy)phenyl)amine (460 mg, 2.2 mmol) to yield after purification 337 mg of product. MS 448. NMR

Example 126

(S)-4-[2-Hydroxy-3-([4-(5-carbamoyl-2-pyridyloxy)phenyl]-2-methylpropylamino)propoxy]carbazole hemisuccinate salt

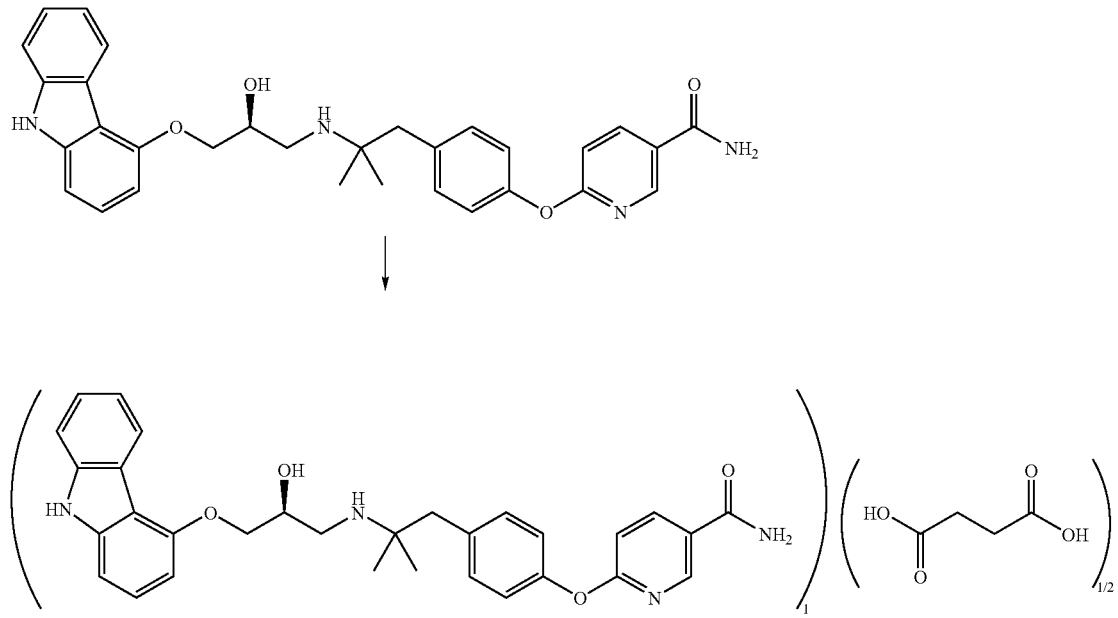

The freebase from example 87 (102.14 g, 194.69 mmol) in 511 mL of EtOAc and 1150 mL of EtOH was heated at 50–52° C. until a clear amber solution was obtained. A solution of succinic acid (11.50 g, 97.34 mmol, 0.50 mole equivalents) in 200 mL of EtOH at 50° C. was added to the solution. An additional 150 mL of EtOH was added. The resulting solution was allowed to cool. At 46° C. the mixture was seeded. Product began to crystallize at 43° C. The mixture was stirred overnight at ambient temperature.

The resulting slurry was cooled to 10° C. and filtered under vacuum. The filter cake was rinsed with 2×50 mL of 3:1 EtOH:EtOAc. The collected product was air dried under vacuum for 15 min. This gave a wet cake with a mass of 122 g. A sample (1.17 g) of the wet cake was dried under vacuum. $^1$H NMR (500 MHz, DMSO-$d_6$) was consistent with the desired hemisuccinate salt containing approximately 1.3–1.6 mole equivalents ethanol: d11.24 (s, 1H), 8.64 (d, 1H), 8.27–8.25 (m, 2H), 8.02 (s, 1H), 7.46–7.45 (d, 2H), 7.33–7.24 (m, 4H), 7.13–7.00 (m, 5H), 6.72–6.70 (s, 1H), 4.24–4.23 (d, 2H), 4.19–4.14 (m, 1H), 3.48–3.44 (q, 3.2H/2H=1.6 mol equiv. EtOH), 3.13–3.10 m, 1H), 3.00–2.97 (m, 1H), 2.76 (s, 2H), 2.35 (s, 2H, —CH2-CH2- of ½ mole equivalent succinic acid), 1.08–1.06 (m, 10H of 6H 377604+4H/3H of 1.3 mol equiv. EtOH). The material was crystalline as determined by the x-ray diffraction pattern.

The recrystallization of the majority of the material and conversion to the amorphous solid from water are described below:

The balance of the material was transferred back to the 3 L flask with 1400 mL EtOH:EtOAc (3:1). The slurry was heated to reflux (74° C. pot temp) and an additional 200 mL solvent was added to provide a clear solution. A fritted glass filter was warmed with 100 mL hot solvent, and the solution was vacuum filtered into a 3 L flask. The flask was rinsed with 2×100 mL solvent. Total solvent volume 1900 mL. The hot filtrate was allowed to slowly cool to room temperature with stirring. Product began to crystallize at 46° C. The slurry was then stirred overnight.

The mixture was cooled to 5° C. in an ice/water bath and then vacuum filtered. The collected product was rinsed with cold solvent mix (2×100 mL) and air dried under vacuum for approximately 15 min. The light cream free flowing solid was dried in a vacuum oven at 65° C. overnight to give 109.6 g. A sample weighing 4.64 g was retained.

The remainder of the material was transferred to a 2 L flask with overhead stirring. To the material was added 400 mL of filtered DI water, and the resulting slurry was stirred for 5 hours at room temperature. The slurry was then vacuum filtered and collected solid was washed with water 3×100 mL. The product was air dried under vacuum for approximately 2 hours. 1H NMR indicated there was approximately one half mole EtOH remaining in the product. The material was allowed to stand at room temperature over a weekend.

The solvate was converted to an amorphous form containing only trace residual ethanol by slurring the solvate overnight in 400 mL of water. The mixture was vacuum filtered, and the filter cake was washed with water (3×100 mL). The solid was air dried under vacuum for approximately 2 hours then in a vacuum oven (65° C.) overnight. This gave 85.92 g of product as an off white solid. Total Yield: 78.2% mp: 126–142° C.

Example 127

(S)-4-[2-hydroxy-3-([4-(5-carbamoyl-2-pyridyloxy)phenyl]-2-methylpropylamino)propoxy]carbazole hemifumarate salt ethanol solvate

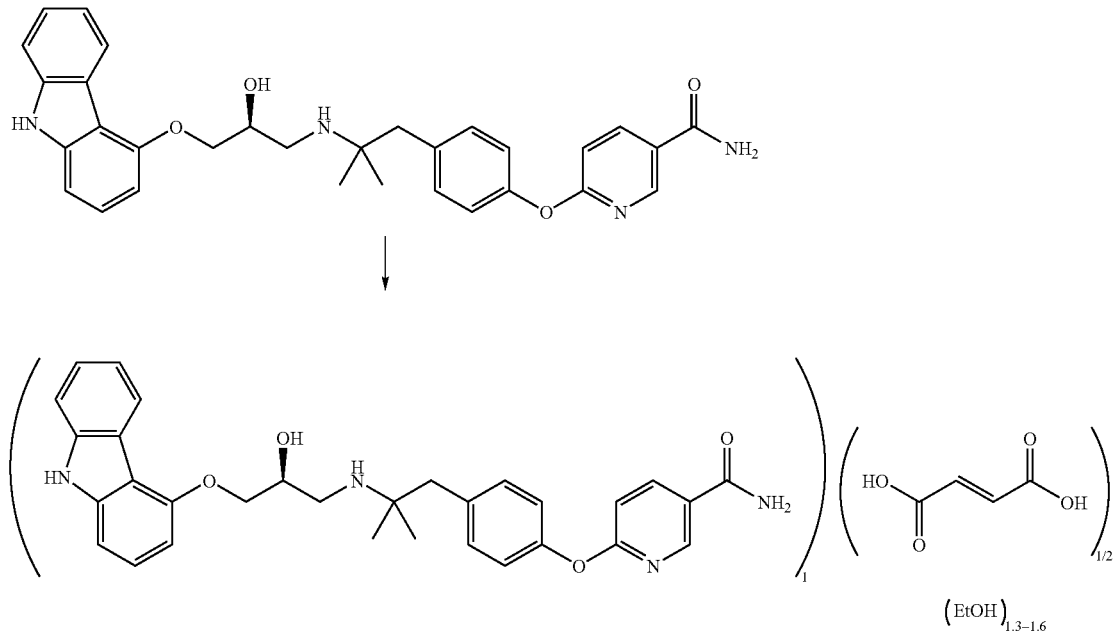

The free base from example 87 (1.26 g, 2.40 mmol), 5 mL of EtOH, and 10 mL of EtOAc were heated at approximately 50–60° C. until a solution was obtained. A solution of fumaric acid (0.14 g, 1.20 mmol, 0.5 mole equivalents) in 5 mL of EtOH was added dropwise. A precipitate was formed during the addition. An additional 6.5 mL of EtOH and 4.5 mL of EtOAc was added and the mixture was heated to reflux. Some solids remained. An additional 2.5 mL of EtOH was added and the slurry was heated at reflux for 30 minutes. The slurry was allowed to cool for approximately 1 hour and then was cooled further in an ice bath. The product was collected by vacuum filtration, washed with 2×4 mL of cold 1:1 EtOH:EtOAc, and dried under vacuum. $^1$H NMR (500 MHz, DMSO-$d_6$) was consistent with the desired hemifumarate salt containing approximately 1.3–1.6 mole equivalents ethanol: d11.25 (s, 1H), 8.64–8.63 (d, 1H), 8.27–8.25 (m, 2H), 8.0 (s, 1H), 7.46–7.44 (d, 2H), 7.33–7.25 (m, 4H), 7.11–7.02 (m, 5H), 6.72–6.70 (s, 1H), 6.53 (s, 1H, —CH═CH— of ½ mole equivalent of fumaric acid), 4.2–4.1 (m, 3H), 3.47–3.43 (q, 3.2H/2H=1.6 mol equiv. EtOH), 3.18–3.10 m, 1H), 3.05–2.95 (m, 1H), 2.80 (s, 2H), 1.11–1.05 (m, 10H of 6H 377604+4H/3H of 1.3 mol equiv. EtOH). The material was crystalline as determined by the x-ray diffraction pattern.

The following salt forms were prepared were prepared from (S)-4-[2-hydroxy-3-([4-(5-carbamoyl-2-pyridyloxy)phenyl]-2-methylpropylamino)propoxy]carbazole substantially in accordance with Example 126 and Example 127.

Example 128

(S)-4-[2-Hydroxy-3-([4-(5-carbamoyl-2-pyridyloxy)phenyl]-2-methylpropylamino)propoxy]carbazole. (phosphate)$_{1/2}$

Example 129

(S)-4-[2-Hydroxy-3-([4-(5-carbamoyl-2-pyridyloxy)phenyl]-2-methylpropylamino)propoxy]carbazole. (sulfate)$_{1/2}$

Example 130

(S)-4-[2-Hydroxy-3-([4-(5-carbamoyl-2-pyridyloxy)phenyl]-2-methylpropylamino)propoxy]carbazole. (maleate)$_{1/2}$

Example 131

(S)-4-[2-Hydroxy-3-([4-(5-carbamoyl-2-pyridyloxy)phenyl]-2-methylpropylamino)propoxy]carbazole. (L-tartrate)$_{1/2}$

Example 132

(S)-4-[2-Hydroxy-3-([4-(5-carbamoyl-2-pyridyloxy)phenyl]-2-methylpropylamino)propoxy]carbazole. (citrate)$_{1/2}$

Example 133

(S)-4-[2-Hydroxy-3-([4-(5-carbamoyl-2-pyridyloxy)phenyl]-2-methylpropylamino)propoxy]carbazole. (glutarate)$_{1/2}$

Example 134

(S)-4-[2-Hydroxy-3-([4-(5-carbamoyl-2-pyridyloxy)phenyl]-2-methylpropylamino)propoxy]carbazole. (malonate)$_{1/2}$

Example 134

(S)-4-[2-Hydroxy-3-(2-[4-phenoxy-5-carboxamidepyridin-2-yl)-(2-methyl)propyl]amino)propoxy]-9H-pyrido[3,4-b]indole hydrochloride salt

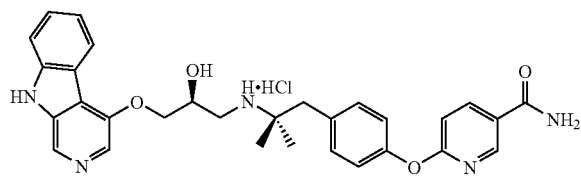

A mixture of 9H-pyrido[3,4-b]indol-4-ol (1.62 g, 8.79 mmol), (2S)-(+)-glycidyl 3-nitrobenzenesulfonate (2.28 g, 8.79 mmol), and powdered potassium carbonate (1.46 g, 10.55 mmol) in DMF (50 mL) was stirred at 40° C. for 7 hours and then placed in a freezer for 18 hours due to the instability of the product. The reaction mixture was poured into EtOAc/water (250 mL/150 mL). The layers were separated and the aqueous layer was washed with more EtOAc (250 mL) and EtOAc/THF (160 mL/80 mL). The organic portions were combined and washed with brine (2×100 mL), dried (MgSO$_4$), filtered and evaporated in vacuo to provide the crude product as a dark orange oil.

An EtOH solution (200 mL) of the crude epoxide (8.8 mmol) and 2-(4-(2-amino-2-methylpropyl)phenoxy)-5-carboxamidepyridine (5.02 g, 17.6 mmol, 2 eq) was heated at 70° C. for 18 hr. A small amount of insoluable solids were filtered off and the filtrate evaporated in vacuo to provide an oil. Some solids crystillized from the oil and were triturated with MeOH. The MeOH was decanted to leave 5.20 g of solid which by TLC contained starting amine and possible product. The MeOH portion was adsorbed on silica and passed through a silica pad with 90 CHCl$_3$/10 MeOH/1 NH$_4$OH to remove fast running impurities and then the product and starting amine were eluted together with 25 CHCl$_3$/5 MeOH/1 NH$_4$OH to give 2.35 g of a foam. The foam and the previous solids were combined (7.55 g), adsorbed on silica with CH$_2$Cl$_2$/MeOH, applied to a silica column, and then eluted with 25 EtOAc/5 MeOH/1 NH$_4$OH to give 5.60 g of product. Purification from gross impurities occurred but the starting amine and product had eluted together. The starting amine (1.23 g) was crystillized by allowing the mixture to stand in EtOAc/MeOH for 18 hr. The resulting filtrate was purified preparatively on a Waters 2000LC. using a gradient elution of 9 EtOAc/1 MeOH to 65 EtOAc/20 CH$_3$CN/13 MeOH/2 isopropylamine to give 136 mg of product. The material was dissolved in EtOAc/MeOH (10 mL/2 mL), treated with 4N HCl in dioxane (0.063 mL, 1.02 eq) and then evaporated in vacuo to give 120 mg (2.4%) of product as the HCl salt. FD: MS (FD+) m/z 526

As previously noted, the compounds of the present invention are potent, selective β3 receptor agonists. This pharmacological activity was determined in the functional agonist β3 assay.

FUNCTIONAL AGONIST ASSAYS

Cell Lines

The hβ$_2$ DNA was expressed from a plasmid 57537 obtained from American Type Culture Collection. hβ$_1$ and hβ$_3$ adrenergic receptors were cloned from human genomic libraries using the polymerase chain reaction method with degenerate probes. Full length receptors were cloned, expressed and sequenced to verify identity according to published sequences (hβ$_1$: T. Frielle et. al. (1993) *Molecular Pharmacology* 44: 264–270). These receptors were then expressed in the DXB-11 variant of CHO cells using a vector restoring tetrahydrofolate reductase and hygromycin resistance. Rat β$_3$ receptor expressing CHO cell line is known in the art. *Mol. Pharm.*, Vol 40, pp. 895–99 (1991). CHO cells were grown in 10% dialyzed FBS./high glucose DMEM/0.1% proline.

cAMP Assay

Cell membranes were harvested from the above cell line using hypotonic 25 mM Hepes (pH 7.4), 1 mM EDTA, 20 μg/mL leupeptin, 1 mM PMSF buffer with scraping followed by differential centrifugation. Membranes were incubated in 25 mM Tris (pH 7.6), 0.2% BSA, 2.6 mM Mg, 0.8 mM ATP, 0.1 mM GTP, 5 mM creatine phosphate, creatine kinase 50 U/mL, 0.2 mM IBMX at 32° C. Agonists were added and incubation continued for 15 m. cAMP produced was assayed using a fluorescent tracer-immuno assay method.

Intact cell assays were performed using suspended cells removed from culture flasks by trypsin treatment. Cells were preincubated with 0.5 mM IBMX at 37° C. Agonists were added and incubation continued for 15 min. Incubation was stopped by heating suspension in boiling water. cAMP or cGMP in these and the soleus incubations were assayed by RIA (Amersham).

The compounds of the invention are agonists of the β$_3$ receptor. Isoproterenol is accepted in the art as a non-selective β$_3$ agonist and is widely used as a comparator in evaluating the activity of compounds. See *Trends in Pharm. Sci.* 15: 3 (1994). In the Functional Agonist β$_3$ assay, the compounds demonstrated at least 30%, preferably 50% and most preferably over 85% of isoproterenol's response at a single dose of 50 mmol. Dose response titrations of the agonists described reveal EC$_{50}$ values of <10 mM, preferably <1 mmol. In the functional assay, dose titration furnishes an EC$_{50}$ for isoproterenol of 1.1±0.5 μM.

When screened against the β$_1$ and β$_2$ receptors in the functional assay, dose titration experiments indicate that greatly reduced or no receptor stimulation is observed with the compounds of the invention. This is defined by measuring the intrinsic activity (maximal response achieved) as compared to isoproterenol. The claimed compounds of Formula I are selective β$_3$ receptor agonists and have an intrinsic activity of <3% of isoproterenol's response.

Thus, the compounds of the invention are selective β$_3$ agonists.

As agonists of β$_3$, the compounds are useful in treating conditions in a mammal in which the β$_3$ receptor has been demonstrated to have a role in pathology. The preferred mammal is a human. The relationship between modulating the β$_3$ receptor and treatment of diseases, such Type II diabetes and obesity, is well established in the art. Other conditions recognized in the art include: gastrointestinal disorders such as gastrointestinal motility, asthma, depression, prostate disease and dyslipidema. Thus, the present compounds are useful in the treatment of inflammatory bowel disease (Crohn's disease or ulcerative colitis), irritable bowel syndrome, non-specific diarrhoea and dumping syndrome.

In addition, administration of compounds of the present invention can result in normalization of insulin and glucose levels in patients requiring such normalization. Therefore, the present invention would be useful in treating hyperglycemia. The present invention would also be useful for increasing metabolic rate and enhancing a patients sensitivity to insulin.

In treating non-human mammals, the compounds of the present invention are useful for increasing weight gain and/or improving the feed utilization efficiency and/or weight gain and/or improving the feed utilization efficiency and/or increasing lean body mass and/or decreasing birth mortality rate and increasing post/natal survival rate of livestock.

The compounds of Formula I are preferably formulated prior to administration. Therefore, yet another embodiment of the present invention is a pharmaceutical formulation comprising a compound of Formula I and one or more pharmaceutically acceptable carriers, diluents or excipients.

The present pharmaceutical formulations are prepared by known procedures using well-known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions are preferably formulated in a unit dosage form, each dosage containing from about 0.1 to about 500 mg, more usually about 0.5 to about 200 mg, of the active ingredient. However, it will be understood that the therapeutic dosage administered will be determined by the physician in the light of the relevant circumstances including the condition to be treated, the choice of compound to be administered and the chosen route of administration, and therefore the above dosage ranges are not intended to limit the scope of the invention in any way. The compounds can be administered by a variety of routes including the oral, rectal, transdermal, subcutaneous, topical, intravenous, intramuscular or intranasal routes. For all indications, a typical daily dose will contain from about 0.05 mg/kg to about 20 mg/kg of the active compound of this invention. Preferred daily doses will be about 0.1 to about 10 mg/kg, ideally about 0.1 to about 5 mg/kg. However, for topical administration a typical dosage is about 1 to about 500 mg compound per $cm^2$ of an affected tissue. Preferably, the applied amount of compound will range from about 30 to about 300 $mg/cm^2$, more preferably, from about 50 to about 200 $mg/cm^2$, and, most preferably, from about 60 to about 100 $mg/cm^2$.

The following formulation examples are illustrative only and are not intended to limit the scope of the invention in any way.

FORMULATION 1

Hard gelatin capsules are prepared using the following ingredients:

|  | Quantity (mg/capsule) |
|---|---|
| Active ingredient | 25 |
| starch, dried | 425 |
| magnesium stearate | 10 |
| Total | 460 mg |

The above ingredients are mixed and filled into hard gelatin capsules in 460 mg quantities.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

We claim:

1. A compound represented by the following structural formula:

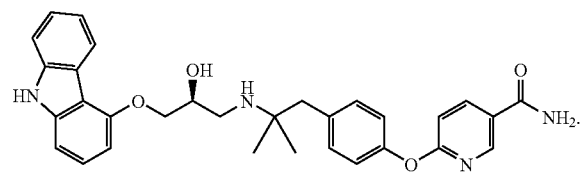

2. A 2-butyne-1,4 dioate, 3-hexyne-2,5-dioate, acetate, acrylate, beazoate, beta-hydroxybutyrate, bisulfate, bisulfite, bromide, caprylate, carbonate, chlorobenzoate, citrate, decanoate, dihydrogenphosphate, formate, fumarate, glycollate, heptanoate, hippurate, hydroxybenzoate, iodide, isobutyrate, lactate, maleate, maleate, malonate, mandelatemetaphosphate, methanesulfonate, methoxybenzoate, monohydrogenphosphate, naphthalene-1-sulfonate, naphthalene-2-sulfonate, oxalate, para-toluenesulfonate, para-bromophenylsulfonate, phenylacetate, phenylbutyrate, phenylpropionate, phosphate, phthalate, propanesulfonate, propiolate, propionate, pyrophosphate, pyrosulfate, sebacate, suberate, succinate, sulfate, sulfite, tartrate or xylenesulfonate salt of a compound represented by the following structural formula:

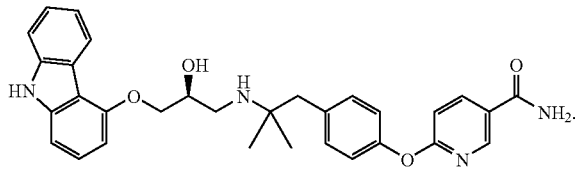

3. A pharmaceutical formulation comprising the compound of claim 1 and one or more pharmaceutically acceptable carriers, excipients or diluents.

4. A pharmaceutical formulation comprising a salt of claim 2 and one or more pharmaceutically acceptable carriers, excipients or diluents.

5. A method for treating obesity which comprises administering a pharmaceutically effective amount of a salt of claim 2 to a patient in need thereof.

6. A method for treating Type II diabetes which comprises administering a pharmaceutically effective amount of a salt of claim 2 to a patient in need thereof.

7. The salt of claim 2 which is the succinate wherein said succinate salt is the hemi-succinate.

8. A method for treating obesity which comprises administering a pharmaceutically effective amount of the salt of claim 7 to a patient in need thereof.

9. A method for treating Type II diabetes which comprises administering a pharmaceutically effective amount of the salt of claim 7 to a patient in need thereof.

* * * * *